US011293925B2

United States Patent
Wall et al.

(10) Patent No.: US 11,293,925 B2
(45) Date of Patent: Apr. 5, 2022

(54) IDENTIFYING AMYLOIDOGENIC PROTEINS AND AMYLOIDOGENIC RISK

(71) Applicant: UNIVERSITY OF TENNESSEE RESEARCH FOUNDATION, Knoxville, TN (US)

(72) Inventors: Jonathan S. Wall, Knoxville, TN (US); Emily Martin, Knoxville, TN (US)

(*) Notice: Subject to any disclaimer, the term of this patent is extended or adjusted under 35 U.S.C. 154(b) by 346 days.

(21) Appl. No.: 16/165,737

(22) Filed: Oct. 19, 2018

(65) Prior Publication Data
US 2019/0041390 A1 Feb. 7, 2019

Related U.S. Application Data

(63) Continuation of application No. PCT/US2017/028828, filed on Apr. 21, 2017.
(Continued)

(51) Int. Cl.
*G01N 33/574* (2006.01)
*G01N 33/88* (2006.01)
(Continued)

(52) U.S. Cl.
CPC ... *G01N 33/57496* (2013.01); *G01N 33/5044* (2013.01); *G01N 33/5082* (2013.01); *G01N 33/5094* (2013.01); *G01N 33/533* (2013.01); *G01N 33/534* (2013.01); *G01N 33/536* (2013.01); *G01N 33/57407* (2013.01);
(Continued)

(58) Field of Classification Search
None
See application file for complete search history.

(56) References Cited

U.S. PATENT DOCUMENTS

2002/0019335 A1\* 2/2002 Solomon ............ A61K 38/1709
424/130.1
2009/0017017 A1 1/2009 Rasmussen et al.
(Continued)

OTHER PUBLICATIONS

O'Nuallain et al., Localization of a Conformational Epitope Common to Non-Native and Fibrillar Immunoglobulin Light Chains, Biochemistry 2007, 46, 1240-1247 (Year: 2007).\*
(Continued)

*Primary Examiner* — Changhwa J Cheu
(74) *Attorney, Agent, or Firm* — FisherBroyles, LLP; Jason M. Pass

(57) ABSTRACT

Immunoglobulin light chain proteins are used to generate synthetic fibrils in vitro. The fibrils are mixed with immunoglobulin light chain proteins from a biological sample. In either a direct binding assay, competition assay, or dilution-based competition assay, a signal is detected from the mixture. The intensity of the detectable signal relates to the level of binding between the immunoglobulin light chain proteins to the fibrils and can thus be used to identify amyloidogenic immunoglobulin light chain proteins in a biological sample of the subject and to assess amyloidogenic risk to a subject. For example, the signal intensities from the assays can be used in a comparison to one or more threshold (control) values derived from samples of known light chain types or in the absence of light chains. The comparisons permit identification of amyloidogenic proteins, assessment of amyloidogenic risk, and categorization of the subject into an appropriate "at risk" group.

24 Claims, 23 Drawing Sheets

Specification includes a Sequence Listing.

Related U.S. Application Data

(60) Provisional application No. 62/326,671, filed on Apr. 22, 2016.

(51) Int. Cl.
| | |
|---|---|
| *G01N 33/50* | (2006.01) |
| *G01N 33/533* | (2006.01) |
| *G01N 33/534* | (2006.01) |
| *G01N 33/536* | (2006.01) |
| *G01N 33/58* | (2006.01) |
| *G01N 33/68* | (2006.01) |

(52) U.S. Cl.
CPC ....... *G01N 33/582* (2013.01); *G01N 33/6842* (2013.01); *G01N 33/6845* (2013.01); *G01N 33/6857* (2013.01); *G01N 2333/4709* (2013.01); *G01N 2800/7047* (2013.01)

(56) References Cited

U.S. PATENT DOCUMENTS

| | | | |
|---|---|---|---|
| 2009/0232733 A1* | 9/2009 | O'Nuallain | C07K 16/18 424/1.49 |
| 2010/0003259 A1 | 1/2010 | Ruben et al. | |
| 2013/0210168 A1* | 8/2013 | Mead | G01N 33/6857 436/501 |
| 2017/0281807 A1* | 10/2017 | Wall | A61K 47/6891 |

OTHER PUBLICATIONS

Solomon et al., Bence Jones Proteins and Light Chains of Immunoglobulins, J. Clin. Invest. 1982, 70, 453-460 (Year: 1982).*

International Search Report issued in PCT/US2017/028828 dated Sep. 12, 2017 (4 pages).
Written Opinion issued in PCT/US2017/028828 dated Sep. 12, 2017 (11 pages).
International Preliminary Report on Patentability issued in PCT/US2017/028828 dated Oct. 23, 2018 (12 pages).
Baden et al., "Light Chain Amyloidosis—Current Findings and Future Prospects", Current Protein and Peptide Science, 2009, 10:500-508.
Wall et al., "In vitro immunoglobulin light chain fibrillogenesis", Meths. in Enzymol, 1999, 309, 204-217.
Wall et al., "Thermodynamic Instability of Human λ6 Light Chains: Correlation with Fibrillogenicity", Biochemistry, 1999, 38, (42), 14101-14108.
Martin et al., "Differential recruitment efficacy of patient-derived amyloidogenic and myeloma light chain proteins by synthetic fibrils—A metric for predicting amyloid propensity", PLoS ONE, 2017, 12(3): e0174152, available at https://doi.org/10.1371/journal.pone.0174152.
Solomon et al., "Light chain-associated amyloid deposits comprised of a novel κ constant domain", Proc. Natl. Acad. Sci., 1998, 95: 9547-9551.
International Search Report and Written Opinion issued in PCT/US2015/046523 dated Jan. 28, 2016 (16 pages).
Invitation to Pay Additional Fees issued in PCT/US2015/046523 dated Nov. 5, 2015 (3 pages).
International Patent Application No. PCT/US2015/046523 filed Aug. 24, 2015, Applicant University of Tennessee Research Foundation (144 pages).
International Search Report and Written Opinion issued in PCT/US17/15905 dated Jun. 9, 2017, Applicant University of Tennessee Research Foundation (19 pages).

* cited by examiner

IDENTIFYING AMYLOIDOGENIC PROTEINS AND AMYLOIDOGENIC RISK

CROSS-REFERENCE TO RELATED APPLICATIONS

This application is a continuation of International Patent Application No. PCT/US2017/028828, filed, Apr. 21, 2017, which designated the United States and claims priority to U.S. Provisional Patent Application No. 62/326,671, filed Apr. 22, 2016, which is titled "Methods & Systems for Identifying Amyloidogenic Proteins." The entire disclosure of the above-identified priority applications are hereby fully incorporated herein by reference.

STATEMENT OF GOVERNMENT SUPPORT

This invention was made with government support under grant number R01DK079984 awarded by National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Oct. 19, 2018, is named 05820_001US1_SeqListing.txt and is 3 kilobytes in size.

TECHNICAL FIELD

The present disclosure relates generally to methods for identifying immunoglobulin light chain proteins that have a propensity toward developing amyloid deposits in a subject and, more particularly, to methods for assessing amyloidogenic risk to a subject and categorizing the subject into an appropriate at-risk population, thereby facilitating treatment of the patient.

BACKGROUND

The formation of fibrils from monoclonal immunoglobulin light chain (LC) proteins is a pathognomonic feature of light chain amyloidosis (AL). Additionally, in patients with monoclonal gammopathy of unknown significance (MGUS), multiple myeloma (MM) or related plasma cell diseases, it is estimated that up to 15% of patients may also develop clinical light chain amyloidosis during the course of their disease. Light chain amyloid observed in AL, MGUS and MM patients may deposit in any organ or tissue, but the heart, liver, spleen, kidney and nerve are most commonly involved. The persistent accumulation of amyloid in these organs, especially heart and kidney, results in architectural damage and, possibly, the dysfunction of cellular metabolism, which ultimately leads to progressive organ dysfunction and death.

The prognosis for patients with LC-associated amyloidosis depends on the major anatomic site of amyloid deposition. Cardiomyopathy, due to amyloid deposition in the myocardium, is present in more than 50% of AL patients and is associated with a ~6-9-month survival from the time of diagnosis. For all AL patients, the median survival is 3 years with a 5-year survival rate of approximately 30%. In patients with MM, osteolytic bone lesions are common and often accompanied by renal cast nephropathy due to an accumulation of amorphous LC protein deposits in the proximal renal tubules, but amyloidosis secondary to MM occurs after the initial MM diagnosis and in only 15% of patients. The American Cancer Society data indicates that the overall survival of stage I MM patients is 62 months. In patients with MM, only comorbidities of amyloidosis and renal impairment served as statistically significant independent prognostic factors that adversely affected patient survival. It is unclear what biochemical or pathophysiological factors dictate which ~15% of MM patients will develop clinical LC amyloidosis. By analogy to AL amyloidosis, however, it is likely dependent upon a complex combination of protein-related and host-associated factors. In patients with MGUS, the presence of circulating free light chain can result in renal complications, but usually, there is little clinical pathology and, as such, MGUS is generally considered a pre-cancerous state where "watchful-waiting" is the clinical approach. Patients with MGUS can develop LC amyloidosis or progress to develop MM, but the relative risk of the former is not well understood.

For all types of amyloid, fibril formation is an autocatalytic polymerization reaction, which is characterized by a lag phase at the beginning of the reaction during which a thermodynamically unfavorable protein misfolding event occurs, ultimately yielding a relatively stable oligomeric species known as the "seed." This phase is followed by a period of rapid, exponential fibril growth during which the fibril mass increases due to the thermodynamically favorable recruitment of precursor proteins by the seed. Its similarity to a crystallization reaction is evidenced by the fact that fibril growth can be induced by the introduction, into a solution of suitable precursor protein, of pre-formed fibrils (seed) that act as a nidus, or template, which fosters rapid recruitment of the protein from solution. Seeded fibril growth reactions in vitro are characterized by rapid increase in fibril mass and the absence of a lag phase. Amyloid seeding is a degenerate phenomenon and may involve heterologous precursor proteins, i.e., "cross-seeding", wherein fibril seeds composed of one precursor protein can recruit structurally and biochemically different precursor proteins; template-induced seeding of amyloid precursor proteins underlies the transmissibility of amyloid diseases and prionopathies.

In AL amyloidosis, the amyloid fibrils are composed principally of LC fragments, most commonly the LC variable domain with a small number of constant domain amino acids as evidenced from amino acid sequencing of peptides isolated from human amyloid extracts. Mass spectrometric analysis of amyloid deposits has also shown the presence of LC constant domain fragments and, therefore, presumably full length protein. The precise mechanisms of LC amyloid formation and growth in patients remain poorly characterized. Of particular importance is the role of circulating free LC proteins in amyloid fibril growth. It remains unclear whether the LC proteins undergo proteolysis resulting in variable domain fragments prior to incorporation into the fibril, or if, alternatively, amyloid fibrils grow via the interaction of intact LC proteins that undergo proteolytic cleavage after recruitment of the protein which then releases the constant domain fragments. Furthermore, it is unknown whether both the initial formation of an amyloid seed and subsequent elongation, or growth of the amyloid fibril, involves principally the LC variable domain or the full length LC.

In the laboratory, studies of LC amyloid fibril formation from soluble precursor proteins (fibrillogenesis or de novo fibril formation) have focused almost exclusively on the use of recombinant LC variable domain (VL) fragments of κ4, λ6, and κ1 LC subgroups. Fibril formation from these components often requires denaturing conditions such as low pH or the presence of chaotropes, indicating the need for mildly denaturing conditions to initiate protein misfolding and fibril formation. Certain VL fragments, however, have been shown to undergo fibrillogenesis in physiological milieu such as the recombinant λ6 LC VL derived from patient Wil, designated rVλ6Wil. These in vitro studies have demonstrated a general inverse correlation between VL folding free energy and the propensity for in vitro fibrillogenesis, such that less stably folded VL domains are more prone to form fibrils, from monomer, as compared to more stable VL domains.

Despite the increased understanding of fibril formation and growth in vitro, the recruitment of circulating intact LCs, monoclonal or polyclonal, by amyloid fibrils has yet to be systematically elucidated. Likewise, in the absence of isolating every patient LC and determining the amino acid sequence and, thereafter, the folding stability (a complex and arduous task), the ability to identify which LCs may have a propensity towards developing amyloid fibrils is limited—a prospect that is particularly troubling for patients that are "at risk" of developing amyloidosis. These "at risk" patients include, for example, those afflicted with an amyloid precursor disease (characterized generally by the presence of a serum free LC) such as multiple myeloma, smoldering multiple myeloma, Waldenstrom's macroglobulinemia, and the more than 3 million Americans with a monoclonal gammopathy of unknown significance (MGUS). Because early intervention is beneficial in the prevention and/or treatment of amyloidosis, the ability to categorize patients with serum free LC's who are at increased risk for developing amyloidosis during the course of their disease would be highly beneficial. For example, such patient categorization would help dictate the use of additional patient treatments that are specific for the prevention and/or removal of amyloid deposits or for preventing the build-up of amyloid-related components that are toxic to body organs.

SUMMARY

In certain example aspects, provided herein are methods of identifying amyloidogenic immunoglobulin light chain proteins in a biological sample that includes immunoglobulin light chains. For example, in certain aspects a direct binding assay is provided. The assay includes providing a plurality of detectably-labeled immunoglobulin light chain proteins from a biological sample. The plurality of detectably-labeled immunoglobulin light chain proteins from the biological sample are then contacted with a plurality of synthetic amyloid fibrils to form a reaction mixture. A signal intensity value is determined from the reaction mixture. When the signal intensity value exceeds a threshold value, the immunoglobulin light chain proteins are amyloidogenic. When the signal intensity value falls below a threshold value, the immunoglobulin light chain proteins can be deemed non-amyloidogenic. The threshold value can be assigned to the assay or can be determined using known sample types, such as amyloidogenic or non-amyloidogenic sample types.

In certain example aspects, a competition assay is provided for identifying amyloidogenic proteins from a biological sample. For example, a biological sample that includes immunoglobulin light chain proteins is contacted with a plurality of detectably-labeled synthetic fibril precursor monomers to form a reaction mixture. The reaction mixture is then contacted with a plurality of synthetic amyloid fibrils to form a second reaction mixture. The synthetic fibrils, for example, include polymers of the synthetic fibril precursor monomers. A signal intensity value is then determined from the second reaction mixture. When the signal intensity value falls below a threshold value, the immunoglobulin light chain proteins of the biological sample are amyloidogenic. As with the direct binding assay, the threshold value for the competition assay can be assigned to the assay or can be determined using known sample types, such as amyloidogenic or non-amyloidogenic sample types.

In certain example aspects, a dilution-based competition assay is provided for identifying amyloidogenic proteins from a biological sample. For example, a plurality of sample dilutions from a biological sample are provided. The sample dilutions, for example, each include a different concentration of the biological sample. The sample dilutions are then each contacted with a plurality of detectably-labeled synthetic fibril precursor monomers to form a plurality of reaction mixtures. Each of the reaction mixtures are then contacted with a plurality of synthetic amyloid fibrils to form a set of second reaction mixtures. The synthetic fibrils, for example, include polymers of the synthetic fibril precursor monomers. A signal is then detected from each of the second reaction mixtures. From the detected signals, a gradient value for the biological sample is determined. The sample gradient value falls below a threshold value when the immunoglobulin light chain proteins of the biological sample are amyloidogenic. In certain example aspects, the threshold value for the dilution-based competition assay can be assigned to the assay. In other example aspects, the threshold values can be determined using known sample types, such as amyloidogenic or non-amyloidogenic sample types.

In certain example aspects, the direct binding assay, competition assay, and dilution based assay can be used to assess amyloidogenic risk of a subject. With the direct binding assay and competition assay, for example, a determined signal intensity value for the biological sample is compared to a threshold value. In the dilution-based assay, for example, a gradient value for the biological sample is compared to a threshold value. Such comparisons, for example, provide an indication of amyloidogenic risk for the subject.

These and other aspects, objects, features and advantages of the example embodiments will become apparent to those having ordinary skill in the art upon consideration of the following detailed description of illustrated example embodiments.

BRIEF DESCRIPTION OF THE DRAWINGS

The accompanying drawings, which are incorporated in and constitute a part of this specification, illustrate certain aspects of the instant invention and, together with the description, serve to explain, without limitation, the principles of the invention.

FIG. 6A is an electron micrograph of AL1κ recruited by rVλ6Wil fibrils. 10 nm-diameter gold particles (arrows) indicate the presence of the anti-κ mAb (bound to the AL1κ LC) on the fibrils (arrowheads). FIG. 6B is an electron micrographs of rVλ6Wil fibrils in a control experiment where no anti-κ LC mAb was added. This image shows that the avidin-conjugated gold particles do not bind the fibrils in the absence of biotinylated Ab bound to the AL LC on the fibrils.

FIG. 7A shows recruitment (% bound) of $^{125}$I-labeled AL1κ proteins by rVλ6Wil fibrils. FIG. 7B shows recruitment (% bound) of $^{125}$I-labeled AL2κ proteins by rVλ6Wil fibrils. FIG. 7C shows recruitment (% bound) of $^{125}$I labeled MM1κ proteins by rVλ6Wil fibrils. FIG. 7D shows recruitment (% bound) of $^{125}$I-labeled MM2κ proteins by rVλ6Wil fibrils. Rates were calculated using a single exponential binding equation, and the $R^2$ for each fit was >0.95. These data show that synthetic rVλ6Wil fibrils are capable of recruiting ALκ and MMκ patient-derived LC proteins. However, the AL-LC's recruit more rapidly and more extensively, based on the amount bound at 24 h, as compared to MM-LC's. Similar results were seen for lambda light chain proteins. FIG. 7E shows recruitment of $^{125}$I labeled proteins AL1λ by rVλ6Wil fibrils. FIG. 7F shows recruitment of $^{125}$I-labeled proteins AL2λ by rVλ6Wil fibrils. FIG. 7G shows recruitment of $^{125}$I-labeled proteins MM1λ by rVλ6Wil fibrils. FIG. 7H shows recruitment of $^{125}$I-labeled proteins MM2λ by rVλ6Wil fibrils. In general, the AL-LC's recruit more rapidly and more extensively, based on the amount bound at 24 h, as compared to MM-LC's.

FIG. 8A shows recruitment of $^{125}$I-labeled κ (circle) and λ (square) LC by rVλ6Wil fibrils after 1 h, 3 h, or 24 h of incubation. There was no significant difference in the recruitment of LC proteins when grouped into κ or λ isotypes. FIG. 8B shows recruitment of AL- (circle) and MM-associated (square) LC was significantly different at 1 h, 3 h, or 24 h of incubation (**, p<0.005). When the LC were separated into AL and MM type, there was a significant difference in the recruitment amount at all time points.

FIG. 19A shows MM- (white) and AL (black) LC proteins added at concentrations of 0.05 µM, 0.1 µM, 0.5 µM, 2 µM, 4 µM and 5 µM to the recruitment reaction mixture. The binding of biotinyl-rVλ6Wil monomer was measured and expressed as europium fluorescence emission (au, arbitrary units). Data are plotted using a linear x-axis. FIG. 19B shows the same data plotted in a log 10 x-axis and fit using a semilog linear equation (y=m log x+c). The gradient of the increase in inhibition as the LC concentration increases (given by the gradient, m, in the equation) was calculated and shown to be significantly more negative for AL LC as compared to MM LC. The measurement of m can provide a measure of assessing amyloidogenic potential of LC using this method.

FIG. 20A shows analysis of concentration-dependent inhibition by four MM patient LC. Data were presented as described in FIG. 19 on a semilog x-axis. FIG. 20B shows analysis of concentration-dependent inhibition by five AL patient LC. Data were presented as described in FIG. 19 on a semilog x-axis. This figure shows that the concentration inhibition gradient (m) of AL LC proteins is significantly more negative as compared to MM LC proteins.

FIG. 21A is a graph showing the gradient of inhibition (m is the "slope of inhibition change") for AL (black) and MM (white) LC proteins. The AL LC have a significantly more negative slope as compared to MM LC. FIG. 21B shows a receiver operator curve of the data presented in FIG. 21A indicating that, for these LC proteins, the area under the curve is 1, indicating perfect discrimination of AL LC from MM LC using this method of analysis.

DETAILED DESCRIPTION OF THE EXAMPLE EMBODIMENTS

Overview

Figure 1:
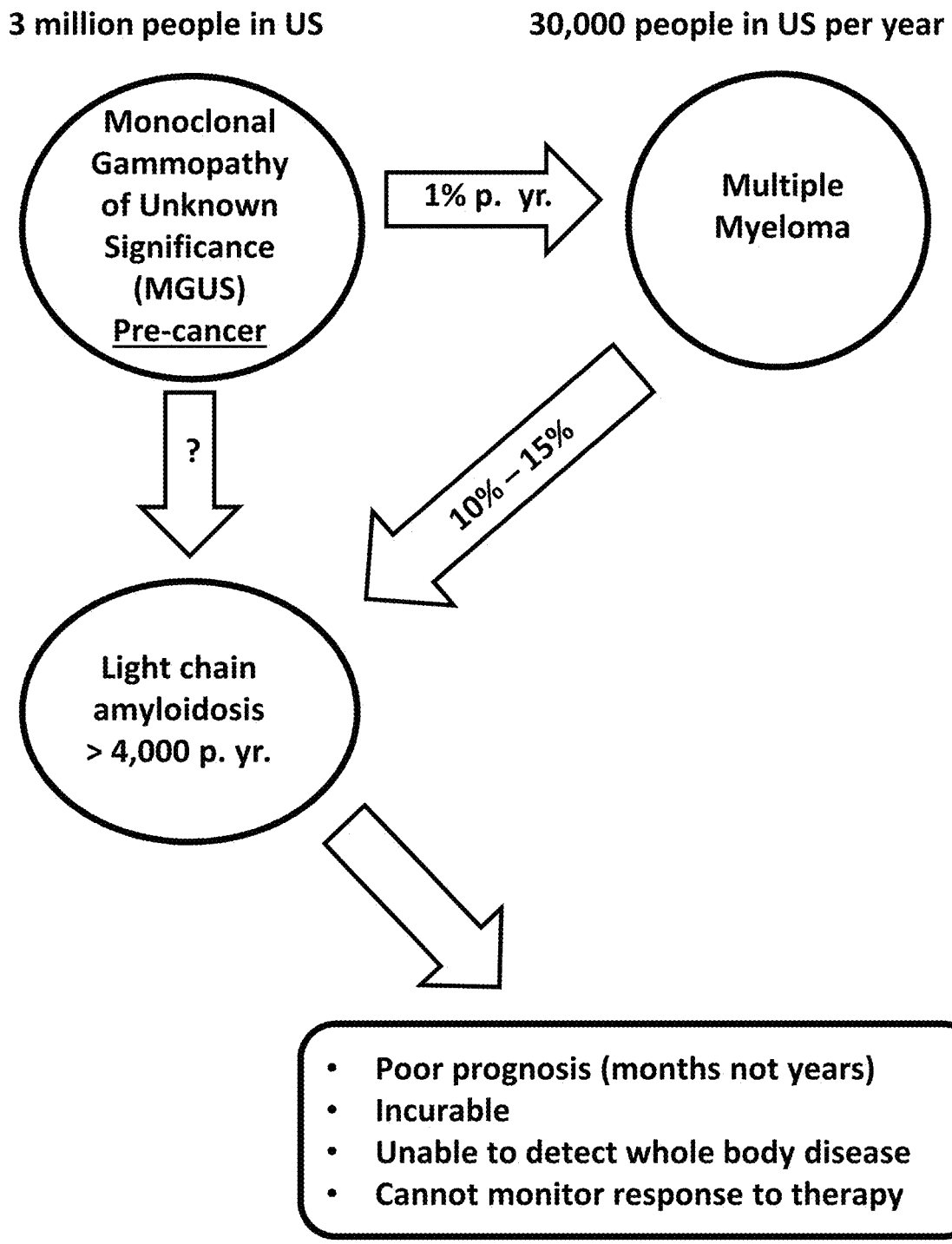
FIG. 1 is a schematic illustration showing the relationship between patients with monoclonal gammopathy of unknown significance (MGUS), multiple myeloma (MM) and light chain amyloidosis (AL). Incidence data were taken from the SEER database at the NC. This shows that there is a clinical need to be able to identify patients from the MGUS and MM groups who may develop AL (before they are diagnosed with AL) so that they can be monitored more carefully and treated more aggressively by the introduction of anti-amyloid therapeutics than the other patients in those groups.
Figure 2:
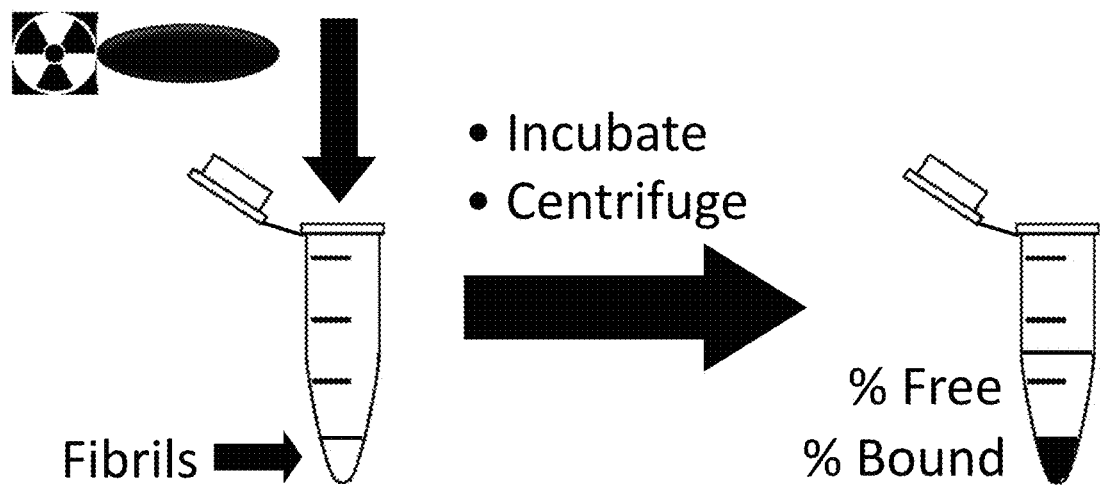
FIG. 2 is a schematic illustration of a pulldown assay (direct binding assay) used to generate LC-fibril binding data, in accordance with certain example embodiments. In a typical assay, 25 μg of synthetic rVλ6Wil fibrils prepared in the laboratory are mixed with 5 ng of either iodine-125 ($^{125}$I)-labeled rVλ6Wil monomer or $^{125}$I-labeled LC isolated from patients with MM or AL. The patient LC can be of either the λ or κ isotype, for example. The sample is mixed for 1 h, 3 h or 24 h, and then the unbound material in the supernatant is removed by centrifugation at ~15,000×g and quantified. The amount bound is then quantified and is expressed as a percent of the total radioactivity measured (bound plus free).

As described herein, immunoglobulin light chain monomers can be used to generate synthetic fibrils in vitro. The fibrils can then be mixed with immunoglobulin light chain proteins from a biological sample of a subject, and—in either a direct binding assay or competition assay—a signal is detected from the mixture. In both assays, the intensity of the detectable signal relates to the level of binding between the immunoglobulin light chain proteins to the fibrils. The intensity can thus be used to identify amyloidogenic immunoglobulin light chain proteins in a biological sample of the subject. In certain examples, the signal intensities from the assays can be used in a comparison to one or more threshold values (control) derived from samples of known light chain types or in the absence of light chains. As described herein, such comparisons permit categorization of the subject into an appropriate "at risk" group and hence facilitate treatment of the subject.

More particularly, the synthetic fibrils described herein can be formed in vitro from any immunoglobulin light chain or fragments thereof known that form fibrils, including any variable domain immunoglobulin light chain proteins (lambda or kappa light chains), constant domain immunoglobulin light chain proteins, or mixtures thereof. To identify amyloidogenic proteins from a subject, a biological sample can be obtained from the subject, such as a blood or urine sample. The subject, for example, can be any subject for which testing with the methods described herein may be warranted or beneficial.

In the direct binding assay provided herein, immunoglobulin light chain proteins can be isolated from the biological sample of the subject. The isolated immunoglobulin light chain proteins can then be labeled with a detectable marker and contacted with the synthetic fibrils, thereby forming a reaction mixture. Following incubation of the reaction mixture, the intensity of the detectable signal generated from the reaction mixture can be determined and used to assess the amyloidogenic nature of the biological sample (and hence the amyloidogenic risk the subject).

In certain examples, the signal intensity from the direct binding assay reaction mixture is compared to a positive control to determine a signal intensity value for the reaction mixture. For the positive control, labeled fibril precursor monomers can be used in a direct binding assay (instead of the biological sample) to determine a maximum signal intensity. The signal intensities from the reaction mixture of the biological sample can then be compared to the maximum signal intensity to determine a signal intensity value for the sample. For example, a signal intensity of the biological sample that is about half of the maximum signal intensity can have a signal intensity value of about 50%. A strong signal intensity value from the reaction mixture in the direct binding assay—which relates to an increased binding of the subject's immunoglobulin light chain protein to the synthetic fibrils in the reaction mixture—indicates that the subject's immunoglobulin light chain proteins are more amyloidogenic. Conversely, a weak signal intensity value in the binding assay indicates that the immunoglobulin light chain proteins in the biological sample are less amyloidogenic.

In certain examples, the signal intensity value of the reaction mixture can be compared to one or more assigned or predetermined threshold values to determine whether the immunoglobulin light proteins in the biological sample are amyloidogenic. In certain examples, the threshold values can be determined from direct binding assays in which isolated immunoglobulin light chain proteins from a particular sample type (e.g., an amyloid, multiple myeloma, MGUS, or healthy sample) are labeled and contacted with the synthetic fibrils in a reaction mixture. A signal intensity is then determined from the reaction mixture, and compared to a positive control (signal maximum) signal intensity as described herein. The threshold values for the various sample types can then be determined from the comparison.

In determining an "amyloid threshold" using an amyloid sample, for example—in which light chain immunoglobulins are expected to readily bind to the synthetic fibrils in vitro—the determined threshold value corresponds to a value that is close to or matches to the positive control. Conversely, with a non-amyloidogenic sample—in which light chain immunoglobulins are not expected to bind to the synthetic fibrils as much as an amyloid sample—the "non-amyloidogenic" threshold value can be a determined value that is significantly less than the positive control.

In certain examples, by comparing the signal intensity value of a subject's reaction mixture to one or more of the threshold values for the particular sample types, the subject can be placed into an appropriate "at risk" group, thereby facilitating treatment of the subject. For example, a subject whose reaction mixture signal intensity value meets or exceeds an "amyloid threshold" can be deemed to have a high risk for developing amyloidosis and treated accordingly. A subject whose reaction mixture signal intensity value is very low, however, may fall below a non-amyloidogenic threshold and thus deemed to have a low risk of developing amyloidosis. Such a subject, for example, can have a different treatment protocol than a subject identified as having an amyloidogenic light chain.

Like the direct binding assay, the competition assay provided herein can also be used to identify amyloidogenic proteins in a biological sample of a subject, thereby facilitating treatment of the subject. In certain examples, an advantage of the competition assay is that isolation of a subject's light chain immunoglobulins—and then direct labeling of those isolated immunoglobulins—is not needed. For example, a biological sample can be taken from a subject. Separately, fibril precursor monomers can be detectably labeled and then mixed with the sample to form a reaction mixture. The reaction mixture can then be mixed with the synthetic fibrils to form a second reaction mixture. Without wishing to be bound by any particular theory, it is believed that the subject's light chain immunoglobulins in the biological sample compete with the labeled fibril precursor monomers for binding to the synthetic fibrils in the second reaction mixture.

Following a wash step to remove any unbound labeled fibril monomers or immunoglobulin light chains from the patient sample, the signal intensity from the second reaction mixture can be determined. In certain examples, the signal intensity from the second reaction mixture can be compared to a positive control to determine a signal intensity value for the second reaction mixture. For the positive control, fibril precursor monomers can be detectably labeled and mixed with the appropriate healthy biological sample (e.g., healthy human serum) to form a control reaction mixture. The control reaction mixture can then be contacted with synthetic fibrils to form a second control reaction mixture. A signal intensity from the second control reaction mixture can then be determined, and this signal can correspond to the maximum signal intensity in the competition assay. The signal intensity from the biological sample can then be compared to the maximum signal intensity to determine the relative signal intensity value for the biological sample. For example, a signal intensity of the biological sample that is about half of the maximum signal intensity can have a signal intensity value of about 50%.

Because amyloidogenic light chain immunoglobulins are believed to compete with the labeled fibril monomers for binding to the synthetic fibrils in the competition assay, the lower the determined signal intensity value from the second reaction mixture of a biological sample, the more likely the light chain immunoglobulins in the biological sample are to be amyloidogenic. That is, more light chain immunoglobulin proteins from the biological sample are believed to bind to the synthetic fibrils, thereby partially blocking (via competition) the labeled fibril monomers from binding the synthetic fibrils. Hence, the lower the signal intensity value from the second reaction mixture, the more of the subject's light chain immunoglobulins bind the fibrils, thus indicating the presence of amyloidogenic protein in the subject. Conversely, the higher the signal intensity value, fewer of the subject's light chain immunoglobulins bind the fibrils, thus indicating the presence of non-amyloidogenic protein in the subject.

In certain examples, the signal intensity value generated from the second reaction mixture of a subject's biological sample using the competition assay can be compared to one or more threshold values to identify amyloidogenic proteins in the biological sample. The threshold values can be determined, for example, from competition assays in which the signal intensities from light chain proteins from a particular sample type (e.g., an amyloid, multiple myeloma, a MUGS, or healthy sample) are compared to the signal intensity of a positive control as described above. The threshold values for the various sample types can then be determined from the comparison.

In determining an "amyloid threshold" from an amyloid sample, for example—in which light chain immunoglobulins are expected to compete with labeled precursor monomers for binding to the synthetic fibrils—the determined amyloid threshold value corresponds to a value that is well below the signal intensity of the positive control (where binding is maximized). Conversely, in a non-amyloidogenic sample—in which light chain immunoglobulins are not expected to bind to the synthetic fibrils as much as an amyloid sample—the threshold value (i.e., "non-amyloidogenic threshold" value) corresponds to a value that is close to or matches the positive control.

In certain examples, by comparing the signal intensity value of the subject's second reaction mixture to one or more of the particular sample threshold values, the subject can be placed into an appropriate "at risk" group thus facilitating treatment of the subject. For example, if a determined signal intensity value of the second reaction mixture from a subject's biological sample is at or greater than a threshold value for a non-amyloidogenic threshold—meaning that less of the subject's immunoglobulin light chain proteins bound the synthetic fibrils and allowed the labeled precursor to bind the fibrils—the subject can be classified as having a low risk of additionally developing immunoglobulin light chain amyloid deposits. In contrast, if the signal intensity value is less than the non-amyloidogenic threshold—thus indicating increased binding of the light chain proteins in the subject's sample to the synthetic fibrils—the subject can be classified as having a high risk of developing amyloidosis (or as having amyloidosis). The subject can then be monitored and treated according to the subject's increased likelihood of developing amyloidosis.

In certain examples of the competition assay, a subject's biological sample can be diluted to form two or more sample dilutions. Each of the sample dilutions can then be mixed with detectably labeled precursor monomers to generate multiple reaction mixtures (of the competition assay). The reaction mixtures can then be contacted with fibrils to form a corresponding set of second reaction mixtures of the competition assay. The signal intensities of each of the diluted samples can then be determined as described herein, in accordance with the competition assay. Because amyloidogenic light chain immunoglobulins are believed to compete with the labeled fibril precursor monomers for binding to the synthetic fibrils in the competition assay, inhibition of the binding will be greatest in the least-dilute subject sample (i.e., the highest concentration sample). Hence, using the set of signal intensity values and corresponding dilution values, a gradient value can be obtained in which the lower the determined gradient value, the more likely the light chain immunoglobulins in the biological sample are to be amyloidogenic. That is, more light chain immunoglobulin proteins from the biological sample are believed to bind to the synthetic fibrils, thereby partially blocking (via competition) the labeled fibril precursor monomers from binding the synthetic fibrils. Hence, the lower the gradient (i.e., more negative) the more of the subject's light chain immunoglobulins bind the fibrils, thus indicating the presence of amyloidogenic protein in the subject. Conversely, the higher the gradient (i.e., the less negative or more positive), fewer of the subject's light chain immunoglobulins bind the fibrils, thus indicating the presence of non-amyloidogenic protein in the subject.

In certain examples, the gradient value can be compared to a threshold value. For example, the threshold value can be an assigned gradient level, below which the immunoglobulin light chain proteins in a biological sample can be deemed to be amyloidogenic and above which the immunoglobulin light chain proteins can be deemed non-amyloidogenic. In certain example embodiments, the threshold values for the dilution-based competition assay can be determined by using known sample types with the dilution-based competition assay. For example, an amyloid sample can be used with the dilution-based completion assay, and the resultant gradient value can be used to establish one or more threshold values. A gradient value of a biological sample that is at or falls below an "amyloid threshold," for example, can be deemed to include amyloidogenic immunoglobulin light chains, whereas a gradient value above the "amyloid threshold" (i.e., less negative) can be deemed non-amyloidogenic. As with the direct binding assay or the competition assay, the dilution-based competition assay can be used to place a subject into a specific risk group.

By using and relying on the methods described herein, a subject identified as having highly amyloidogenic immunoglobulin light chain protein may undergo a treatment protocol that is different than a subject that is identified non-amyloidogenic. For example, a subject with amyloidogenic lights chain proteins can be monitored with greater frequency for the presence of amyloid deposits. This can involve routinely performing subcutaneous fat biopsies, such as every six months, and determining the presence of amyloid in the biopsies by histological staining. Additionally or alternatively, the subject can routinely undergo an imaging procedure to detect the presence of amyloid deposits. In certain examples, a subject identified as amyloidogenic can be treated with monoclonal antibodies for the removal of tissue amyloid or prevention of deposition of amyloid. In contrast, if a subject is determined via the methods described herein to have low amyloidogenic immunoglobulin light chain protein, the subject can be monitored and be treated with the standard of care for subjects with multiple myeloma. In other examples, a subject with low amyloidogenic proteins may undergo a watchful waiting protocol.

Summary of Terms

The invention will now be described in detail by way of reference only using the following definitions and examples. All patents and publications, including all sequences disclosed within such patents and publications, referred to herein are expressly incorporated by reference in their entirety.

Unless otherwise noted, technical terms are used according to conventional usage. Definitions of common terms in molecular biology may be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710) and other similar references. As used herein, the singular forms "a," "an," and "the," refer to both the singular as well as plural, unless the context clearly indicates otherwise. The abbreviation, "e.g." is derived from the Latin exempli gratia, and is used herein to indicate a non-limiting example. Thus, the abbreviation "e.g." is synonymous with the term "for example." As used herein, the term "comprises" means "includes." All publications, patent applications, patents, and other references mentioned herein are expressly incorporated herein by reference in their entirety.

Although methods and materials similar or equivalent to those described herein can be used in the practice or testing of this disclosure, suitable methods and materials are described below. In case of conflict, the present specification, including explanations of terms, will control. In addition, the materials, methods, and examples are illustrative only and not intended to be limiting. Further, while steps of a method may be recited, it is understood that the specific steps of the method may be carried out in any other sequence that achieves the intended result. To facilitate review of the various example embodiments of this disclosure, the explanations of specific terms are provided below.

Unless otherwise indicated, nucleic acids are written left to right in 5' to 3' orientation; amino acid sequences are written left to right in amino to carboxy orientation, respectively. The headings provided herein are not limitations of the various aspects or embodiments of the invention which can be had by reference to the specification as a whole. Accordingly, the terms defined immediately below are more fully defined by reference to the specification as a whole.

As used herein, the singular forms "a," "an" and "the" include plural referents unless the context clearly dictates otherwise.

Ranges can be expressed herein as from "about" one particular value, and/or to "about" another particular value. When such a range is expressed, another aspect includes from the one particular value of the range and/or to the other particular value of the range. It will be further understood that the endpoints of each of the ranges are significant both in relation to the other endpoint, and independently of the other endpoint. Similarly, when values are expressed as approximations, by use of the antecedent "about," it will be understood that the particular value forms another aspect. In certain example embodiments, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about. Further, terms used herein such as "example," "exemplary," or "exemplified," are not meant to show preference, but rather to explain that the aspect discussed thereafter is merely one example of the aspect presented.

"Animal" refers to living multi-cellular vertebrate organisms, a category that includes, for example, mammals and birds.

"Amino acid" or "amino acid residue" refers to any naturally occurring amino acid, any non-naturally occurring amino acid, any modified amino acid, including derivatized amino acid, or any amino acid mimetic known in the art. The amino acid may be referred by both their common three-letter abbreviation and single letter abbreviation. In its broadest sense, an "amino acid" refers to any compound and/or substance that can be incorporated into a polypeptide chain. In some embodiments, an amino acid has the general structure $H_2N$—$C(H)(R)$—$COOH$. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides.

A "nonstandard amino acid" refers to any amino acid, other than the standard amino acids, regardless of whether it is prepared synthetically or obtained from a natural source. A "synthetic amino acid" or "non-natural amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, and/or substitution with other chemicals without adversely affecting their activity. Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide. It should be noted that all amino acid residue sequences are represented herein by formulae whose left and right orientation is in the conventional direction of amino-terminus to carboxy-terminus. As used herein a "protein" refers to a biological molecule encoded by a gene and comprised of amino acids.

The terms "amyloids," "amyloid deposits," "amyloid fibrils," and "amyloid fibers" refer to insoluble fibrous protein aggregates sharing specific structural traits. The protein aggregates have a tertiary structure, for example, that is formed by aggregation of any of several different proteins and that consists of an ordered arrangement of β sheets stacked perpendicular to a fiber axis. See Sunde et al., J. Mol. Biol. (1997) 273:729-39. Abnormal accumulation of amyloids in organs may lead to amyloidosis. Although they are diverse in their occurrence, all amyloids have common morphologic properties in that they stain with specific dyes such as Congo red and have a characteristic red-green birefringent appearance in polarized light after staining. Amyloids also share common ultrastructural features and common x-ray diffraction and infrared spectra.

"Amyloidosis" refers to a pathological condition or disease characterized by the presence of amyloids, such as the presence of amyloid deposits. "Amyloid diseases" or "amyloidosis" are diseases associated with the formation, deposition, accumulation or persistence of amyloid fibrils. Such diseases include, but are not limited to, Alzheimer's disease, Down's syndrome, hereditary cerebral hemorrhage with amyloidosis of the Dutch type, and cerebral beta-amyloid angiopathy. Other amyloid diseases such as systemic AA amyloidosis, AL amyloidosis, ATTR amyloidosis, ALect2 amyloidosis, and IAPP amyloidosis of type II diabetes are also amyloid diseases.

"Amyloidogenic" refers to producing or tending to produce amyloid deposits. For example, certain soluble monomeric proteins can undergo extensive conformational changes leading to their aggregation into well-ordered, unbranching, 8- to 10-nm wide fibrils, which culminate in the formation of amyloid aggregates. More than thirty proteins, for example, have been found to form amyloid deposits (or amyloids) in man. Not all proteins within the class of diverse proteins, such as immunoglobulin light chains, are capable of forming amyloid, i.e., some proteins are non-amyloidogenic, meaning that they do not tend to form amyloids. Other proteins of the class, however, can form amyloid deposits and are thus amyloidogenic. Furthermore, within the class of light chain protein, some may be deemed more "amyloidogenic" than others based upon the ease with which they form amyloid fibrils. Certain light chain proteins are deemed non-amyloidogenic or less amyloidogenic because of their inability to readily form amyloid fibrils in patients or in vitro.

The terms "cellular expression" or "cellular gene expression" generally refer to the cellular processes by which a biologically active polypeptide is produced from a DNA sequence and exhibits a biological activity in a cell. As such, gene expression involves the processes of transcription and translation but can also involve post-transcriptional and post-translational processes that can influence a biological activity of a gene or gene product. These processes include, for example, RNA synthesis, processing, and transport, as well as polypeptide synthesis, transport, and post-translational modification of polypeptides. Additionally, processes that affect protein-protein interactions within the cell can also affect gene expression as defined herein.

"DNA" refers to a molecule comprising at least one deoxyribonucleotide residue. A "deoxyribonucleotide" is a nucleotide without a hydroxyl group and, instead, a hydrogen at the 2' position of a β-D-deoxyribofuranose moiety. The term encompasses double stranded DNA, single stranded DNA, DNAs with both double stranded and single stranded regions, isolated DNA such as partially purified DNA, essentially pure DNA, synthetic DNA, recombinantly produced DNA, as well as altered DNA, or analog DNA, that differs from naturally occurring DNA by the addition, deletion, substitution, and/or modification of one or more nucleotides.

An "expression cassette" or "expression vector" is a nucleic acid construct generated recombinantly or synthetically with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

A "fibril" is a small filament or fiber. The fibril, for example, consists of a polymer of precursor monomers, i.e., multiple precursor monomers form a fibril. For example, an amyloid fibril is a small fiber made of amyloid protein monomers. A "fibrillar precursor monomer" or "fibril precursor monomer," for example, is a monomer that can be incorporated into the fibril.

The term "gene" includes a coding strand and a non-coding strand. As used herein, the terms "coding strand" and "sense strand" are used interchangeably and refer to a nucleic acid sequence that has the same sequence of nucleotides as an mRNA from which the gene product is translated. As is also understood in the art, when the coding strand and/or sense strand is used to refer to a DNA molecule, the coding/sense strand includes thymidine residues instead of the uridine residues found in the corresponding mRNA. Additionally, when used to refer to a DNA molecule, the coding/sense strand can also include additional elements not found in the mRNA including, but not limited to, promoters, enhancers, and introns. Similarly, the terms "template strand," "antisense strand," "template DNA molecule," "DNA template strand," or the like are used interchangeably and refer to a nucleic acid sequence that is complementary to the coding/sense strand.

By the term "host cell," it is meant a cell that contains a vector and supports the replication, and/or transcription or transcription and translation (expression) of the expression construct. Host cells can be prokaryotic cells, such as *E. coli* or *Bacillus subtilus*, or eukaryotic cells such as yeast, plant, insect, amphibian, or mammalian cells. In general, host cells are prokaryotic, e.g., *E. coli*.

The term "immunoglobulin light chain" refers to the protein product of four immunoglobulin germline genes (V, D, J, C) and is a component of an antibody protein, which comprises two light chain proteins and two immunoglobulin heavy chain proteins. Light chain proteins may be of either the kappa or lambda subgroup and are approximately 215 amino acids in length. The light chain protein is comprised of two distinct domains—the variable and constant domains, which are classical immunoglobulin domains stabilized by an intra-chain disulfide bond and other electrostatic and hydrophobic interactions between amino acids. The amino acid sequence of light chain proteins is encoded in the germline gene sequences but also is altered due to somatic mutations in the variable domain. The presence of serum monoclonal immunoglobulin light chain proteins is associated with numerous plasma cell-related diseases (plasma cell dyscrasias) including multiple myeloma, MGUS, and light chain amyloidosis. Somatic mutation of amino acids in the monoclonal free light chain proteins, as well as post-translational modifications, determine the folding stability of the light chain protein. Less stably folded light chain proteins in the serum have a higher propensity to form amyloid fibrils as compared to more stably folded proteins.

"Label" refers to a detectable compound or composition that is conjugated directly or indirectly to another molecule to facilitate detection of that molecule. Specific, non-limiting examples of labels include fluorescent tags, chemiluminescent tags, haptens, enzymatic linkages, and radioactive isotopes. A protein that is "detectably-labeled," for example, means that the presence of the protein can be determined by a label associated with the protein.

A "mammal" refers to any animal classified as a mammal, including humans, domestic and farm animals, and zoo, sports, or pet animals, such as dogs, cats, cattle, horses, sheep, pigs, and so on. The mammal may be a human.

"Peptide" refers to any peptide or peptidomimetic structure comprising or consisting of two or more amino acids, including chemical modifications and derivatives of amino acids. A "polypeptide" refers to a polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein is intended to encompass any amino acid sequence and include modified sequences such as glycoproteins. The term "polypeptide" is specifically intended to cover naturally occurring proteins, as well as those that are recombinantly or synthetically produced.

A "purified" or "isolated" molecule refers to biological or synthetic molecules that are removed from their natural environment and are isolated or separated and are free from other components with which they are naturally associated. The term "purified" does not require absolute purity; rather, it is intended as a relative term. Thus, for example, a purified or "substantially pure" protein preparation is one in which the protein referred to is more pure than the protein in its natural environment within a cell or within a production reaction chamber (as appropriate). In certain examples, a molecule is present in a sample at a concentration of at least 95% by weight, or at least 98% by weight of the sample in which it is contained.

The term "bind" or "specifically binds" refers to a non-random binding reaction between two molecules. The term "specifically binds" may be used interchangeably with "binds," "selectively targets," "recruits," or "selectively associates." In certain example embodiments, the term "recruit" is used to denote binding. For example, a fibril precursor monomer can be recruited to a synthetic amyloid fibril, meaning that the fibril precursor monomer non-randomly interacts with the synthetic amyloid fibril.

As used herein, "sequence identity" or "identity" refers to the similarity between two nucleic acid sequences, or two amino acid sequences, and is expressed in terms of the similarity between the sequences, otherwise referred to as sequence identity. Sequence identity is frequently measured in terms of percentage identity (or similarity or homology); the higher the percentage, the more similar the two sequences are. For example, 80% homology means the same thing as 80% sequence identity determined by a defined algorithm, and accordingly a homologue of a given sequence has greater than 80% sequence identity over a length of the given sequence. Example levels of sequence identity include, for example, 80, 85, 90, 95, 98% or more sequence identity to a given sequence, e.g., the coding sequence for any one of the inventive polypeptides, as described herein. Methods of alignment of sequences for comparison are well known in the art. Various programs and alignment algorithms are described in: Smith & Waterman *Adv. Appl. Math.* 2: 482, 1981; Needleman & Wunsch *J. Mol. Biol.* 48: 443, 1970; Pearson & Lipman *Proc. Natl. Acad. Sci. USA* 85: 2444, 1988; Higgins & Sharp *Gene* 73: 237-244, 1988; Higgins & Sharp *CABIOS* 5: 151-153, 1989; Corpet et al. *Nuc. Acids Res.* 16, 10881-90, 1988; Huang et al. *Computer Appls. In the Biosciences* 8, 155-65, 1992; and Pearson et al. *Meth. Mol. Bio.* 24, 307-31, 1994. Altschul et al. (*J. Mol. Biol.* 215:403-410, 1990) presents a detailed consideration of sequence alignment methods and homology calculations. The NCBI Basic Local Alignment Search Tool (BLAST) (Altschul et al. *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

A "subject" refers to a vertebrate. The vertebrate may be a mammal, for example, a human. The subject may be a human patient. A subject may be a patient suffering from or suspected of suffering from a disease or condition and may be in need of treatment or diagnosis or may be in need of monitoring for the progression of the disease or condition. The patient may also be in on a treatment therapy that needs to be monitored for efficacy. In some example embodiments, a subject includes a subject suffering from amyloidosis, multiple myeloma, or Monoclonal Gammopathy of Unknown Significance (MGUS).

The terms "treating" or "treatment" refer to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Example Embodiments

Multiple myeloma (MM) and light chain (AL) amyloidosis are plasma cell dyscrasias characterized by the presence of serum free monoclonal immunoglobulin light chain proteins. In subjects with MM, immunoglobulin light chain proteins accumulate as amorphous casts in the renal tubules and may, later in the disease, also develop into amyloid deposits. Subjects with an amyloidogenic light chain protein develop debilitating systemic fibrillar deposits of amyloid.

As described herein, we have developed sensitive assays to identify immunoglobulin light chain proteins using synthetic amyloid fibrils. For example, we have shown that AL light chain and MM light chain proteins can both be recruited efficiently by synthetic fibrils. Amyloid-associated light chains, however, can be recruited significantly more effectively than MM light chains, thus permitting differentiation of subject groups. In certain example embodiments, light chain proteins (such as either AL or MM, for example) can be recruited by synthetic amyloid fibrils. The efficiency of recruitment can thus be used to identify those MM patients—and indeed others with monoclonal gammopathy of unknown significance, for example—who are at risk for developing amyloidosis due to the presence of a light chain with enhanced amyloidogenic propensity.

Thus, in certain example embodiments provided are assays—both direct binding assays and competition-based assays—for identifying amyloidogenic proteins in a biological sample, such as a biological sample of a subject. Also included are methods of treating a subject identified as having amyloidogenic proteins. In accordance with the methods described herein, pre-formed synthetic fibrils can be used in the assays to determine the recruitment of immunoglobulin light chain proteins to the fibrils in vitro. That is, the synthetic fibrils, for example, act as a seed to recruit and specifically bind the immunoglobulin light chain proteins. Additionally or alternatively, the methods provided herein permit the identification of amyloidogenic protein from a biological sample of a subject, thus permitting classification of the subject as "at risk" for developing amyloidosis. The subject can then be treated accordingly.

Synthetic Amyloid Fibrils

To identify amyloidogenic immunoglobulin LC, the methods and systems described herein rely on synthetic amyloid fibrils that are formed from fibril precursor monomers. The synthetic fibrils can be made in vitro, for example, from any immunoglobulin light chain or fragments thereof known in the art to form fibrils. In certain example embodiments, the light chain of the fibril can be $\kappa 1$, $\kappa 2$, $\kappa 3$, $\kappa 4$, or $\kappa 5$ light chain or fragments thereof. Additionally or alternatively, the light chain of the fibrils is $\lambda 1$, $\lambda 2$, $\lambda 3$, $\lambda 4$, $\lambda 5$, $\lambda 6$, $\lambda 7$, $\lambda 8$, $\lambda 9$, or $\lambda 10$ or fragments thereof. In certain example embodiments, the fibril includes combinations of different light chains, such as combinations of $\kappa 1$, $\kappa 2$, $\kappa 3$, $\kappa 4$, $\kappa 5$, $\lambda 1$, $\lambda 2$, $\lambda 3$, $\lambda 4$, $\lambda 5$, $\lambda 6$, $\lambda 7$, $\lambda 8$, $\lambda 9$, or $\lambda 10$ or fragments thereof.

The fibrils can be made according to methods known in the art, including those described in Wall, J. S., Murphy, C. L. and Solomon, A. (1999), *In vitro immunoglobulin light chain fibrillogenesis*. Meths. in Enzymol, 309, 204-217; Wall, J. S., Schell, M., Murphy, C., Hrncic, R., Stevens, F. and Solomon, A. (1999) *Thermodynamic Instability of Human λ6 Light Chains: Correlation with Fibrillogenicity*. Biochemistry, 38, (42), 14101-14108, both of which are expressly incorporated herein by reference. As an example, precursor monomers can be suspended in a sterile solution of phosphate buffered saline, pH 7.5 with (or without) chaotropes (e.g., guanidine hydrochloride or potassium thiocyanate), or they may be suspended in a buffered saline solution at low pH (e.g., pH 2-4). The solution of precursor monomers can then be placed in a plastic or glass tube and incubated with (or without) shaking for a period of time to allow the formation of synthetic fibrils. In some cases, this can be as little as 48 hours, and in other cases, it may require many weeks. Upon formation of fibrils, seen as a milky precipitate in the tube, the suspension is centrifuged and the supernatant removed and the fibril pellet resuspended in appropriate buffered solution.

In certain example embodiments, the synthetic fibril is made or derived from one or more genes or genetic alleles encoding the immunoglobulin kappa variable group. These genes or genetic alleles include, for example, IGKV1-5, IGKV1-6, IGKV1-8, IGKV1-9, IGKV1-12, IGKV1-16, IGKV1-17, IGKV1-27, IGKV1-33, IGKV1D-8, IGKV1D-12, IGKV1D-13, IGKV1D-16, IGKV1D-17, IGKV1D-22, IGKV1D-27, IGKV1D-32, IGKV1D-33, IGKV1D-39, IGKV1D-43, IGKV2-24, IGKV2-28, IGKV2-30, IGKV2-40, IGKV2D-26, IGKV2D-28, IGKV2D-29, IGKV2D-30, IGKV2D-40, IGKV3-11, IGKV3-15, IGKV3-20, IGKV3D-7, IGKV3D-11, IGKV3D-20, IGKV4-1, or IGKV5-2 or combinations thereof. Example kappa variable group genetic alleles that can be used in accordance with the methods provided herein are provided in Table 1, below.

TABLE 1

Example Kappa Variable Group Genes or Genetic Alleles.

| Allele names | Clone name | Accession numbers | NCBI Gene Designation |
|---|---|---|---|
| IGKV1-5*01 | L12 | Z00001 | Gene ID: 28299 |
| IGKV1-5*02 | V1 | M23851 | |
| IGKV1-5*03 | L12a | X72813 | |
| IGKV1-6*01 | L11(Vf) | M64858 | Gene ID: 28943 |
| IGKV1-6*02 | — | KM455558 | |
| IGKV1-8*01 | L9(Ve) | Z00014 (K02097) | Gene ID: 28942 |
| IGKV1-9*01 | L8(Vd) | Z00013 (K02096) | Gene ID: 28941 |
| IGKV1-12*01 | L5 | V01577 | Gene ID: 28940 |
| IGKV1-12*02 | L5/19a(V4b; Vb') | V01576 | |
| IGKV1-16*01 | L1(HK137; Q14) | J00248 | Gene ID: 28938 |
| IGKV1-16*02 | — | FM164406 | |
| IGKV1-17*01 | A30 | X72808 | Gene ID: 28937 |
| IGKV1-17*02 | A30 | D88255 | |
| IGKV1-17*03 | — | KM455566 | |
| IGKV1-27*01 | A20(Y2) | X63398 | Gene ID: 28935 |
| IGKV1-33*01 | O18 | M64856 | Gene ID: 28933 |
| IGKV1D-8*01 | L24(Ve"; V13; Q3) | Z00008 | Gene ID: 28904 |
| IGKV1D-8*02 | — | KM455563 | |
| IGKV1D-8*03 | — | KM455567 | |
| IGKV1D-12*01 | L19(Vb") | X17263 | Gene ID: 28903 |
| IGKV1D-12*02 | L5/19a(V4b; Vb') | V01576 | |
| IGKV1D-13*01 | L18(Va") | X17262 | Gene ID: 28902 |
| IGKV1D-13*02 | — | KM455562 | |
| IGKV1D-16*01 | L15(HK166; Q13) | K01323 | Gene ID: 28901 |
| IGKV1D-16*02 | L15a(HK101) | V00558 | |

TABLE 1-continued

Example Kappa Variable Group Genes or Genetic Alleles.

| Allele names | Clone name | Accession numbers | NCBI Gene Designation |
|---|---|---|---|
| IGKV1D-17*01 | L14(Q4) | X63392 | Gene ID: 28900 |
| IGKV1D-22*01 | A9 | X71887 | Gene ID: 28899 |
| IGKV1D-27*01 | A4(A4a; V52) | Z00004 (M23848) | Gene ID: 28898 |
| IGKV1D-32*01 | O9 | X71896 | Gene ID: 28897 |
| IGKV1D-33*01 | O8 | M64855 | Gene ID: 28896 |
| IGKV1D-39*01 | O2 | X59312 | Gene ID: 28893 |
| IGKV1D-43*01 | L23(Q2) | X72817 | Gene ID: 28891 |
| IGKV2-24*01 | A23 | X12684 | Gene ID: 28923 |
| IGKV2-28*01 | A19(Q7) | X63397 | Gene ID: 28921 |
| IGKV2-30*01 | A17 | X63403 | Gene ID: 28919 |
| IGKV2-30*02 | — | FM164408 | |
| IGKV2-40*01 | O11 | X59314 | Gene ID: 28916 |
| IGKV2-40*02 | O11a(V3a) | X59317 | |
| IGKV2D-26*01 | cos142 | AP001216 | Gene ID: 28884 |
| IGKV2D-26*02 | DPK14 | Z27499 | |
| IGKV2D-26*03 | — | KM455565 | |
| IGKV2D-28*01 | A3 | X12691 | Gene ID: 28883 |
| IGKV2D-29*01 | A2(A2a) | M31952 | Gene ID: 28882 |
| IGKV2D-29*02 | A2c | U41644 | |
| IGKV2D-30*01 | A1 | X63402 | Gene ID: 28881 |
| IGKV2D-40*01 | O1 | X59311 | Gene ID: 28878 |
| IGKV3-11*01 | L6 | X01668 | Gene ID: 28914 |
| IGKV3-11*02 | Vg(kv3g) | K02768 | |
| IGKV3-15*01 | L2(Humkv328h5; Q11) | M23090 | Gene ID: 28913 |
| IGKV3-20*01 | A27 | X12686 | Gene ID: 28912 |
| IGKV3-20*02 | 13K18 | L37729 | |
| IGKV3D-7*01 | L25(V138; Q9) | X72820 | Gene ID: 28877 |
| IGKV3D-11*01 | L20(Vg"; kv3g") | X17264 | Gene ID: 28876 |
| IGKV3D-11*02 | — | KM455561 | |
| IGKV3D-11*03 | 3A7 | L19271 | |
| IGKV3D-20*01 | A11 | X12687 | Gene ID: 28874 |
| IGKV3D-20*02 | 3A9 | L19272 | |
| IGKV4-1*01 | B3 | Z00023 | Gene ID: 28908 |
| IGKV5-2*01 | B2(EV15) | X02485 | Gene ID: 28907 |

In certain example embodiments, the synthetic fibril is made or derived from one or more genes or genetic alleles encoding the immunoglobulin lambda variable group. These genes include, for example, IGLV1-36, IGLV1-40, IGLV1-44, IGLV1-47, IGLV1-51, IGLV1-62, IGLV2-5, IGLV2-8, IGLV2-11, IGLV2-14, IGLV2-18, IGLV2-23, IGLV3-1, IGLV3-10, IGLV3-12, IGLV3-16, IGLV3-19, IGLV3-21, IGLV3-25, IGLV3-27, IGLV4-3, IGLV4-60, IGLV4-69, IGLV5-37, IGLV5-39, IGLV5-45, IGLV5-52, IGLV6-57, IGLV7-43, IGLV9-49, IGLV10-54. Example lambda variable group genetic alleles that can be used in accordance with the methods provided herein are provided in Table 2, below.

TABLE 2

Example Lambda Variable Group Genes or Genetic Alleles.

| Allele names | Clone name | Accession numbers | NCBI Gene Designation |
|---|---|---|---|
| IGLV1-36*01 | 1a(1a.11.2) | Z73653 | Gene ID: 28826 |
| IGLV1-40*01 | Humlv1042 | M94116 | Gene ID: 28825 |
| IGLV1-40*02 | Vlambda1.2(IGLV1S2) | X53936 | |
| IGLV1-40*03 | DPL6 | Z22192 | |
| IGLV1-44*01 | 1c(1c.10.2) | Z73654 | Gene ID: 28823 |
| IGLV1-47*01 | 1g(1g.400B5) | Z73663 | Gene ID: 28822 |

TABLE 2-continued

Example Lambda Variable Group Genes or Genetic Alleles.

| Allele names | Clone name | Accession numbers | NCBI Gene Designation |
|---|---|---|---|
| IGLV1-47*02 | V1-17 | D87016 | |
| IGLV1-51*01 | 1b(1b.366F5) | Z73661 | Gene ID: 28820 |
| IGLV1-51*02 | Humlv117 | M30446 | |
| IGLV1-62*01 | V1-23P | D87022 | Gene ID: 28819 |
| IGLV2-5*01 | 2a1(2a1.51E6) | Z73641 | Gene ID: 28818 |
| IGLV2-5*02 | psiVlambdaII.1 | X57825 | |
| IGLV2-8*01 | 2c(2c.118D9) | X97462 | Gene ID: 28817 |
| IGLV2-8*02 | lv2046 | L27695 | |
| IGLV2-8*03 | RXL2046 | Y12418 | |
| IGLV2-11*01 | 2e(2e.2.2) | Z73657 | Gene ID: 28816 |
| IGLV2-11*02 | DPL12 | Z22198 | |
| IGLV2-11*03 | RXL12 | Y12415 | |
| IGLV2-14*01 | 2a2(2a2.272A12) | Z73664 | Gene ID: 28815 |
| IGLV2-14*02 | lv2018 | L27822 | |
| IGLV2-14*03 | EKL11 | Y12412 | |
| IGLV2-14*04 | RXL11 | Y12413 | |
| IGLV2-18*01 | 2d(2d.29D11) | Z73642 | Gene ID: 28814 |
| IGLV2-18*02 | lv216.21 | L27697 | |
| IGLV2-18*03 | lv2007 | L27694 | |
| IGLV2-18*04 | lv2113 | L27692 | |
| IGLV2-23*01 | Vlambda2.1(IGLV2S1) | X14616 | Gene ID: 28813 |
| IGLV2-23*02 | 2b2(2b2.400B5) | Z73665 | |
| IGLV2-23*03 | V1-7 | D86994 | |
| IGLV3-1*01 | VLIII.1 | X57826 | Gene ID: 28809 |
| IGLV3-10*01 | 3p(3p.81A4) | X97464 | Gene ID: 28803 |
| IGLV3-10*02 | IGGLL295 | L29166 | |
| IGLV3-12*01 | 3i(3i.2.2) | Z73658 | Gene ID: 28802 |
| IGLV3-12*02 | V2-8 | D86998 | |
| IGLV3-16*01 | 3a(3a.119B4) | X97471 | Gene ID: 28799 |
| IGLV3-19*01 | Vlambda3.1(IGLV3S1) | X56178 | Gene ID: 28797 |
| IGLV3-21*01 | IGLV3S2 | X71966 | Gene ID: 28796 |
| IGLV3-21*02 | V2-14 | D87007 | |
| IGLV3-21*03 | Humlv318 | M94115 | |
| IGLV3-25*01 | 3m(3m.102D1) | X97474 | Gene ID: 28793 |
| IGLV3-25*02 | V2-17 | D86994 | |
| IGLV3-25*03 | IGGLL150 | L29165 | |
| IGLV3-27*01 | V2-19 | D86994 | Gene ID: 28791 |
| IGLV4-3*01 | VlambdaN.2 | X57828 | Gene ID: 28786 |
| IGLV4-60*01 | 4a(4a.366F5) | Z73667 | Gene ID: 28785 |
| IGLV4-60*02 | V5-4 | D87000 | |
| IGLV4-60*03 | V5-4 | AF073885 | |
| IGLV4-69*01 | 4b(4b.68B6) | Z73648 | Gene ID: 28784 |
| IGLV4-69*02 | lv801 | U03868 | |
| IGLV5-37*01 | 5e(5e.366F5) | Z73672 | Gene ID: 28783 |
| IGLV5-39*01 | 5a(5a.366F5) | Z73668 | Gene ID: 28782 |
| IGLV5-39*02 | Vlambda5 | AF216776 | |
| IGLV5-45*01 | 5c(5c.366F5) | Z73670 | Gene ID: 28781 |
| IGLV5-45*02 | 5c(5c.400B5) | Z73671 | |
| IGLV5-45*03 | V4-2 | D86999 | |
| IGLV5-45*04 | — | KM455553 | |
| IGLV5-52*01 | 5b(5b.366F5) | Z73669 | Gene ID: 28779 |
| IGLV6-57*01 | 6a(6a.366F5) | Z73673 | Gene ID: 28778 |
| IGLV6-57*02 | — | KM455556 | |
| IGLV7-43*01 | Vlambda7.1 | X14614 | Gene ID: 28776 |
| IGLV9-49*01 | 9a(9a.366F5) | Z73675 | Gene ID: 28773 |
| IGLV9-49*02 | V5-2 | D87016 | |
| IGLV9-49*03 | lv901e | U03869 | |
| IGLV10-54*01 | 10a(10a.872F9) | Z73676 | Gene ID: 28772 |
| IGLV10-54*02 | V1-20 | D86996 | |
| IGLV10-54*03 | gVlambdaX-4.4 | S70116 | |

In certain example embodiments, the synthetic fibrils including light chain variable domain precursor monomers can be made using combinations of kappa or lambda protein made or derived from one or more genes or genetic alleles identified in Tables 1 and 2.

While light chain variable domain proteins may be preferable, in certain example embodiments the methods and systems described herein can use fibrils generated from constant domain fragments that form amyloid fibrils (see e.g., Solomon, A., Weiss, D. T., Murphy, C. L., Hrncic, R., Wall, J. S. and Schell, M. (1998) Light chain-associated amyloid deposits comprised of a novel κ constant domain. Proc. Natl. Acad. Sci., 95: 9547-9551, which is expressly incorporated herein by reference in its entirety). Such genes may include IGKC, IGLC2, IGLC3, or IGLC7 or combinations thereof. In certain example embodiments, the fibrils may include engineered combinations of light chain variable domains and constant domains that form amyloids. Example constant region genetic alleles that can be used in accordance with the methods provided herein are provided in Table 3, below.

TABLE 3

Example Constant Region Genes or Genetic Alleles.

| Allele names | Clone name | Accession numbers | NCBI Gene Designation |
|---|---|---|---|
| IGKC*01 | Inv3 | J00241 | Gene ID: 3514 |
| IGKC*02 | geV-4 | M11736 | |
| IGKC*03 | geV-3 | M11737 | |
| IGKC*04 | — | AF017732 | |
| IGKC*05 | — | AF113887 | |
| IGLC2*01 | — | J00253 | Gene ID: 3538 |
| IGLC2*02 | — | X06875 | |
| IGLC2*03 | — | AJ491317 | |
| IGLC3*01 | — | J00254 | Gene ID: 3539 |
| IGLC3*02 | — | K01326 | |
| IGLC3*03 | — | X06876 | |
| IGLC3*04 | — | D87017 | |
| IGLC7*01 | — | X51755 | Gene ID: 28834 |
| IGLC7*02 | — | M61771 | |
| IGLC7*03 | — | KM455557 | |

While light chain variable domain proteins can be used, in certain example embodiments the methods and systems described herein can use fibrils generated from constant domain fragments that form amyloids (see e.g., Solomon, A., Weiss, D. T., Murphy, C. L., Hrncic, R., Wall, J. S. and Schell, M. (1998) Light chain-associated amyloid deposits comprised of a novel κ constant domain. Proc. Natl. Acad. Sci., 95: 9547-9551, which is expressly incorporated herein by reference in its entirety). Such genes and genetic alleles can include, for example, IGKC, IGLC2, IGLC3, or IGLC7 or combinations thereof. In certain example embodiments, the fibrils can include engineered combinations of light chain variable domains and constant domains that form amyloids. In certain example embodiments, such engineered fibrils, including light chain variable domain precursor monomers and constant region precursor monomers, can be made using combinations of protein made or derived from one or more genes or genetic alleles identified in Tables 1, 2, and 3.

In certain example embodiments, the fibrils can be made from rVλ6Wil fibril precursor monomers, thereby forming rVλ6Wil fibrils (see Wall, J. S., Schell, M., Murphy, C., Hrncic, R., Stevens, F. and Solomon, A. (1999) *Thermodynamic Instability of Human λ6 Light Chains: Correlation with Fibrillogenicity*. Biochemistry, 38, (42), 14101-14108; and, Martin E B, Williams A, Wooliver C, Heidel R E, Adams S, Dunlap J, et al., *Differential recruitment efficacy of patient-derived amyloidogenic and myeloma light chain proteins by synthetic fibrils—A metric for predicting amyloid propensity*. PLoS ONE 12(3): e0174152 (2017), both of which are expressly incorporated herein by reference in their entirety). The rVλ6Wil precursor monomer is produced as a recombinant protein and isolated from *E. coli*. When dissolved at 1 mg/mL in phosphate buffered saline, pH 7.5 and shaken at room temperature, fibrils form within 12 hours, and the reaction is complete (i.e., there is no monomer left in solution) after ~72 h of shaking. The resultant amyloid fibrils can be seen as "clumps" of linear fibril aggregates by electron microscopy. Additionally, the fibril aggregates bind the dye thioflavin T and emit fluorescence at 490 nm (when excited at 450 nm), characteristic of amyloid fibrils. In certain example embodiments, the rVλ6Wil precursor monomers used to form the synthetic fibrils described herein can have an amino acid sequence that is about 60, 65, 70, 75, 80, 85, 90, 91, 92, 93, 94, 95, 96, 97, 98% or more identical to the sequence set forth as SEQ ID NO: 1. In certain example embodiments, the fibrils can be made from rVλ6Jto fibril precursor monomers, thereby forming rVλ6Jto fibrils. In certain example embodiments, the rVλ6Jto precursor monomers used to form the synthetic fibrils described herein can have an amino acid sequence that is about 60, 65, 70, 75, 80, 85, 90, 91, 92, 93, 94, 95, 96, 97, 98% or more identical to the sequence set forth as SEQ ID NO: 2.

Direct Labeling Assay

In certain example embodiments, provided is a direct labeling assay for identifying amyloidogenic immunoglobulin light chain proteins from a biological sample. The direct labeling assay can also be used, for example, to assess the amyloidogenic risk to a subject. The method includes, for example, obtaining a biological sample from a subject, such as a subject that may be in a high-risk group for developing amyloidosis. As noted previously, the subject can be any subject, for example, that has been diagnosed with—or that is suspected of having—an amyloid precursor disease such as monoclonal gammopathy of unknown significance, smoldering myeloma, or multiple myeloma. Such amyloid precursor diseases, which are considered non-amyloid diseases, are unfortunately known to progress to the amyloid phenotype in which the subject develops amyloid plaques in one or more organs or tissues. In certain example embodiments, the subject can be a healthy subject that, nevertheless, desires to be screened for an amyloid precursor disease. For example, the subject may have a family history of amyloid precursor diseases and/or amyloidosis and thus desire to be screened for amyloidogenic protein. In other example embodiments, the subject may have received a diagnosis of amyloidosis.

The sample collected from the subject can be any type of biological sample that is generally known in the art to contain immunoglobulin light chain proteins. For example, the sample can be a blood sample, plasma sample, serum sample, urine sample, or any other bodily fluid from which immunoglobulin light chain proteins can be isolated. The sample can be collected by conventional methods, such as a blood draw, free urine catch, or tissue biopsy in which immunoglobulin light chain proteins are present. In certain example embodiments, one or more biological samples can be combined.

In certain example embodiments, the direct binding assay includes providing detectably-labeled immunoglobulin light chain proteins from the biological sample. That is, to assess the presence of amyloidogenic immunoglobulin light chain proteins in the biological sample, in certain example embodiments the immunoglobulin light chain proteins can be isolated or enriched from the biological sample of the subject. The isolated immunoglobulin light chains can then be labeled such that the presence of the immunoglobulin light chain proteins in a reaction mixture can be detected.

The immunoglobulin light chain proteins can be isolated or enriched from the biological sample using any conventional techniques known to those of skill in the art. For example, the light chain proteins can be isolated or enriched using affinity chromatography with light chain reactive antibodies. Additionally or alternatively, the light chain proteins from the biological sample can be isolated or enriched using protein L-conjugated beads that specifically bind light chain proteins. Additionally or alternatively, light chain proteins from the biological sample can be isolated or enriched by size exclusion chromatography, which can be performed with or without prior depletion of other proteins such as albumin. (see Lavatelli F, Brambilla F, Valentini V, Rognoni P, Casarini S, Di Silvestre D, et al. (2011), *A novel approach for the purification and proteomic analysis of pathogenic immunoglobulin free light chains from serum*. Biochim Biophys Acta, 1814, (3), 409-19; and Chen Y, Lin S, Yeh Y, Hsiao H, Wu C, Chen S and Wang A. (2005), *A modified protein precipitation procedure for efficient removal of albumin from serum*. Electrophoresis, 26, 2117-2127, both of which are expressly incorporated herein by reference in their entirety). In certain example embodiments, the biological sample can be processed to remove interfering proteins such as serum albumin.

In addition to isolating or enriching the immunoglobulin light chain proteins from the sample, the immunoglobulin light chain proteins can be labeled with a detectable label, thus providing the detectably-labeled immunoglobulin light chain proteins as described herein. Any means known in the art for detectably labeling a protein can be used and/or adapted for use with the methods described herein. For example, the isolated immunoglobulin light chain proteins can be radiolabeled with a radioisotope, or labeled with a fluorescent tag or a chemiluminescent tag. Example radioisotopes include, for example, $^{18}$F, $^{111}$In, $^{99m}$Tc, and $^{123}$I, and $^{125}$I. These and other radioisotopes can be attached to the isolated immunoglobulin light chain using well known chemistry that may or not involve the use of a chelating agent, such as DTPA or DOTA covalently linked to the light chain protein. Example fluorescent or chemiluminescent tags include fluorescein, Texas red, rhodamine, Alexa dyes, and luciferase that can be conjugated to the protein by reaction with lysine, cysteine, glutamic acid and aspartic acid side chains. In one example embodiment, the label is detected using a fluorescent microplate reader, or fluorimeter, using the excitation and emission wavelengths appropriate for the tag that is used. Radioactive labels can be detected, for example, using a gamma or scintillation counter depending on the type of radioactive emission and by using energy windows suitable for the accurate detection of the specific radionuclide. However, any other suitable technique for detection of radioisotopes can also be used to detect the label.

Following labeling of the immunoglobulin light chain proteins, the detectably-labeled immunoglobulin light chain proteins can be brought in to contact with synthetic fibrils to form a reaction mixture. That is, the detectably-labeled immunoglobulin light chain proteins from the biological sample can be incubated with synthetic fibrils to form the reaction mixture. The fibrils can be any type of fibril described herein. In certain example embodiments, the fibrils for a given direct labeling assay can be all the same type of fibrils. For example, the fibrils that are used to contact the detectably-labeled immunoglobulin light chain proteins can all be rVλ6Wil fibrils. In certain example embodiments, the reaction mixture can be incubated for about 1, 2, 3, 4, 5, 7, 9, 12, 15, 18, 24, 30, or 36 hours. Further, in certain example embodiments the reaction mixture can be incubated at a temperature of approximately 10 to 60° C., such as above 5, 10, 15, 20, 25, 30, 35, 40, 45, 50, 55, 60, or 65° C. Other well-known components can also be added to the reaction mixture, such as buffers, chelators, etc. that help to stabilize the reaction mixture. For example, phosphate e or other buffering salts, or sodium azide (as a preservative), or detergent such as Tween™ 20, can be used to prevent non-specific interactions and can be included in the reaction mixture.

Figure 4:
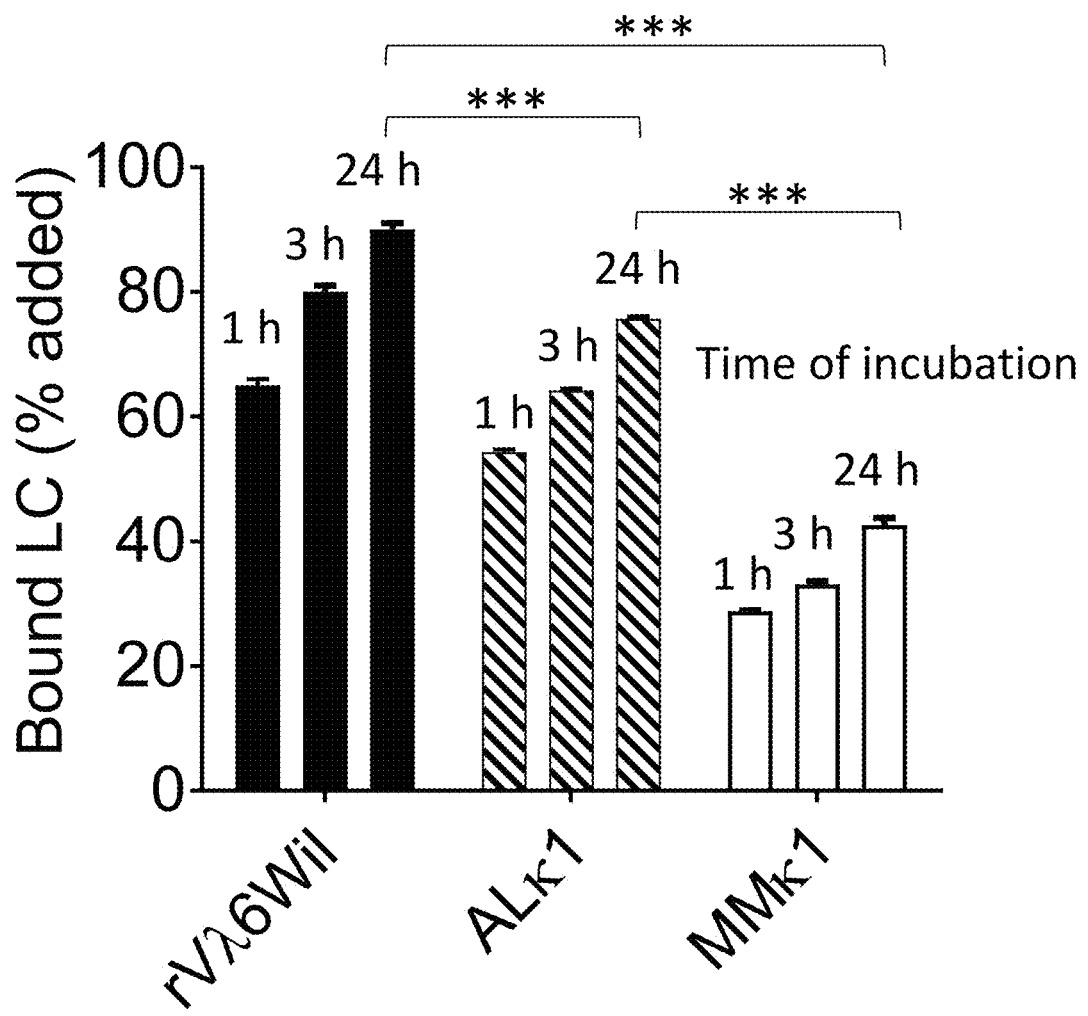
FIG. 4 is a graph showing the results of a pulldown assay of $^{125}$I-labeled rVλ6Wil (black), AL-LC (AL1κ—hashed) and MM-LC (MM1κ—white) using synthetic rVλ6Wil fibrils as the substrate, in accordance with certain example embodiments. Samples of fibrils were incubated with the radioactive proteins for 1 h, 3 h, or 24 h. At each time point, the recruitment efficacy was Wil>AL-LC>MM-LC. ***p<0.0005. The assay was able to discern the AL and MM LC protein with statistical significance based on recruitment efficacy.

By contacting the detectably-labeled immunoglobulin light chain proteins with the synthetic fibrils, the detectably-labeled immunoglobulin light chain proteins can bind the fibrils. For example, an immunoglobulin light chain protein can bind to the end of the fibril (see FIG. 6). Without wishing to be bound by any particular theory, it is believed that the greater the affinity that the subject's immunoglobulin light chain proteins have for the synthetic fibrils in vitro, the greater the amount of binding to the fibrils—and hence the greater the amyloidogenic nature of the immunoglobulin light chain proteins from the biological sample. As illustrated in FIG. 4, for example, and consistent with the detailed examples provided herein, light chain protein from an AL amyloid subject has a greater affinity for the fibrils as compared to a non-amyloidogenic multiple myeloma (MM) immunoglobulin light chain protein. That is, immunoglobulin light chain proteins with a propensity to form amyloid bind with a greater affinity, or in greater amounts, to the fibrils than do immunoglobulin light chain proteins with a low propensity to form amyloid.

To identify amyloidogenic proteins from the biological sample via the direct binding assay, and following any incubation of the reaction mixture, the reaction mixture is washed to remove any unbound, detectably labeled immunoglobulin light chains. The washing step can be performed, for example, using any conventional wash buffer. For example, the sample can be centrifuged for about 2, 3, 4, 5, 6, 7, or 8 min at about 10,000-20,000×g, such as about 15,000×g, and the supernatant removed. The fibril pellet can then by re-suspended in a neutrally buffered solution, such as phosphate buffered saline (PBS) or Tris buffered saline (TBS), with or without a detergent, at a pH of about 7-8, such as about 7.5. For example, Tween™ 20 may be added to the mixture, as may other detergents such as Triton-X100. The sample can then be centrifuged again for 2, 3, 4, 5, 6, 7, or 8 mins, for example, and the supernatant again removed and pooled with the previous supernatant sample. A signal can then be detected from the reaction mixture, the signal originating from the detectable labels. Because the detectable labels are bound to the isolated or enriched immunoglobulin light chains from the biological sample, the level of binding of the immunoglobulin light chains to the fibrils is believed to be proportional to the intensity of the signal obtained from the reaction mixture. That is, the greater the signal intensity of the detected signal from the reaction mixture of the direct binding assay, the greater the recruitment of the detectably-labeled immunoglobulin light chains from the biological sample to the fibrils.

In certain example embodiments, the level of binding of the detectably-labeled immunoglobulin light chain proteins with the synthetic fibrils, as determined from the intensity of the signal generated from the labels, can be used to assess the amyloidogenic propensity of the immunoglobulin light chain proteins in the sample (and hence provide an indication of the amyloidogenic risk to the subject). For example, non-amyloidogenic immunoglobulin light chain proteins can be labeled as described herein and then incubated with a synthetic fibril mixture to form a non-amyloidogenic reaction mixture. The signal intensity generated by the detectably-labeled non-amyloidogenic immunoglobulin light chain proteins of the non-amyloidogenic reaction mixture, for example, can serve as a control or baseline level of binding. In certain example embodiments, immunoglobulin light chain proteins from a multiple myeloma subject can be used as the non-amyloidogenic control (see, e.g., white bars of FIG. 4).

In certain example embodiments, by comparing the relative signal intensities between the non-amyloidogenic reaction mixture (negative control) and a reaction mixture generated from the biological sample, the relative affinity of the immunoglobulin light chain proteins for the fibrils can be assessed. A sample signal intensity higher than the non-amyloidogenic reaction mixture signal intensity, for example, indicates that the immunoglobulin light chain proteins bind the fibrils at a relatively high level (a higher affinity), thus indicating an increased propensity for the immunoglobulin light chain proteins to be amyloidogenic. Conversely, a sample signal intensity at or below the signal intensity of the non-amyloidogenic reaction mixture, for example, indicates that the immunoglobulin light chain proteins are less likely to be amyloidogenic.

In certain example embodiments, the signal intensity determined from the reaction mixture is used to determine a signal intensity value for the reaction mixture. The signal intensity value is determined, for example, by normalizing the signal intensity of the reaction mixture of the direct binding assay to maximum signal intensity (as a positive control) for the direct binding assay. As those skilled in the art will appreciate, the positive control can be performed in conjunction with the assay of the biological sample, such as on the same well-plate as the assay of the biological sample.

For the control, fibril precursor monomers can be detectably-labeled as described herein with the same label as the isolated or enriched immunoglobulin light chain proteins (i.e., with a radioisotope, a fluorescent tag, or a chemiluminescent tag, for example). Further, the fibril precursor monomers can be of the same type used to generate the fibrils of the reaction mixture (so as to maintain the assay as a control). The detectably-labeled fibril precursor monomers can then be contacted with the fibrils to form a control reaction mixture—the control reaction mixture allowing a maximum binding of the detectably-labeled fibril precursor monomers to the fibrils. For example, the synthetic fibrils can be saturated with the detectably-labeled fibril precursor monomers so that complete binding/saturation of the fibrils can occur with the detectably-labeled fibril precursor monomers. That is, the detectably-labeled precursor monomers can be expected to maximally bind the fibril, thus allowing a saturation intensity level to be determined for a given time period.

In certain example embodiments, diluted serum can be added to the control reaction mixture. The serum, for example, can act to mimic any dilution of the biological sample when generating the positive control sample, as any percentage dilution of the biological sample should be matched with dilution of the positive control to preserve the "control" as aspect of the positive control. For example, about 1, 2, 3, 4, 5, 6, 7, 8, 9, 10, 11, 12, 13, 14, or 15% serum can be added to the control reaction mixture. Following a wash step to remove any unbound detectably-labeled fibril precursor monomers from the control reaction mixture, a control signal can be detected from the control reaction mixture via the detectable labels. A determined control signal intensity from the control signal, for example, can correspond to the maximum signal intensity.

To determine the signal intensity value of the biological sample, the signal intensity of the reaction mixture for the biological sample is compared to the maximum signal intensity. For example, the signal intensity value is determined as a fraction of the signal intensity of the reaction mixture for the biological sample relative to the maximum signal intensity. If for a given assay, for example, using a radioactive detectable label, the signal intensity of the biological sample reaction mixture is 32,365 cpm while the maximum signal intensity is 98,236 cpm, then the signal intensity value of the biological sample reaction mixture can be determined as 32,365 cpm/98,236 cpm, i.e., about 0.33 or 33%. In another example, if the maximum signal intensity is 99,136 cpm and the biological sample reaction mixture is 72,964, then the signal intensity value of the biological sample reaction mixture is about 0.74 of 74%. As those skilled in the art will appreciate, the variety of different labels that are compatible with the methods described herein will yield signal intensities with different units, but the signal intensity value—as determined as a fraction of the maximum signal intensity—corresponds to a normalized signal intensity for the signal intensity of the biological sample reaction mixture (relative to a maximum signal intensity).

In certain example embodiments, the signal intensity value is compared to a threshold value, such as to determine whether the biological sample includes amyloidogenic proteins. That is, the signal intensity value is compared to a threshold value to identify amyloidogenic proteins in the biological sample of the subject. A subject can also be placed into an appropriate risk group for developing amyloid by comparing a subject's signal intensity value to a threshold value. As described herein, because the signal intensity of the biological sample reaction mixture is indicative of the level of binding the immunoglobulin light chain proteins of the biological sample to the fibrils in vitro, the higher the signal intensity value the greater the propensity for the immunoglobulin light chain proteins in the biological sample to be amyloidogenic. Hence, for the direct binding assay, the threshold value is a number above which the immunoglobulin light chain proteins of the biological sample can be deemed amyloidogenic. Below the threshold value, the immunoglobulin light chain proteins of the biological sample can be deemed less amyloidogenic or non-amyloidogenic. Thus, comparison to the threshold values provides an indication of risk to the subject.

In certain example embodiments, the threshold value can be an assigned value of 30% or greater of the maximum signal intensity, such as about 35, 40, 45, 50, 55, 60, 65, 70, 75, 80, 85, or 90%. For example, if the threshold value assigned to the assay is about 40%, and the signal intensity value is 63%, the immunoglobulin light chain proteins of the biological sample can be identified as amyloidogenic. In certain example embodiments, the threshold value can be a value below which the immunoglobulin light chain proteins can be deemed to be non-amyloidogenic (or less amyloidogenic). For example, if the signal intensity value falls below a threshold value of about 50, 45, 40, 35, 30, 25, or 20% or less (of the maximum signal intensity), the immunoglobulin light chain proteins in the sample can be identified as non-amyloidogenic (or less amyloidogenic).

Additionally or alternatively, in certain example embodiments the threshold value can be determined empirically using known amyloidogenic or non-amyloidogenic biological samples. For example, the direct binding assay as described herein can be performed using immunoglobulin light chain proteins that are known to be amyloidogenic or non-amyloidogenic, with the results being used to determine one or more threshold values. While such amyloidogenic or non-amyloidogenic immunoglobulin light chain proteins can be obtained in a variety of ways, in certain example embodiments the immunoglobulin light chain proteins can be isolated or enriched from one or more biological samples of subjects having a known amyloidogenic or non-amyloidogenic phenotype. For example, the subject may be known, via biopsies or other diagnostic indicators, as suffering from amyloidosis or as having an amyloid precursor disease such as MGUS, smoldering multiple myeloma, or multiple myeloma. Light chain immunoglobulin proteins from a biological sample of the subject can then be isolated or enriched as described herein. In other example embodiments, known amyloidogenic or non-amyloidogenic proteins may be obtained in vitro via gene expression techniques known in the art, for example by cloning the patient light chain protein sequence from, e.g., bloodborne plasma cells, and expressing it in a bacteria or host cell expression system.

Once the known amyloidogenic or non-amyloidogenic immunoglobulin light chain proteins are obtained, the immunoglobulin light chain proteins can be labeled with a detectable label as described herein. They can then be contacted with synthetic fibrils as described herein in accordance with the direct binding assay. The detectably-labeled, isolated or enriched immunoglobulin light chain proteins and the fibrils form a threshold reaction mixture, from which a threshold signal intensity can be determined. The threshold signal intensity can then be converted to a threshold value by comparing, for each of the one or more sample types, the threshold signal intensity to a maximum signal intensity (i.e., comparing to a positive control signal intensity as described herein). For example, a non-amyloidogenic sample may have a threshold signal intensity of 44,315 cpm, whereas the maximum signal intensity may be 99,103 cpm—thus resulting in a threshold value of 44,315 cpm/99,103 cpm (i.e., about 0.44 or 44%) for the non-amyloidogenic sample. In another example, an amyloid biological sample, such as from an amyloid subject, may have a threshold signal intensity of 66,327 cpm, whereas the maximum signal intensity may be 98,912 cpm—thus resulting in a threshold value of 66,327 cpm/98,912 cpm (i.e., about 0.67 or 67%) for the amyloidogenic sample. In certain example embodiments, the assessment of known samples can be repeated for multiple samples in order to arrive at an average or median value that represents the threshold value. For example, multiple amyloid samples can be assayed with the direct binding assay to determine an amyloid threshold value that is an average or median value.

By determining threshold values based on known sample types as described herein, the threshold values can be used to identify immunoglobulin light chain proteins in a biological sample of a subject as amyloidogenic or non-amyloidogenic. For example, a reaction mixture from a biological sample of a subject with a signal intensity value above the determined threshold value can be deemed amyloidogenic, whereas a biological sample from a subject having a signal intensity value below the determined threshold value can be deemed non-amyloidogenic. If the determined threshold value for a non-amyloidogenic sample is 44%, for example, a biological sample from a subject having a signal intensity value of 55% can be identified as amyloidogenic. Conversely, a biological sample from a subject having a signal intensity value of 38% (i.e., below the determined threshold value of 44%) can be identified as non-amyloidogenic. In certain example embodiments, the threshold values determined from known amyloidogenic or non-amyloidogenic sample types can be about 35, 40, 45, 50, 55, 60, 65, or 70%.

In certain example embodiments, the threshold values described herein can be used to define various risk groups for developing amyloid. For example, the threshold value for the direct binding assay can be assigned at varying levels (percentages of a maximum intensity) depending on the risk to the subject of developing amyloid. In such example embodiments, a lower threshold value corresponds to a lower risk level and a higher threshold value corresponds to a higher risk. For example, a threshold value corresponding to lower risk group can be less than about 30%, whereas a medium risk group may be about 30% to 55%. A high-risk group, for example, can correspond to threshold value above about 50-60%. Continuing with this example, a subject whose biological sample yields a signal intensity value of 22% in the direct binding assay, for example, can be categorized as having a low risk of developing amyloid. Further, for a subject whose biological sample yields a signal intensity value of 45%, for example, can be advised that he or she is at moderate risk (or even as being borderline amyloidogenic). A subject whose biological sample yields a signal intensity value of 63% in the direct binding assay, for example, can be placed in the high-risk amyloidogenic group (or even as having amyloidosis) and treated accordingly.

In certain example embodiments, the assigned threshold values for the risk groups can be determined based on the use of known amyloidogenic or non-amyloidogenic samples as described herein. That is, the threshold values generated using the known amyloidogenic or non-amyloidogenic sample types in the direct binding assay can be used to establish the risk groups. For example, if the threshold value determined for a non-amyloidogenic sample is 50%, a subject whose biological sample yields a signal intensity value of 68% can be deemed at high risk for developing amyloid. Conversely, if a biological sample of a subject has a signal intensity value of 33%—i.e., below the threshold value determined for the non-amyloidogenic sample—the subject can be identified as low risk for developing amyloid. A subject whose biological sample yields a signal intensity value of 50% may be deemed at moderate risk for developing amyloid.

While the above threshold values and ranges are examples, one skilled in the art will appreciate based on this disclosure that such threshold values and ranges can be adjusted, expanded, narrowed, or otherwise changed in order to identify the risk of amyloidosis in a subject using the direct binding assay. Additionally or alternatively, other scales or ranges can be developed for identifying amyloidogenic immunoglobulin light chain proteins and assessing amyloidogenic propensity. For example, the threshold value may be a score or range, such as a range from 1-10, with 1 being low risk (and a signal intensity from the reaction mixture that falls well below the maximum signal intensity) and 10 being high risk (with a very high signal intensity of the second reaction mixture). A biological sample from a subject can then be evaluated to see where the subject falls on the scale, and appropriate amyloid treatment can be initiated as needed.

Competition Assay

While labeling isolated or enriched immunoglobulin light chain proteins as part of the direct binding assay may be practical in many settings, in other settings it may be desirable and more cost effective to assess the amyloidogenic nature of immunoglobulin light chain proteins in a sample without first isolating or enriching the immunoglobulin light chain proteins. Thus, in certain example embodiments, provided is a competition-based assay for identification of immunoglobulin light chain proteins from a biological sample of a subject that does not rely on isolation or enrichment of immunoglobulin light chains. The competition assay can, however, be used with sample preparations in which immunoglobulin light chain proteins have been enriched or isolated from a biological sample.

For the competition assay, a biological sample is obtained from a subject. As with the direct binding assay, the subject can be any type of subject described herein, such as a healthy subject, a subject having an amyloid precursor disease, or a subject "at risk" for developing amyloidosis. Further, the biological sample collected from the subject can be any type of biological sample that is generally known in the art to contain immunoglobulin light chain proteins. The sample can also be collected by any means known in the art, including those previously described herein. In certain example embodiments, one or more biological samples can be combined. In certain example embodiments, such as with the competition assay, the biological sample can be a serum sample, such as raw serum or serum that has been diluted to about 2, 5, 10, 15, 20, 25, 30, 35, 40, 45, 50, 55, 60, 65, 70, 75, or 80% of its original concentration.

In certain example embodiments, and as noted above, the biological sample can be processed in such a way that immunoglobulin light chain proteins located in the sample are isolated or enriched. In other example embodiments, the biological sample can be processed to remove interfering proteins such as serum albumin. In other example embodiments, the immunoglobulin light chain proteins can be isolated or enriched as described herein. In such embodiments, enriching or isolating the immunoglobulin light chain proteins can enhance or improve the detection of immunoglobulin light chain proteins in the sample that are amyloidogenic.

For the competition assay, in certain example embodiments fibril precursor monomers can be detectably labeled. That is, any of the fibril precursor monomers described herein that can form the synthetic fibrils can be detectably labeled for use with the competition assay. Any means known in the art for detectably labeling a protein can be used and/or adapted for use with the methods described herein. For example, the fibril precursor monomers can be radiolabeled with a radioisotope or labeled with a fluorescent tag or a chemiluminescent tag. Example radioisotopes include, for example, $^{18}F$, $^{111}In$, $^{99m}Tc$, $^{123}I$, and $^{125}I$. These and other radioisotopes can be attached to the isolated immunoglobulin light chain using well known chemistry that may or may not involve the use of a chelating agent, such as diethylenetriaminepentaacetic acid (DTPA) or 1,4,7,10-tetraazacyclododecane-1,4,7,10-tetraacetic acid (DOTA) linked to the light chain protein. Example fluorescent or chemiluminescent tags include fluorescein, Texas red, rhodamine, Alexa dyes, and luciferase that can be conjugated to the protein by reaction with lysine cysteine, glutamic acid and aspartic acid side chains. In one example embodiment, the label is detected using a fluorescent microplate reader, or fluorimeter, using the excitation and emission wavelengths appropriate for the tag that is used. Radioactive labels can be detected using a gamma or scintillation counter depending on the type of radioactive emission and by using energy windows suitable for the accurate detection of the specific radionuclide. However, any other suitable technique for detection of radioisotopes can also be used to detect the label.

Following labeling of the fibril precursor monomers, the detectably-labeled fibril precursor monomers can be brought into contact with the biological sample to form a reaction mixture. That is, the detectably-labeled fibril precursor monomers and biological sample can be mixed together to form the reaction mixture. In certain example embodiments where the immunoglobulin light chains are enriched or isolated from the biological sample, the biological sample comprising the isolated or enriched immunoglobulin light chains can be mixed with the detectably-labeled fibril precursor monomers to form the reaction mixture. As those skilled in the art will appreciate, other well-known components can be added to the reaction mixture, such as buffers, chelators, etc. that help to stabilize the reaction mixture. For example, phosphate or other buffering salts, or sodium azide (as a preservative), or detergents such as Tween™ 20 or Triton-X100 to prevent non-specific interactions can be included in the reaction mixture.

In certain example embodiments, the reaction mixture can then be contacted with synthetic amyloid fibrils to form a second reaction mixture. That is, the first reaction mixture, which includes the detectably-labeled fibril precursor monomers and biological sample, can be incubated with synthetic amyloid fibrils to form the second reaction mixture of the competition assay. The synthetic fibrils of the second reaction mixture can be any type of synthetic fibril as described herein. In certain example embodiments, the fibrils for a given competition assay can be all the same type of fibrils. For example, the synthetic fibrils that can be used to form the second reaction mixture can all be rVλ6Wil fibrils. Further, in certain example embodiments the detectably-labeled fibril precursor monomers can be of the same type as the monomers used to make the synthetic fibrils. That is, the synthetic fibrils incubated with the reaction mixture can be the polymeric form of the labeled fibril precursor monomers (but in an unlabeled form). For example, if the synthetic fibrils to be used in the competition assay are rVλ6Wil fibrils, rVλ6Wil precursor monomers can be detectably labeled and mixed with the biological sample to form the reaction mixture. The detectably-labeled rVλ6Wil fibril monomers/biological sample reaction mixture can then be incubated with rVλ6Wil fibrils to form the second reaction mixture. In certain example embodiments, the synthetic fibril precursor monomer can be different than the precursor monomers that comprise the polymer of the fibril.

In certain example embodiments, the second reaction mixture, which includes the detectably-labeled, fibril monomers, and biological sample, can be incubated for about 1, 2, 3, 4, 5, 7, 9, 12, 15, 18, 24, 30, or 36 hours. Further, in certain example embodiments the reaction mixture can be incubated at a temperature of 10° C.-60° C., such as above 5, 10, 15, 20, 25, 30, 35, 40, 45, 50, 55, 60, or 65° C. In certain example embodiments, other well-known components can be added to the second reaction mixture, such as buffers, chelators, etc. that help to stabilize the reaction mixture including phosphate or other buffering salts, or sodium azide (as a preservative), or detergents such as Tween™ 20, to prevent non-specific interactions.

Figure 11:
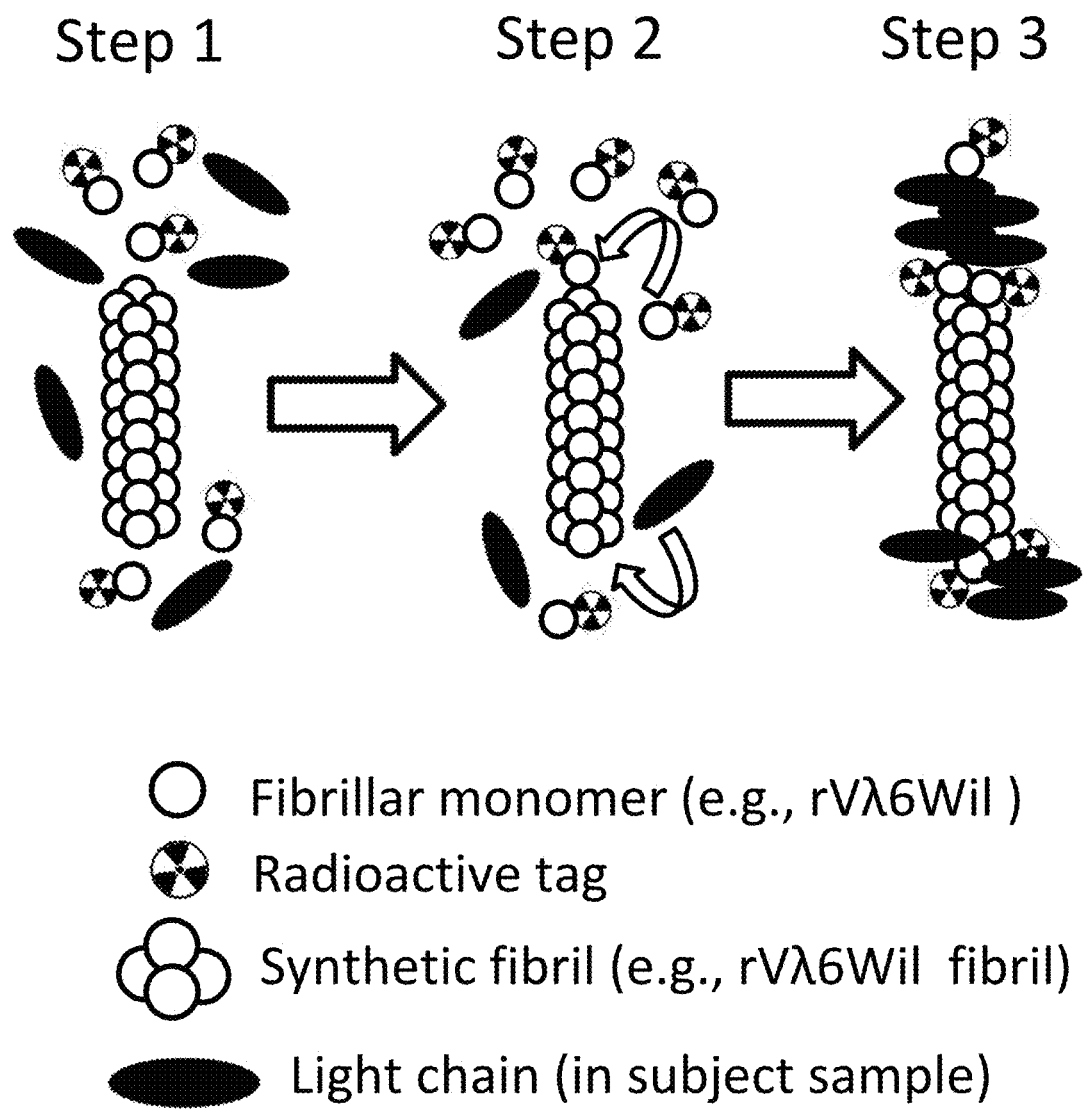
FIG. 11 is a schematic illustration of the competition assay described in FIG. 10, in accordance with certain example embodiments. This assay can be used to screen a biological sample from a patient for the presence of an amyloid-competent LC as compared to non-amyloidogenic MM LC.
Figure 12:
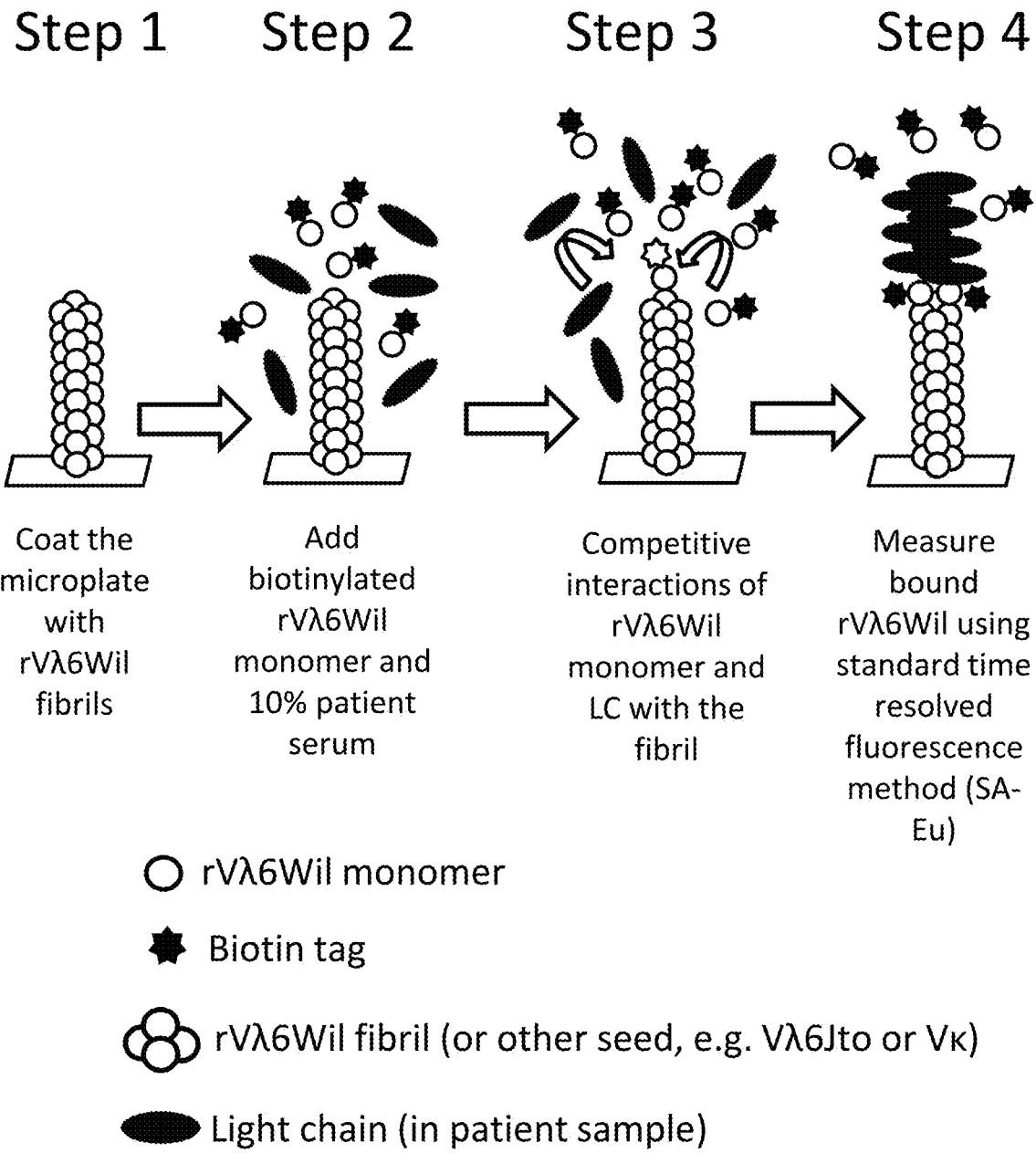
FIG. 12 is a schematic illustration of the second version of the competition assay, in accordance with certain example embodiments. In this assay, the competition is performed using biotinylated rVλ6Wil monomer and synthetic rVλ6Wil fibrils that are dried or otherwise complexed onto the wells of a 96-well microplate. The competition binding reaction is performed in the presence of 1000× molar excess of LC protein.

Without wishing to be bound by any particular theory, it is believed that immunoglobulin light chain proteins in the biological sample compete with the detectably-labeled fibril precursor monomers in the second reaction mixture for binding to the fibrils. Hence, the more affinity a given immunoglobulin light chain protein has for the synthetic fibril, the more likely it is that the immunoglobulin light chain protein will bind the fibril. Such a competition is illustrated, for example, in FIG. 11 and FIG. 12. As shown, immunoglobulin light chain proteins can, depending on the affinity of the immunoglobulin light chain proteins for the fibril, out-compete the detectably-labeled fibril precursor monomers for binding to the fibrils (FIG. 11 and FIG. 12). As shown in FIG. 12, in certain example embodiments the fibrils can be attached to a solid substrate, such as a microplate or well of a reaction chamber. The fibrils can be attached by any methods known in the art. For example, the fibrils can be dried on to the wells of a 96 well microplate by incubating the plate at 37° C. overnight. Alternatively, the fibrils may be coated onto the surface of the microplate wells by incubating a suspension of fibrils at 4° C., covered, overnight.

To identify amyloidogenic proteins from the biological sample via the competition assay, and following any incubation of the second reaction mixture, the second reaction mixture is washed to remove any unbound, detectably-labeled fibril precursor monomers. The washing step can be performed, for example, using any conventional wash buffer. For example, a solution of PBS or TBS containing 0.1% bovine serum albumin and 0.05% Tween™ 20 detergent. When the synthetic fibrils are attached to a plate or well of a reaction chamber, for example, washing can occur by inverting the plate over paper towels and tapping to remove the second reaction mixture solution. Wash buffer is then added to the wells and the wash solution removed again by inversion and tapping. A signal can then be detected from the second reaction mixture, the signal originating from the detectable labels of the detectably-labeled fibril precursor monomers (see FIG. 11 and FIG. 12).

Because the detectable labels are bound to the fibril precursor monomers as described herein, the level of binding of the fibril precursor monomers is believed to be proportional to the intensity of the signal obtained from the second reaction mixture. That is, the greater the signal intensity of the detected signal from the second reaction mixture of the direct binding assay, the greater the binding of the detectably-labeled fibril precursor monomers to the fibrils. But because amyloidogenic immunoglobulin light chain proteins from the biological sample compete with the detectably-labeled fibril precursor monomers for binding to the synthetic fibrils, amyloidogenic immunoglobulin light chain proteins in the biological sample act to reduce the signal intensity of the second reaction mixture. Hence, a lower signal intensity from the second reaction mixture indicates an increased level of amyloidogenic immunoglobulin light chain proteins in the biological sample.

In certain example embodiments, the signal intensity of the second reaction mixture can be used to assess the amyloidogenic propensity of the immunoglobulin light chain proteins in the sample. In certain example embodiments, non-amyloidogenic immunoglobulin light chain proteins can be used with the competition assay (as a negative control). That is, the signal intensity generated by the second reaction mixture, for example, can serve as a control or baseline level of binding. In certain example embodiments, immunoglobulin light chain proteins from a multiple myeloma subject can be used as the non-amyloidogenic control (see, e.g., white bars of FIG. 13).

By comparing the relative signal intensities between the non-amyloidogenic reaction mixture (negative control) and a second reaction mixture generated from the use of a biological sample of a subject, the relative affinity of the immunoglobulin light chain proteins for the fibrils can be assessed. A signal intensity at or below the non-amyloidogenic second reaction mixture signal intensity, for example, indicates that the immunoglobulin light chain proteins of the biological sample bind the fibrils at a relatively high level, thus indicating an increased propensity for the immunoglobulin light chain proteins in the sample to be amyloidogenic. That is, the immunoglobulin light chain proteins out-compete the detectably-labeled synthetic fibril precursor monomers, thus decreasing the generated signal. Conversely, a signal intensity that is at or above the signal intensity of the non-amyloidogenic sample indicates that the immunoglobulin light chain proteins are not likely to be amyloidogenic.

In certain example embodiments, the signal intensity determined from the second reaction mixture can be used to determine a signal intensity value for the second reaction mixture of the competition assay. As with the direct binding assay, for example, the signal intensity value can be determined via normalization of a reaction mixture signal to a signal intensity maximum (as a positive control). For example, the signal intensity of the second reaction mixture of the competition assay can be compared to a signal intensity maximum generated from a positive control. As those skilled in the art will appreciate, the positive control can be performed in conjunction with the competition assay of the biological sample, such as on the same well-plate as the assay of the biological sample.

To determine the signal intensity maximum, the signal intensity maximum can be determined as described for the direct binding assay. Briefly, fibril precursor monomers—of the same type used to generate the fibrils of the second reaction mixture—can be detectably-labeled. An excess of the detectably-labeled fibril precursor monomers can then be contacted with the fibrils to form a control reaction mixture. Following a wash step to remove any unbound detectably-labeled fibril precursor monomers from the control reaction mixture, a control signal can be detected from the control reaction mixture via the detectable labels. A determined control signal intensity from the signal can correspond to the maximum signal intensity (i.e., from maximum binding of the monomers to the fibrils). Such maximum binding, for example, can be used as a positive control (see black bars in FIG. 13). As with the direct labeling assay, the signal intensity of the second reaction mixture for the biological sample can be compared to the maximum signal intensity to determine the signal intensity value. For example, the signal intensity value can then be determined as a fraction of the signal intensity of the reaction mixture for the biological sample relative to the maximum signal intensity. In certain example embodiments, diluted serum can be added to the control reaction mixture as described herein.

In certain example embodiments, the signal intensity value of the second reaction mixture of the competition assay can be compared to a threshold value, such as to determine whether the biological sample includes amyloidogenic light chain proteins and/or to assess the amyloidogenic risk to a subject. As described herein, because the signal intensity of the second reaction mixture (including the biological sample) inversely corresponds to the level of binding the immunoglobulin light chain proteins of the biological sample to the fibrils in vitro, the higher the signal intensity value the lower the propensity for the immunoglobulin light chain proteins in the biological sample to be amyloidogenic. Hence, for the competition assay, the threshold value is a number below which the immunoglobulin light chain proteins of the biological sample are deemed amyloidogenic. Above the threshold value, the immunoglobulin light chain proteins of the biological sample can be deemed less amyloidogenic or non-amyloidogenic. In this way, for example, the competition assay can provide an indication of the amyloidogenic risk to a subject.

As with the direct labeling assay, in certain example embodiments the threshold value for the competition assay can be an assigned value that is a fraction of the maximum signal intensity. For example, the threshold value can be about 30, 35, 40, 45, 50, 55, 60, 65, 70, 75, 80, 95, or 90% of the maximum signal intensity. If threshold value is about 40%, for example—and the signal intensity value is 55% for the second reaction mixture of the competition assay—the immunoglobulin light chain proteins of the biological sample can be identified as non-amyloidogenic. In certain example embodiments, the threshold value can be a value above which the immunoglobulin light chain proteins can be deemed to be non-amyloidogenic or less amyloidogenic. For example, if the signal intensity value is above a threshold value of about 65, 60, 55, 50, 45, 40, 35% (of the maximum signal intensity), the immunoglobulin light chain proteins in the sample can be deemed to be non-amyloidogenic.

Additionally or alternatively, in certain example embodiments the threshold value for the competition assay can be determined empirically using known amyloidogenic or non-amyloidogenic biological samples. That is, the competition assay as described herein can be performed using samples known to include immunoglobulin light chain proteins that are either amyloidogenic or non-amyloidogenic, as described herein. When determining threshold values for the competition assay using known amyloidogenic or non-amyloidogenic biological samples, a sample known to include amyloidogenic or non-amyloidogenic immunoglobulin light chain protein can be mixed with the detectably-labeled monomers as described herein to form, for example, an amyloidogenic reaction mixture or a non-amyloidogenic reaction mixture. The amyloidogenic reaction mixture or a non-amyloidogenic reaction mixture can then contacted with the synthetic fibrils to form a threshold reaction mixture. The threshold reaction mixture, for example, corresponds to the second reaction mixture of the competition assay for example, but uses a known sample. In certain example embodiments, such as when isolated or enriched immunoglobulin light chain proteins are used to form the threshold reaction mixture, serum can be added to the threshold reaction mixture. For example, 2, 5, 10, 15, 20, 25, or 30% serum can be added to the threshold reaction mixture.

Following any incubation period as described herein, the threshold signal intensity can be determined from the threshold reaction mixture. The threshold signal intensity of the threshold reaction mixture can then be converted to a threshold value by comparing—for each of the one or more sample types—the threshold signal intensity to a maximum signal intensity (i.e., comparing to a positive control signal intensity as described herein). For example, when using a radioactive detectable label, a non-amyloidogenic multiple myeloma sample can have a signal intensity of 76,315 cpm, whereas the maximum signal intensity can be 99,261 cpm, thus resulting in a threshold value of 0.77 or 77% of the maximum signal intensity (for the non-amyloidogenic light chain sample). In another example, an amyloid biological sample can have a threshold signal intensity of 41,127 cpm, whereas the maximum signal intensity can be 97,812 cpm, thus resulting in a threshold value of about 0.42 or 42%. As with the direct binding assay, in certain example embodiments the assessment of known samples can be repeated for multiple samples in order to arrive at an average or median value that represents the threshold value. For example, multiple amyloid samples can be assayed with the competition assay to determine an "amyloid" threshold value that is an average or median value for multiple amyloid samples.

By determining threshold values based on known sample types as described herein, the threshold values can be used to identify immunoglobulin light chain proteins in a biological sample of a subject as amyloidogenic or non-amyloidogenic. For example, a second reaction mixture from a biological sample of a subject with a signal intensity value above a determined threshold value can be deemed non-amyloidogenic, whereas a biological sample from a subject having a signal intensity value below the determined threshold value can be deemed to be amyloidogenic. If the determined threshold value for an amyloidogenic sample is 44%, for example, a biological sample from a subject having a signal intensity value of 55% can be identified as non-amyloidogenic. Conversely, a biological sample from a subject having a signal intensity value of 38% (i.e., below the threshold value of 44%) can be identified as amyloidogenic. In certain example embodiments, the threshold values determined from known amyloidogenic or non-amyloidogenic sample types can be about 35, 40, 45, 50, 55, 60, 65, or 70%.

In certain example embodiments, the threshold values described herein for the competition assay can be used to define various risk groups for developing amyloid. For example, the threshold value for the competition assay can be assigned at varying levels (percentages of a maximum intensity) depending on the risk to the subject of developing amyloid. In such example embodiments, a lower threshold value corresponds to a higher risk level and a higher threshold value corresponds to a lower risk level. For example, a threshold value corresponding to higher risk group can be less than about 30%, whereas a medium risk group may be about 30% to 55%. A lower-risk group, for example, can correspond to threshold value above about 55% or greater. Continuing with this example, a subject whose biological sample yields a signal intensity value of 22% in the competition assay, for example, can be categorized as having a high risk of developing amyloid (or even as having amyloidosis). Further, for a subject whose biological sample yields a signal intensity value of 45%, for example, in the competition assay can be advised that he or she is at moderate risk (or even as being borderline amyloidogenic). A subject whose biological sample yields a signal intensity value of 63% in the competition assay, for example, can be placed in the low-risk amyloidogenic group and treated accordingly.

In certain example embodiments, the assigned threshold values for the risk groups can be determined based on the use of known amyloidogenic or non-amyloidogenic samples as described herein. That is, the threshold values generated using the known amyloidogenic or non-amyloidogenic sample types in the direct binding assay can be used to establish the risk groups. For example, if the threshold value determined for a non-amyloidogenic sample is 50%, a subject whose biological sample yields a signal intensity value of 68% can be deemed at low risk for developing amyloid. Conversely, if a biological sample of a subject yields a signal intensity value of 33%—i.e., below the threshold value determined for the non-amyloidogenic sample—the subject can be identified as high risk for developing amyloid (or even as having amyloidosis). A subject whose biological sample yields a signal intensity value of 50% can be deemed at moderate risk for developing amyloid.

While the above threshold values and ranges are examples for the competition assay, one skilled in the art will appreciate, based on this disclosure, that such threshold values and ranges can be adjusted, expanded, narrowed, or otherwise changed in order to identify the risk of amyloidosis in a subject using the competition binding assay or to identify amyloidogenic protein. For example, the threshold values described herein for the competition assay can be converted to a scale or range, such as a range from 1-10, with 1 being low risk (and a signal intensity from the second reaction mixture that approximates the maximum signal intensity) and 10 being high risk (with a very low intensity of the second reaction mixture). In other examples, the threshold values can only be used to differentiate non-amyloidogenic samples from amyloidogenic samples.

Competition Assay with Sample Dilutions

In certain example embodiments, the competition assay described herein can be performed on multiple concentrations of a biological sample, such as a portion of the biological solution that has been diluted to form sample dilutions having different concentrations. A sample gradient can then be determined from the signal intensities of the second reaction mixtures of the competition assays performed using the sample dilutions. The sample gradient from the sample dilutions can then be compared to a threshold value to identify amyloidogenic proteins using the dilution-based competition assay and to provide an indication of the amyloidogenic risk to the subject.

The biological sample used for the dilutions can any biological sample that is compatible with the competition assay. Once obtained from a subject, all or a portion of the biological sample can be diluted to form the sample dilutions. In certain example embodiments, the sample dilutions can include an undiluted (fully concentrated) portion of the biological sample as well as one or more dilutions of the biological solutions. In other example embodiments, the sample dilutions may not include an undiluted sample, but rather only dilutions of the biological sample. For example, a biological sample from a subject can be serially diluted, with the final set of dilutions including the undiluted original sample and several serial dilutions of the same.

As those skilled in the art will appreciate, however, at least two sample dilutions of different concentrations are needed to determine a sample gradient as described herein.

In certain example embodiments, the dilutions can be serial dilutions, such as dilutions of 20%, 10%, 5%, 2%, 1%, 0.5%, 0.1%. To dilute the serum, any number of diluents can be used that are compatible with the competition assay. Example diluents include e.g., PBS, HEPES-buffered saline, tris-buffered saline with or without inclusion of a protein carrier such as bovine serum albumin (e.g., 0.1% w/v) or detergent (e.g. Tween™ 20; 0.01% v/v). The level of dilution for each dilution, for example, corresponds to the dilution value. For example, a sample that is a 20% dilution may have a value of 20 whereas a sample that is a 5% dilution can have a dilution value of 5. In certain example embodiments, the dilution value can correspond to the actual concentration of the diluted sample.

In certain example embodiments, following formation of the sample dilutions of the biological samples, each of the sample dilutions can be mixed with detectably-labeled synthetic fibril precursor monomers to form multiple reaction mixtures of the competition assay. The precursor monomers can be labeled, for example, as described with the competition assay. In certain example embodiments, the detectably-labeled fibril precursor monomers can be mixed with the biological sample before the sample is diluted. In such embodiments, the mixture of biological sample/detectably-labeled fibril precursor monomers can then be diluted as described herein and used with the competition assay as multiple reaction mixtures.

Following formation of the multiple reaction mixtures, each of the reaction mixtures can be separately mixed with the synthetic amyloid fibrils, in accordance with the competition assay, to form a set of second reaction mixtures of the competition assay. That is, each of the reaction mixtures arising from the sample dilutions can be used to form a second reaction mixture of the competition assay with the second reaction mixtures introducing the synthetic amyloid fibrils to the reaction mixtures. Within each of the second reaction mixtures, for example, the detectably-labeled fibril precursor monomers can compete with immunoglobulin light chain monomers for binding to the fibrils as described herein for the competition assay.

Figure 19A:
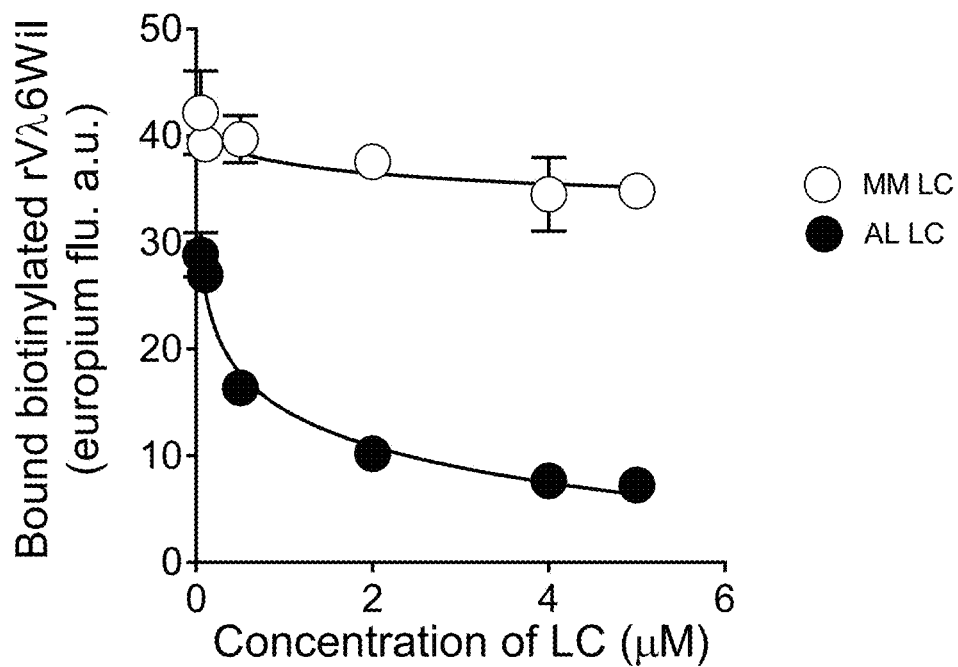
FIGS. 19A-19B are graphs showing the concentration-dependent effect of LC-mediated inhibition of biotinyl-rVλ6Wil monomer recruitment by synthetic rVλ6Wil fibrils on the microplate well, in accordance with certain example embodiments.
Figure 19B:
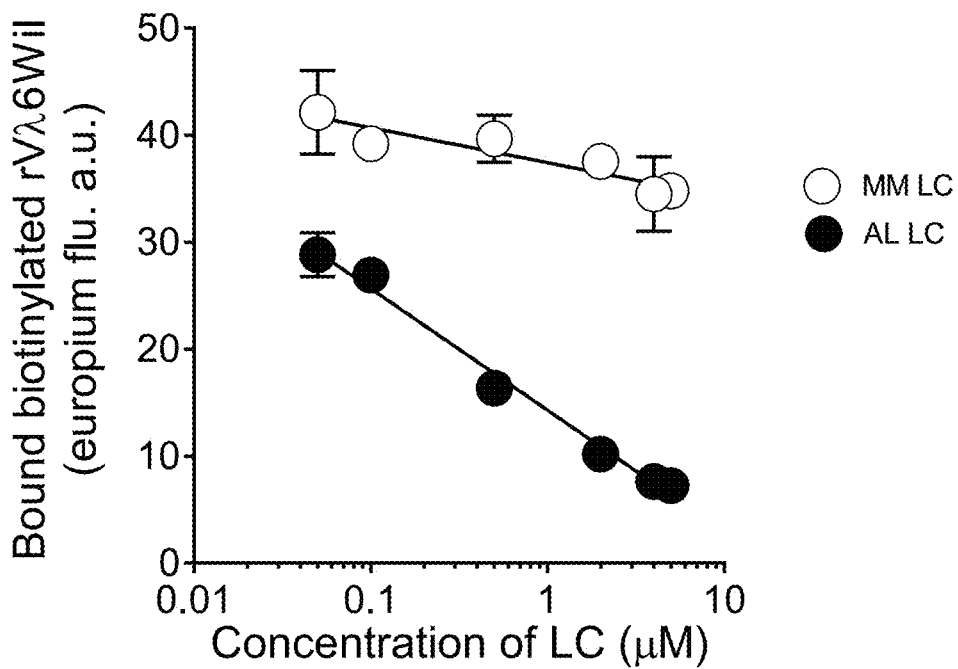

In certain example embodiments and after any wash step of the competition assay, a signal is detected from each of the second reaction mixtures of the set of reaction mixtures. A signal intensity can then be determined from each detected signal. The signal intensities corresponding to each dilution can then be compared against the dilution values to determine a gradient for the sample. For example, the signal intensities corresponding to each dilution value of the biological sample can be plotted against the dilution value. The gradient can then be determined from the comparison. As shown in FIG. 19B, for example, the biological sample can be assayed at increasing concentrations to generate a concentration-dependent gradient of inhibition (i.e., a gradient value). Based on the competition between detectably-labeled fibril precursor monomers with immunoglobulin light chain proteins in the sample dilutions for binding to the synthetic fibrils in the second reaction mixture, the binding of detectably-labeled fibril precursor monomers to the synthetic fibrils is expected to decrease as the concentration of the amyloidogenic light chain proteins in the biological is increased.

As those skilled in the art will appreciate based on this disclosure, the number of dilutions of the biological sample needed to generate the gradient can be 2, 3, 4, 5, 6, 7, 8, 9, 10 or more. The rate of change in inhibition of binding of the detectably-labeled fibril precursor monomers can be determined—from the comparison of the signal intensities to their corresponding dilutions—and expressed as a gradient value. The gradient value, for example, is expected to be negative (and of greater negative value) for biological samples containing light chain immunoglobulins with greater amyloidogenic propensity. As shown in FIG. 19B, for example, amyloid light chain protein (black circles) has a more negative gradient as compared to non-amyloidogenic multiple myeloma light chain protein (open circles).

In certain example embodiments, use of the competition assay with diluted samples to determine a gradient can be used to identify amyloidogenic protein. For example, the more negative the gradient, the more likely the immunoglobulin light chains of the biological sample are to be amyloidogenic. Hence, a subject whose biological sample yields a highly negative gradient value can be deemed to a "high risk" subject or even to have amyloidosis, whereas a subject whose biological sample yields a low gradient value can be deemed to be at "low risk" for amyloid and having a non-amyloidogenic light chain.

In certain example embodiments, the gradient value can be compared to a threshold value, such as a threshold value that is assigned to the dilution-based competition assay. For example, a threshold value can be assigned, at or below which the immunoglobulin light chain proteins can be deemed to be amyloidogenic. In certain example embodiments, the threshold value at which the immunoglobulin light chain proteins in the sample can be deemed to be amyloidogenic can be about $-4.0$, $-4.5$, $-5.0$, $-5.5$, $-6.0$, $-6.5$, $-7.0$, $-7.5$, or $-8.0$, or less. That is, a gradient falling below these amounts for a biological sample indicates that the sample contains amyloidogenic light chain proteins, whereas a gradient value above the amount indicates that the sample contains non-amyloidogenic light chain proteins. For example, if the amyloidogenic threshold value is $-5.0$, and the gradient value for a biological sample of a subject is $-3.0$, the biological sample can be deemed to be non-amyloidogenic. Conversely, if the gradient value for a biological sample of a subject is $-7.0$, then the biological sample can be deemed to be amyloidogenic.

Additionally or alternatively, in certain example embodiments the threshold value can be determined empirically using known amyloidogenic or non-amyloidogenic biological samples. That is, the dilution-based competition assay as described herein can be performed using samples known to include immunoglobulin light chain proteins that are either amyloidogenic or non-amyloidogenic, for example. The determined gradient value for each of the sample types can then be used as the threshold gradient. For example, a biological sample known to have non-amyloid light chain protein can be serially diluted, thus resulting in multiple non-amyloidogenic sample dilutions, each having a non-amyloidogenic dilution value that corresponds to the level of dilution of the sample. Each non-amyloidogenic sample dilution can then be mixed with detectably-labeled fibril precursor monomers as described herein to form the reactions mixtures of the competition assay (i.e., non-amyloidogenic reaction mixtures in this example). Each of the non-amyloidogenic reaction mixtures can then be mixed with the synthetic fibrils to form multiple threshold reaction mixtures (i.e., a set of threshold reaction mixtures) for the non-amyloidogenic sample. A threshold signal intensity, for example, can then be determined from each of the threshold reaction mixtures. By comparing the threshold signal intensities to the dilution values of the non-amyloidogenic sample dilutions, for example, a non-amyloidogenic sample gradient can be determined for the non-amyloidogenic sample— the non-amyloidogenic sample gradient corresponding to the threshold value for the amyloidogenic sample.

In certain example embodiments, the dilution-based competition assay can be used with a known amyloid sample to establish a series of amyloid sample dilution values and corresponding amyloid reaction mixtures, from which multiple threshold signal intensities can be determined. The multiple threshold signal intensities can then be used to determine an amyloidogenic sample gradient and hence an amyloidogenic threshold value as described herein. The sample, for example, can be from a subject known to have amyloidosis.

In certain example embodiments, a single amyloidogenic or non-amyloidogenic sample can be used to determine the threshold value. In certain example embodiments, several different amyloid samples or non-amyloidogenic samples can be used with the dilution-based competition assay described herein. The resultant sample gradients can then be used to determine a mean or median sample gradient and hence a mean or median threshold value for either the non-amyloidogenic sample or the amyloid sample. Additionally or alternatively, any other sample types can be used to determine the threshold values. For example, a healthy sample can be used to determine a healthy threshold value, while a multiple myeloma sample can be used to determine a non-amyloidogenic threshold value.

By determining threshold values based on known sample types as described herein, amyloidogenic proteins in a biological sample of a subject can be identified as amyloidogenic (or non-amyloidogenic). For example, if the determined threshold value for a non-amyloidogenic sample is −5.0, then a biological sample reaction mixture having a gradient value of −4.2 (i.e., above the non-amyloidogenic threshold value) can be deemed as having non-amyloidogenic immunoglobulin light chain proteins. The subject from which the biological sample was derived can also be determined as having non-amyloidogenic proteins. Conversely, if a biological sample has a gradient value of −5.8, i.e., below the non-amyloidogenic threshold, the sample can be deemed as having amyloidogenic proteins (and the subject can be deemed to be at risk of developing amyloidosis or as having amyloidosis and advised and treated accordingly).

In certain example embodiments, the threshold values described herein for the dilution-based competition assay can be used to assess amyloidogenic risk to a subject and to define various risk groups for developing amyloid. For example, the threshold value for the dilution-based competition assay can be assigned at varying levels depending on the risk to the subject of developing amyloid. In such example embodiments, a lower threshold value (more negative) corresponds to a higher risk level of developing amyloid and a higher threshold value corresponds to a lower risk level of developing amyloid. For example, a threshold value corresponding to higher risk group can be less than about −5, whereas a medium risk group may be about −3 to −4. A lower-risk group, for example, can correspond to threshold value above about −1 to −2. Continuing with this example, a subject whose biological sample yields a gradient value of −7 in the competition assay, for example, can be categorized as having a high risk of developing amyloid (or even as having amyloidosis). Further, for a subject whose biological sample yields a gradient value of −4 for example, in the dilution-based competition assay can be advised that he or she is at moderate risk (or even as being borderline amyloidogenic). A subject whose biological sample yields a gradient value of −1 in the dilution-based competition assay, for example, can be placed in the low-risk amyloidogenic group and treated accordingly.

In certain example embodiments, the assigned threshold values for the risk groups can be determined based on the use of known amyloidogenic or non-amyloidogenic samples as described herein. That is, the threshold values generated using the known amyloidogenic or non-amyloidogenic sample types in the direct binding assay can be used to establish the risk groups. For example, if the threshold value determined for a non-amyloidogenic sample is −5, a subject whose biological sample yields a gradient value of −2 can be deemed at low risk for developing amyloid. Conversely, if a biological sample of a subject yields a gradient value of −6 (i.e., more negative than the threshold value determined for the non-amyloidogenic sample), the subject can be identified as high risk for developing amyloid. A subject whose biological sample yields a signal intensity value of −4, for example, can be deemed at moderate risk for developing amyloid.

While the above threshold values and ranges are examples for the dilution-competition assay, one skilled in the art will appreciate based on this disclosure that such threshold values and ranges can be adjusted, expanded, narrowed, or otherwise changed in order to identify a disease state of a subject using the competition binding assay. For example, the threshold values based on sample gradients can be converted to a scaled value, such as a range from 1-10, with 1 being low risk (and a signal intensity from the second reaction mixture that approximates the maximum signal intensity) and 10 being high risk (with a very low intensity of the second reaction mixture).

Methods of Treatment & Kits

In certain example embodiments, provided are methods of treating a subject. The methods include, for example, selecting a subject in need of treatment. To select such a subject, a biological sample can be obtained from the subject as described herein. The biological sample is then subjected to one or more of the labeling assay, competition assay, or dilution-based competition assay. As described, these assays can be used to identify amyloidogenic proteins from the biological sample of a subject. The assays can also be used to differentiate the subject into an "at risk" group based on the subject's propensity to develop amyloidosis. For example, the subject can be placed into a low risk, medium risk, or high risk group based on the results of one or more of the assays described herein. The subject can then be treated accordingly. For example, if based on one or more of the labeling assay, competition assay, or dilution-based competition assay it is determined that the subject's immunoglobulin light chain proteins are amyloidogenic, the subject can be placed in a "high risk" group and, thereafter, monitored for the early detection of amyloidosis. Alternatively, if it is determined that the subject's immunoglobulin light chain proteins are non-amyloidogenic, then the subject can be placed in a "low risk" group and then later repeat-tested.

In certain example embodiments, subjects identified by one or more of the assays described herein—or via other methods—as having non-amyloidogenic protein can be routinely monitored via one or more of the assays described herein. For example, a subject identified as having MGUS can be routinely monitored via one or more of the assays described herein to determine if the subject's disease state has progressed. In certain example embodiments, such as when amyloidogenic immunoglobulin light chain protein is identified via the assays provided herein, the subject can be monitored with greater frequency for the presence of amyloid deposits. This can involve performing recurring biopsies on the subject and assessing the biopsies for the presence of amyloid deposits. For example, the subject can undergo a subcutaneous fat biopsy every 2, 3, 4, 5, 6, 8, or 12 months to detect the presence of amyloid in the sample by staining the Congo red dye and assessing for the presence of green-birefringent amyloid deposits (Westermark G T, Johnson K H and Westermark P. (1999), *Staining methods for identification of amyloid in tissue*. Meths in Enzymol. 309, 3-25, which is expressly incorporated herein by reference in its entirety).

In certain example embodiments, based on the results of one or more of the assays provided herein, the subject can undergo recurring imaging procedures to detect the presence of amyloid deposits. As those skilled in the art will appreciate, such imaging procedures can include, for example, the use of iodine-123 labeled serum amyloid P component; one of the many fluorine-18-labeled Aβ amyloid imaging agents such as florbetapir or florbetaben; one of several bone-seeking agents that have been shown to image amyloid such as technetium-99m-labeled 3,3-disphosphon-1,2-propanodicarboxylic acid (DPD), or pyrophosphate (PyP); or iodine-123-labeled aprotinin, which has been shown to image amyloid deposits in the heart. Other imaging agents can also be available and appropriate for monitoring the appearance of amyloid in a subject determined to be "at risk" for developing amyloidosis.

In certain example embodiments, a subject identified via one or more of the assays provided herein can be treated via the administration of amyloid-reactive monoclonal antibodies. Such antibodies include, for example, humanized antibody NEOD001 and the chimeric antibody 11-1F4, which can be useful for the removal of tissue amyloid and prevention of deposition of amyloid. In certain example embodiments, such antibodies can be used to treat a subject identified via one or more of the assays describe herein as having amyloidogenic protein (or a high-risk subject). In certain example embodiments, early detection of an amyloidogenic immunoglobulin light chain from a biological sample of a subject via one or more of the assays described herein can allow early intervention of the subject, such as via the administration of antibodies to the subject.

In certain example embodiments, if a subject is determined via one or more of the assays described herein to be have low amyloidogenic immunoglobulin light chain protein, the subject can be monitored and be treated with the standard of care for subjects with multiple myeloma. For example, such treatment can include the use of stem cell transplantation, anti-plasma cell chemotherapy in conjunction with proteasome inhibitors, and immunomodulatory drugs such as thalidomide. For example, melphalan, bortezomib (e.g., Velcade™), thalidomide (e.g., Thalomid™), lenalidomide (e.g., Revlimid™) and corticosteroids (e.g., prednisone, dexamethasone (Decadron™)) can be used. At present, subjects with MGUS do not undergo any form of treatment until signs of secondary pathology are noted, such as renal insufficiency. These patients undergo "watchful waiting".

In certain example embodiments, the method of treatment involves identifying a subject having amyloidogenic protein as described herein, such as a subject having amyloidosis (or even borderline amyloidosis). Following identification of the subject, for example, amyloid-reactive peptides, along with antibodies to the amyloid-reactive peptides, can then be administered to the subject. Such methods, for example, can clear amyloid deposits from the subject and are described in PCT/US2015/046523, titled "Targeting Immunotherapy for Amyloidosis," which is expressly incorporated herein by reference in its entirety. Other such methods are described, for example, in PCT/US17/15905, which is also titled "Targeting Immunotherapy for Amyloidosis" and which is also expressly incorporated herein by reference in its entirety. Briefly, upon administration of the antibodies, the amyloid-reactive peptides bind the antibodies and thus pre-target the antibodies to the amyloid deposits. In other examples, an amyloid-reactive fusion peptide contains an epitope of a known antibody. When the fusion peptide is administered to a subject, the fusion peptide binds amyloids in the subject. Administration to the subject of the known antibody that binds the epitope of the fusion peptide then targets the antibody to the amyloid deposit to which the fusion peptide is bound. (See PCT/US2015/046523 and PCT/US17/15905).

In certain example embodiments, also provided are kits for identifying amyloidogenic proteins of a subject and assessing amyloidogenic risk of the subject. That is, the kits may be used to carry out the methods described herein for the direct binding, competition, and dilution-based competition assays. For example, the kits can include synthetic fibrils that can be used in each of the assays described herein. For the competition and dilution-based competition assays, for example, the kits can include detectably-labeled fibril precursor monomers that can be mixed with a biological sample and thereafter used to compete with the immunoglobulin light chain proteins from a biological sample as described herein. Further, the detectably-labeled fibril precursor monomers of the kit can be used to determine a maximum signal intensity, for example, for the direct binding assay and the competition assay. In certain example embodiments, the kits can include known protein types, such as known amyloid protein or non-amyloid protein, that can be used to determine one or more threshold values as described herein. Such kits can also include other components, such as reagents, buffers, detectable labels, well-plates, or other hardware/components for carrying out the methods described herein for the direct binding assay, competition assay, and dilution-based competition assay.

Examples

The following examples further illustrate the invention but should not be construed as in any way limiting its scope. In light of the present disclosure and the general level of skill in the art, those of skill will appreciate that the following Examples are intended to be exemplary only and that numerous changes, modifications, and alterations can be employed without departing from the scope of the presently disclosed subject matter.

As used herein, the following abbreviations apply: eq (equivalents); M (Molar); µM (micromolar); N (Normal); mol (moles); mmol (millimoles); µmol (micromoles); nmol (nanomoles); g (grams); mg (milligrams); kg (kilograms); µg (micrograms); L (liters); ml (milliliters); µl (microliters); cm (centimeters); mm (millimeters); µm (micrometers); nm (nanometers); ° C. (degrees Centigrade); h (hours); min (minutes); sec (seconds); msec (milliseconds).

Overview

Light chain (LC) amyloid deposition is a complex pathology primarily associated with light chain amyloidosis (AL) and is a particularly ominous comorbidity in a subset of patients with multiple myeloma (MM) and monoclonal gammopathy of unknown significance (MGUS). The processes governing the growth of amyloid deposits in patients remain enigmatic. Herein, we show that both AL and MM-associated LC supported amyloid fibril growth due to their recruitment by preformed, synthetic amyloid fibril seed; however, AL proteins exhibited a significantly greater recruitment efficiency. Thus, AL and MM LC proteins were discriminated accurately by virtue of their recruitment efficacy. Notably, a LC from a MM patient who developed amyloidosis was identified as an AL protein in our assay, indicating the potential to predict MM patients at risk for developing amyloidosis.

Recruitment of Proteins by rVλ6Wil Fibrils

To validate the recruitment assay, we analyzed the recruitment (specific biding) of $^{125}$I-labeled soluble rVλ6Wil monomer precursor protein by homologous rVλ6Wil synthetic amyloid fibrils, using a solution-phase pulldown assay (FIG. 4). The recruitment of $^{125}$I-rVλ6Wil monomer into fibrils increased from 62% to 93% at 1 h and 24 h incubation, respectively (FIG. 4). Using this same assay, we next investigated whether these fibril seeds could support heterologous recruitment of radiolabeled LC using the AL- and MM-associated protein AL1κ and MM1κ, respectively. Both proteins were efficiently recruited; however, at 24 h, AL1κ (76%) binding was almost 2-fold greater than that of MM1κ ((43%); FIG. 4).

Figure 10:
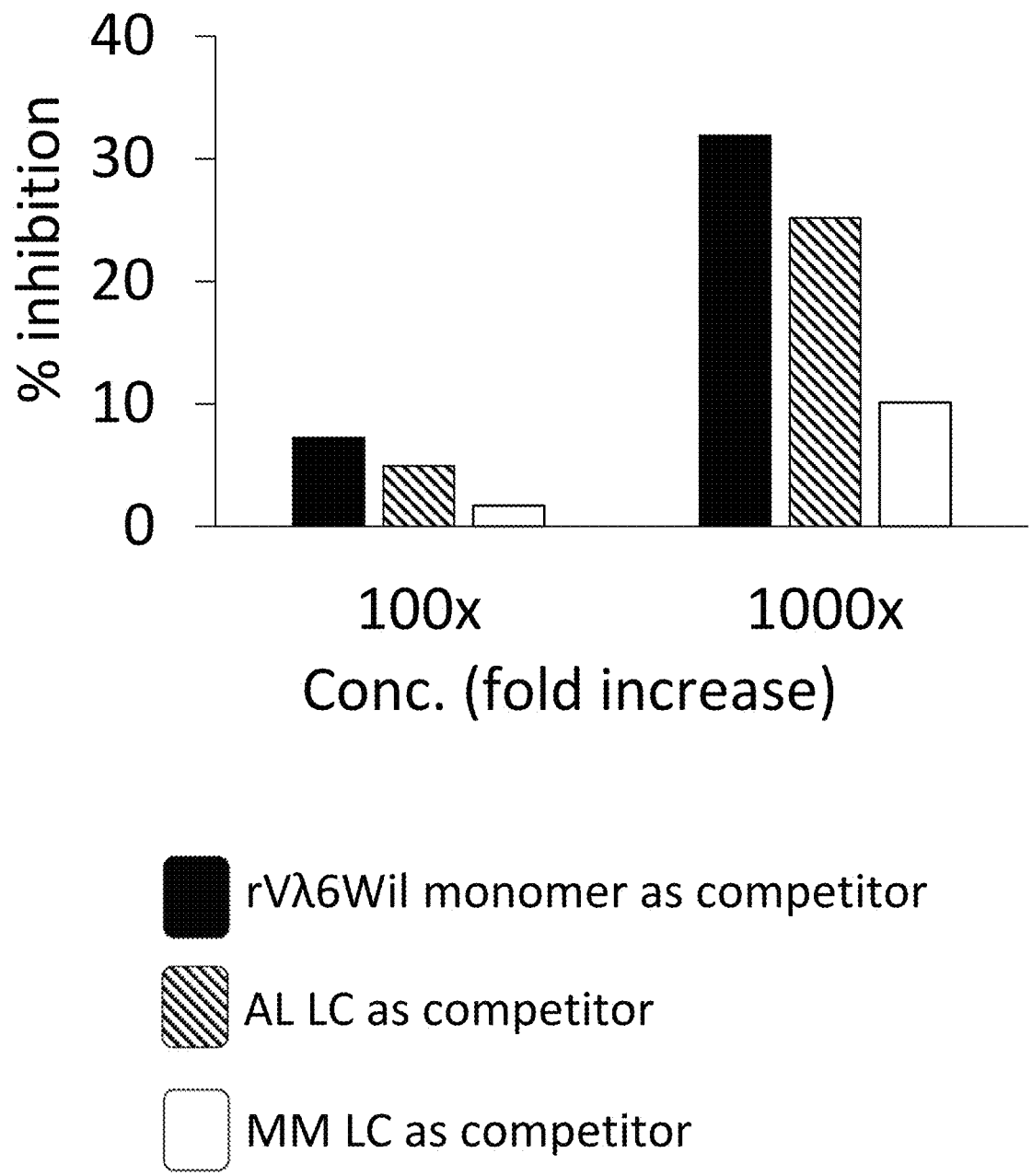
FIG. 10 is a graph showing the inhibition of $^{125}$I-rVλ6Wil monomer binding to synthetic rVλ6Wil fibrils by the presence of a 100- or 1000-fold molar excess of non-radiolabeled rVλ6Wil (black), AL1κ (hashed) or MM1κ (white). Mean±SD (n=3), in accordance with certain example embodiments. There was a significant difference between how AL-LC and MM-LC were able to block the binding of $^{125}$I-rVλ6Wil monomer to the fibrils. This ability of the competition assay to discern the two patient populations serves as the basis of one iteration of a diagnostic test for discerning non-amyloidogenic LC from those which possess increased amyloidogenic potential.

To demonstrate that binding of LC by the rVλ6Wil fibrils was similar to homologous rVλ6Wil binding, the recruitment of $^{125}$I-rVλ6Wil was measured in the presence of a 100 or 1000 molar excess of non-radiolabeled rVλ6Wil, AL1κ or MM1κ LC (FIG. 10). A 1000-fold molar excess of unlabeled rVλ6Wil inhibited binding by 30% (black bars). In contrast, inhibition of $^{125}$I-rVλ6Wil by AL1κ (hashed bar) and MM1κ (open bar) was less efficient at 25% and 10%, respectively (FIG. 10), suggesting that the heterologous recruitment of LC was of lower affinity, as compared to rVλ6Wil, but that it occurred at the same sites on the fibrils. Additionally, this competition assay demonstrated that AL and MM-derived LC proteins could be discerned using this technique, based on their relatively efficiency at blocking $^{125}$I-rVλ6Wil monomer recruitment by the fibrils.

Figure 5:
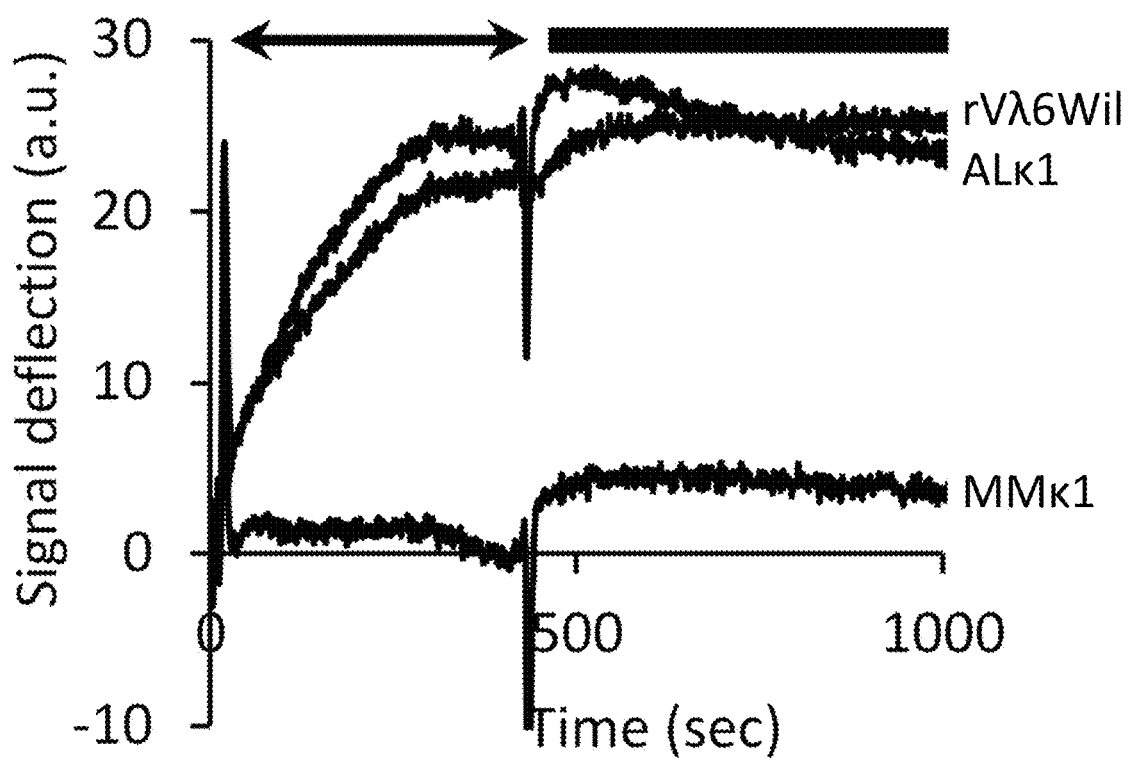
FIG. 5 is a graph showing binding of an AL LC, a MM LC and rVλ6Wil monomer by rVλ6Wil fibrils measured by surface plasmon resonance, in accordance with certain example embodiments. Representative sensorgrams for the binding of rVλ6Wil, AL1κ and MM1κ with binding phases (arrow) and washout phases (bar) are shown. This shows, again, that AL LC protein is recruited by rVλ6Wil fibrils better than a MM LC.

We also investigated the recruitment of rVλ6Wil, AL1κ and MM1κ LC (unlabeled) by rVλ6Wil fibrils using an alternative binding assay, namely surface plasmon resonance, in which protein was administered with a constant flow rate over a chip coated with rVλ6Wil fibrils. A parallel chip coated with monomeric rVλ6Wil served as the control. The binding profiles for rVλ6Wil and AL1κ were similar with a slow binding phase over 450 sec (arrow), resulting in a small signal deflection (~23 a.u; FIG. 5). During the 600 sec washout phase (bar), neither rVλ6Wil nor AL1κ protein dissociated greatly from the fibril substrate. In contrast to these two proteins, MM1κ LC showed no binding to the fibrils under these conditions (FIG. 5).

Electron Microscopic Analysis of rVλ6Wil Fibrils with Recruited AL1κ LC

Figure 6A:
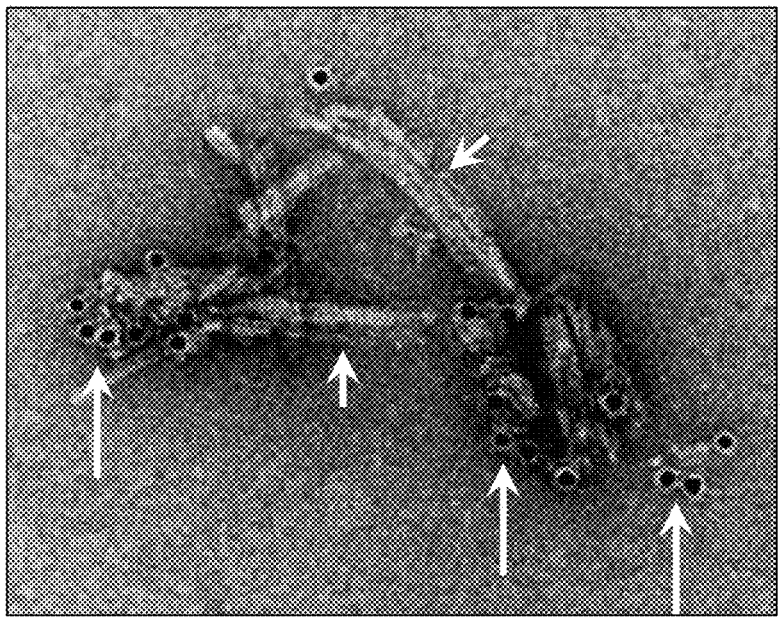
FIGS. 6A-6B are a series of micrographs showing immunogold labeling to investigate the binding sites of AL1κ LC on rVλ6Wil fibrils, in accordance with certain example embodiments.
Figure 6B:
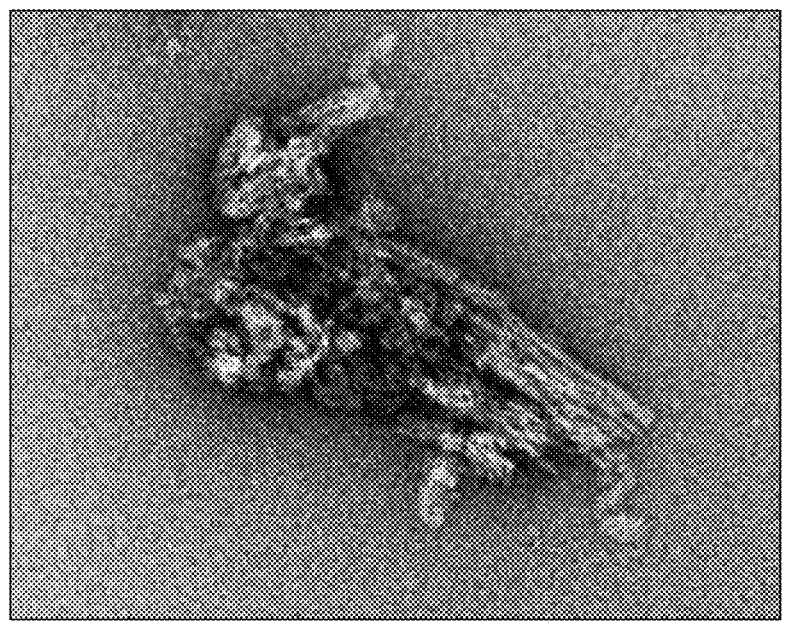
Figure 7A:
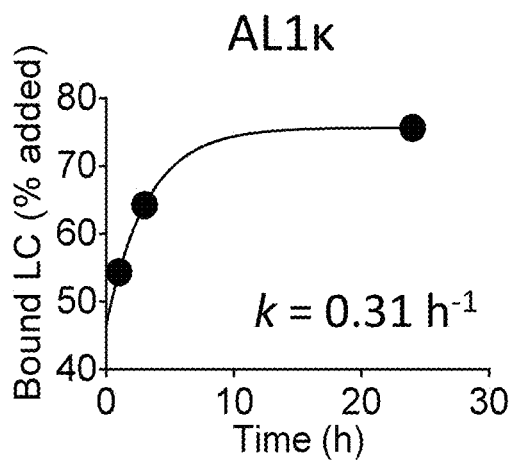
FIGS. 7A-7H are a series of graphs showing kinetic recruitment of various amyloidogenic and non-amyloidogenic kappa and lambda light chain proteins by rVλ6Wil fibrils, in accordance with certain example embodiments. For example.
Figure 7B:
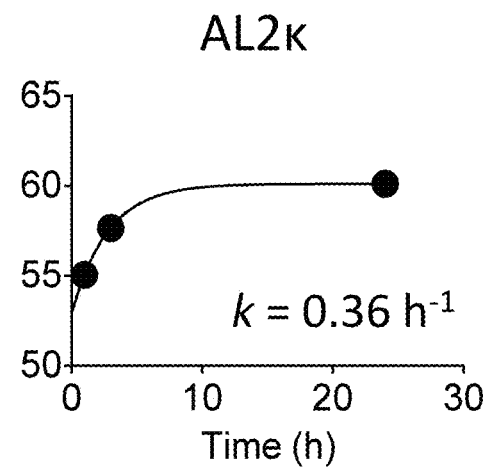
Figure 7C:
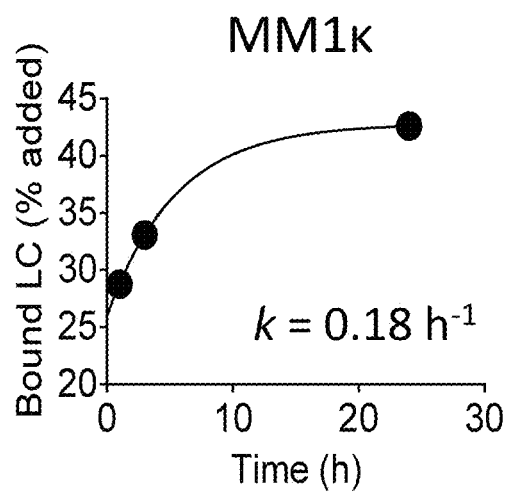
Figure 7D:
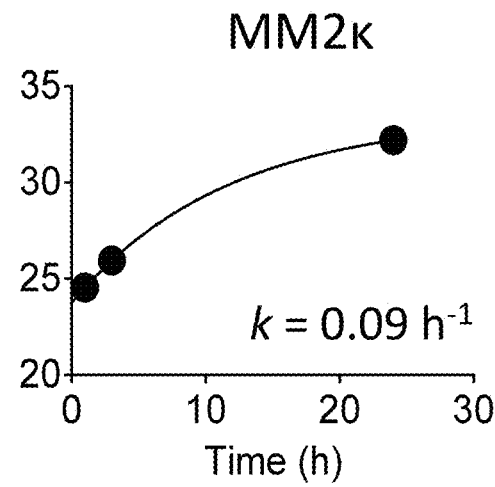
Figure 7E:
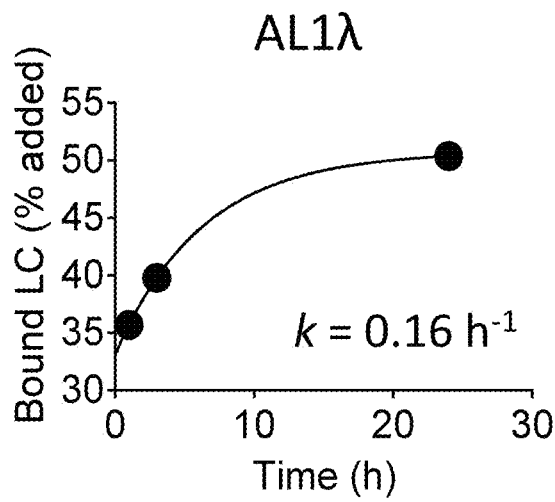
Figure 7F:
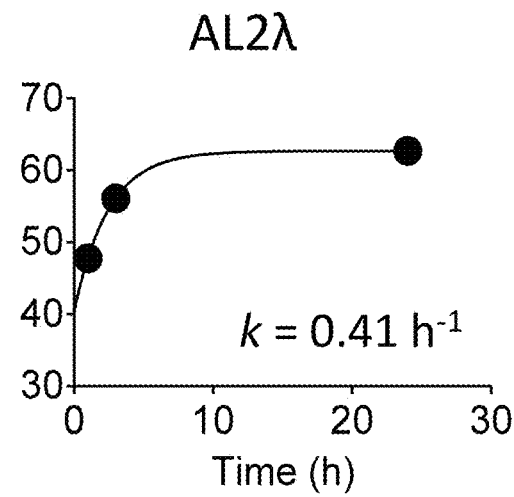
Figure 7G:
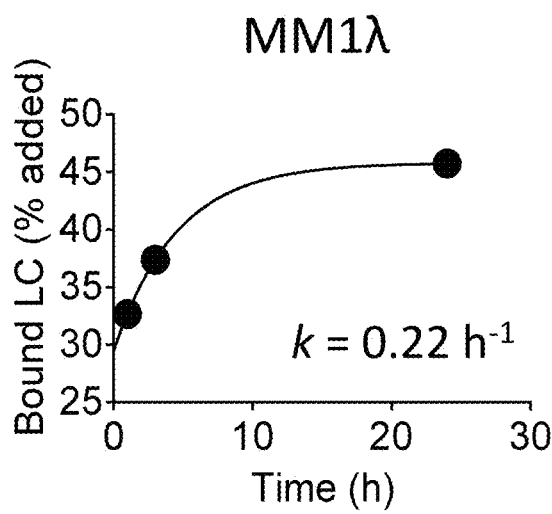
Figure 7H:
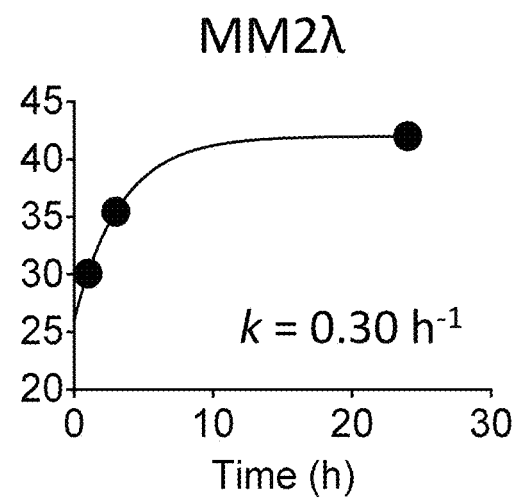

Immunogold electron microscopy was used to investigate the binding sites of AL1κ LC on rVλ6Wil fibrils (FIG. 6A and FIG. 6B). The distribution of AL1κ LC (evidenced by the presence of anti-κ LC mAb-bound 10 nm-diameter gold particles; arrows) was generally at the ends of the rVλ6Wil fibrils and less commonly seen along the length of the fibril (arrowheads; FIG. 6A). A sample of fibrils with AL1κ LC recruited but with no mAb added served as a non-specific binding control. No gold particles were observed associated with the majority of fibrils in this preparation (FIG. 6B).

Recruitment of AL and MM LC Proteins by rVλ6Wil Fibrils

In our initial experiments, both the AL1κ and MM1κ LC were recruited by rVλ6Wil fibrils but with differential efficacy; therefore, we expanded our study and assessed the binding of an additional six radiolabeled LC proteins to rVλ6Wil fibrils. AL κ (FIG. 7A and FIG. 7B) and λ (FIG. 7E and FIG. 7F) LC proteins demonstrated a steady increase in fibril-binding over 24 h. The percent LC bound at 24 h was higher for AL proteins (>50% bound), regardless of the κ or λ isotype, as compared to the MM LC (FIG. 7C, FIG. 7D, FIG. 7G, and FIG. 7H). The estimated rates of recruitment of AL LCs were variable but generally >0.3 h$^{-1}$, which contrasted with the MM proteins that were more slowly sequestered by the fibrils (FIG. 7).

Figure 8A:
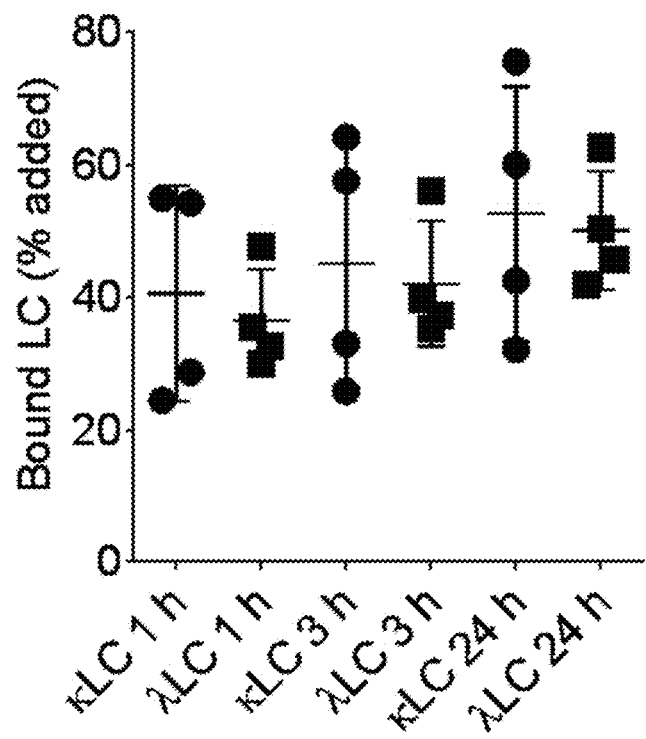
FIGS. 8A-8B are graphs showing compiled recruitment efficacy data for AL and MM LC proteins, in accordance with certain example embodiments.
Figure 8B:
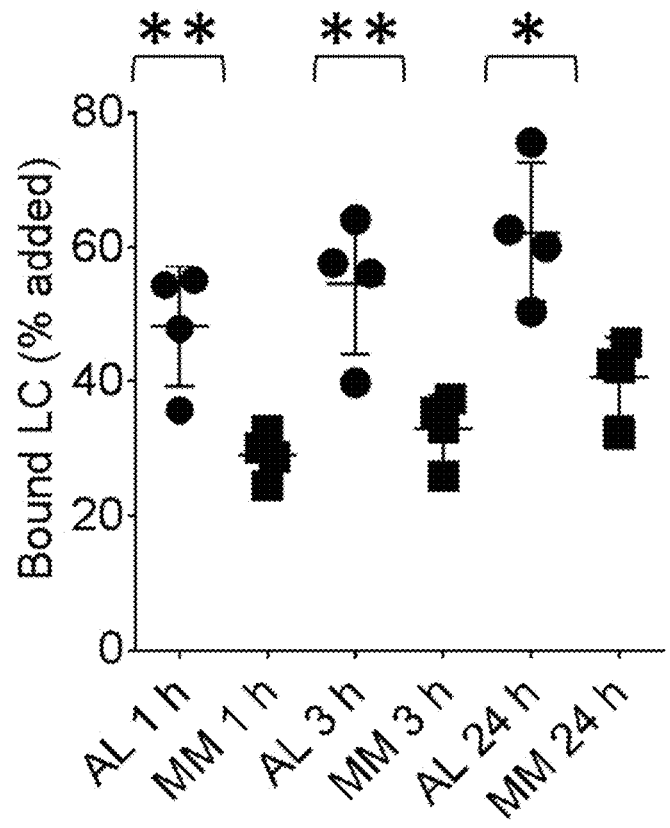
Figure 9:
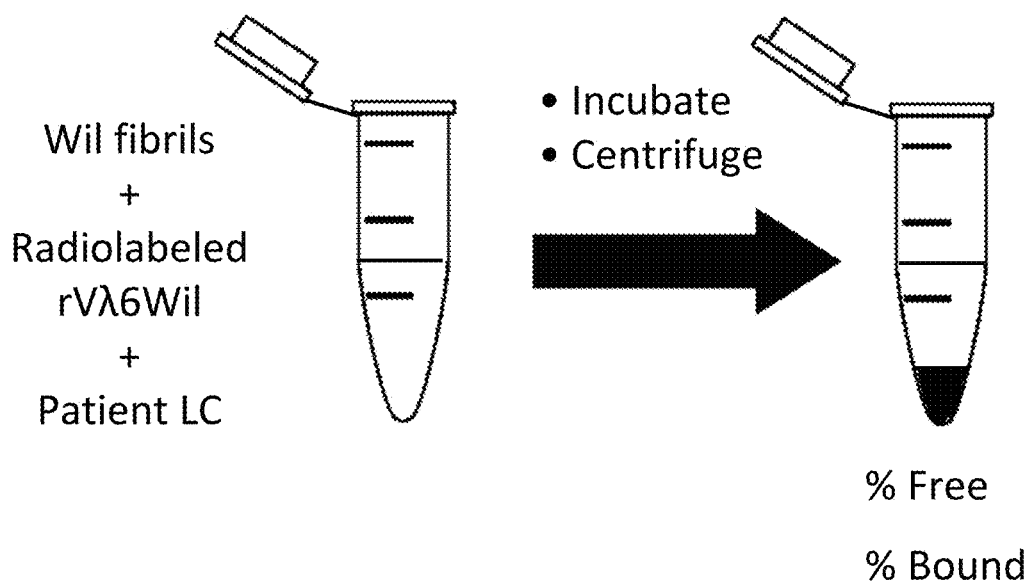
FIG. 9 is a schematic illustration showing the method for a diagnostic competition pulldown assay (version #1) for determining whether LC from patients are non-amyloidogenic (MM) or amyloid-forming, in accordance with certain example embodiments. In this assay, we studied the recruitment of $^{125}$I-labeled rVλ6Wil monomer by synthetic rVλ6Wil fibrils in the presence and absence of AL- and MM-LC, or unlabeled rVλ6Wil monomer. Our hypothesis was that rVλ6Wil monomer would effectively inhibit recruitment of $^{125}$I-rVλ6Wil by the fibrils, the AL-LC would inhibit less efficiently, and the MM-LC would be the least efficient—based on their relative binding efficiency to the fibrils.

All radioiodinated LC proteins tested were recruited by rVλ6Wil fibrils, regardless of the isotype or the disease association; however, there was a significant difference in the recruitment efficacy. Analysis of the recruitment efficacy (% bound LC) of κ and λ LC proteins at each time point, regardless of disease state, revealed no statistical difference between the two isotypes (FIG. 8A). In contrast, there was a significant difference (p<0.05) between the extent of recruitment of $^{125}$I-labeled AL and MM-associated LC by rVλ6Wil fibrils, at each time point measured (FIG. 8B).

Competition Binding Assay Using AL and MM LC Proteins and rVλ6Wil Fibrils

Figure 13:
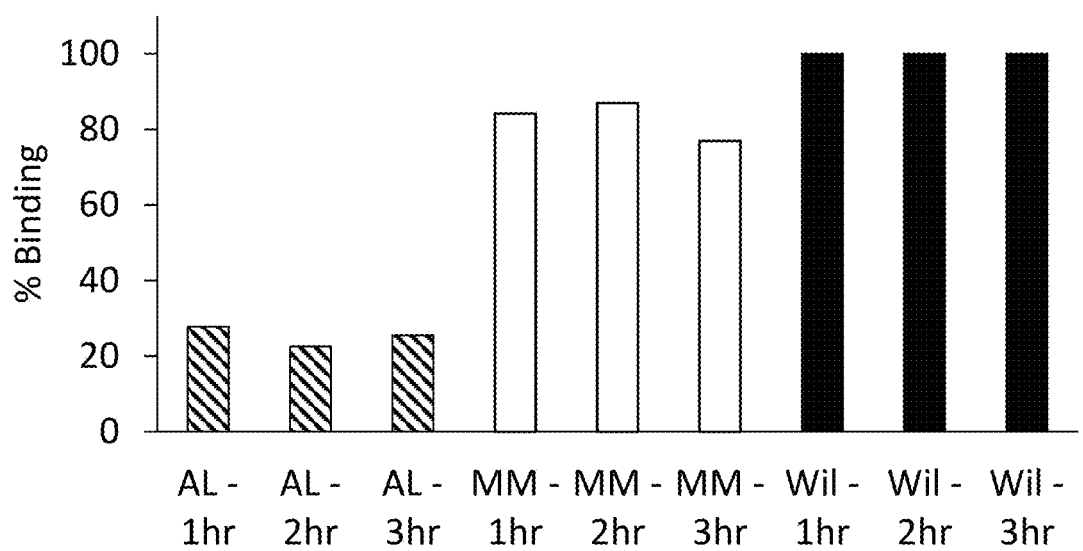
FIG. 13 is a graph showing a test of the microplate competition recruitment assay using AL- and MM-LC in the presence of biotinylated rVλ6Wil monomer and surface-adsorbed synthetic rVλ6Wil fibrils, in accordance with certain example embodiments. In this assay, the AL-LC (hashed) was significantly better at inhibiting recruitment of biotinyl-rVλ6Wil monomer by the fibrils as compared to the MM (white) protein (at all time points studied—1 h, 2 h, and 3 h of incubation). This assay was able to discern an AL LC from LC taken from an MM patient. The percent binding is normalized to that of the rVλ6Wil monomer recruitment (black) in the absence of LC protein (=100%).

Given that we have shown that amyloidogenic LC proteins are able to inhibit the recruitment of labeled rVλ6Wil monomer by synthetic rVλ6Wil fibrils more effectively than a non-amyloidogenic MM LC, we developed a competition binding assay to assess the binding of LC with fibrils. In this assay (shown schematically in FIG. 12), synthetic rVλ6Wil fibrils (100 μL of a 0.83 μM stock solution) were dried onto the wells of a 96-well microplate by overnight incubation at 37° C. To each well was added 5 nM of biotinylated-rVλ6Wil monomer in PBS, pH 7.2, alone or in the presence of 5 μM of AL1κ or MM1κ and incubated for 1 h, 2 h, or 3 h. The recruitment signal of the biotinyl-rVλ6Wil wells was set to 100% (maximum signal) and used to normalize the data for the AL1κ and MM1κ binding (FIG. 13). At each time point, the AL LC (hashed bar, FIG. 13) inhibited the binding of biotinyl-rVλ6Wil significantly more than the MM LC (white bar, FIG. 13).

Competition Binding Assay Using AL and MM LC Proteins and rVλ6Jto Fibrils

Figure 14:
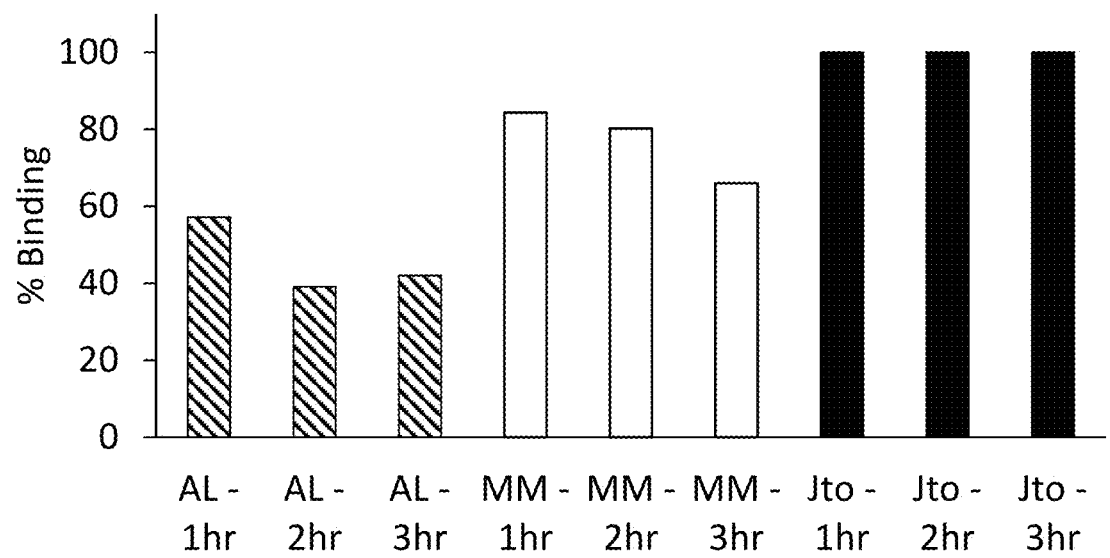
FIG. 14 is a graph showing a test of the microplate competition recruitment assay using MM- and AL-LC with a different monomer and fibril test system, in accordance with certain example embodiments. In this example, we used biotinylated rVλ6Jto fibrils and surface adsorbed rVλ6Jto fibrils. This assay was performed as described in FIG. 13; however, here we use a different VL monomer and fibril as the substrate to demonstrate that the assay can be performed with variable domain fibrils and substrate other than rVλ6Wil. The Jto VL is a λ6 protein derived from patient Jto and has a different amino acid sequence as compared to protein Wil.

A similar competition assay was performed using the λ6 VL domain derived from patient Jto (rVλ6Jto). As before, AL LC (hashed bar, FIG. 14) was more effective at inhibiting the binding of biotinyl-rVλ6Jto to synthetic rVλ6Jto fibrils as compared to MM LC proteins (white bars, FIG. 14).

Figure 17:
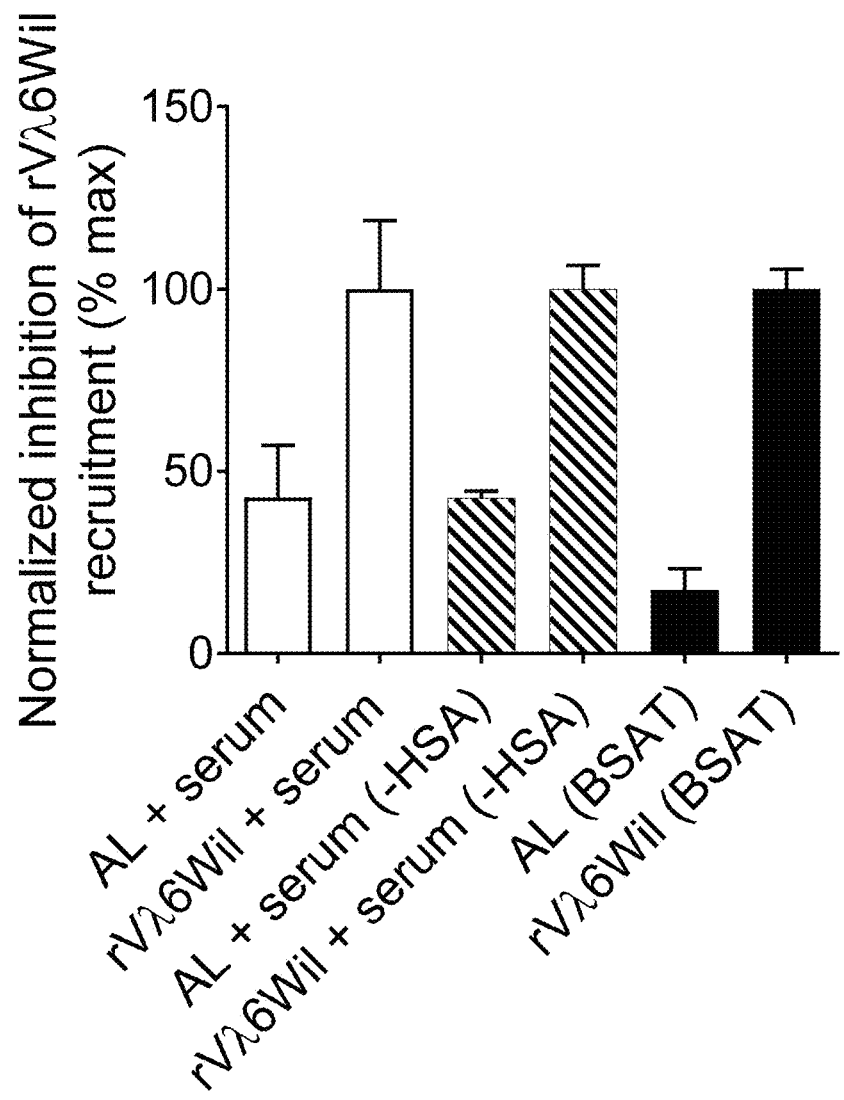
FIG. 17 is a graph showing the effect of serum and human serum albumin-depleted serum (-HSA) on the AL LC-mediated inhibition of biotinyl-rVλ6Wil monomer recruitment by synthetic rVλ6Wil fibrils on the microplate, in accordance with certain example embodiments. In the absence of serum (black), AL LC inhibited recruitment ~80%; in HSA-depleted 10% serum (hashed), the inhibition was ~60%, and in complete 10% human serum (white), inhibition was ~60%. This graph shows that AL LC mediated inhibition of biotinyl-rVλ6Wil recruitment can be observed in native and modified serum samples.
Figure 18:
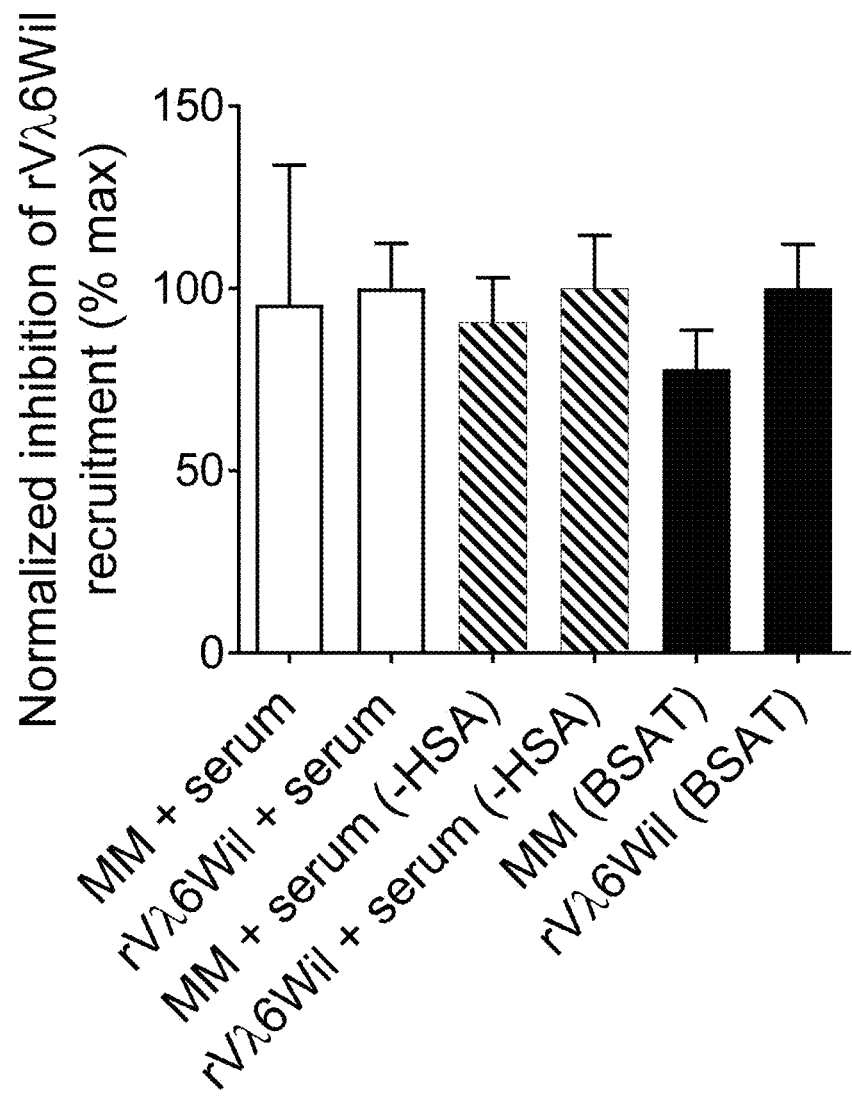
FIG. 18 is a graph showing the effect of serum and human serum albumin-depleted serum (-HSA) on MM LC-mediated inhibition of biotinyl-rVλ6Wil monomer recruitment by synthetic rVλ6Wil fibrils on the microplate, in accordance with certain example embodiments. In the absence of serum (black), MM LC inhibited recruitment ~15%; in HSA-depleted 10% serum (hashed), the inhibition was ~5%, and in complete 10% human serum (white) inhibition was ~5%. This graph shows that MM LC does not significantly inhibit biotinyl-rVλ6Wil recruitment in native and modified serum samples.

Effect of Human Serum on the Competition Binding Assay Using AL and MM LC Proteins and rVλ6Wil Fibrils We next assayed the potential effect of human serum on the competition assay using biotinyl-rVλ6Wil monomer and synthetic rVλ6Wil fibrils (FIG. 17). In a solution of PBS, with 0.5% bovine serum albumin and 0.05% Tween™ (BSAT), the AL1κ LC (black bars) reduced binding of biotinyl-rVλ6Wil monomer to synthetic rVλ6Wil fibrils by ~80%. When the same reaction was performed in the presence of 10% human serum (white bars) or 10% human serum depleted of human serum albumin (-HAS, hashed bars), the reduction in binding was ~ 60% relative to the maximal binding (FIG. 17). When a similar assay was performed using the MM1κ non-amyloidogenic LC, there was little or no inhibition of the binding of biotinyl-rVλ6Wil to the fibrils (FIG. 18).

Concentration-Dependent Inhibition Binding Using the rVλ6Wil Competition Assay

In this assay, we performed a competition assay using biotinyl-rVλ6Wil and synthetic rVλ6Wil fibrils dried onto the wells of a microplate. However, rather than using one concentration of LC in the reaction mixture as in previous experiments, we performed competition inhibition assays in increasing concentrations (0.05 µM, 0.1 µM, 0.5 µM, 2 µM, 4 µM and 5 µM) of ALκ and MMκ LC proteins (FIG. 19A and FIG. 19B). When the amount of biotinyl-rVλ6Wil bound to the fibrils (not normalized to any standard) was plotted on a semilog plot, the gradient of the curve for the ALκ LC was significantly more negative as compared to the MMκ LC (FIG. 19B).

Figure 20A:
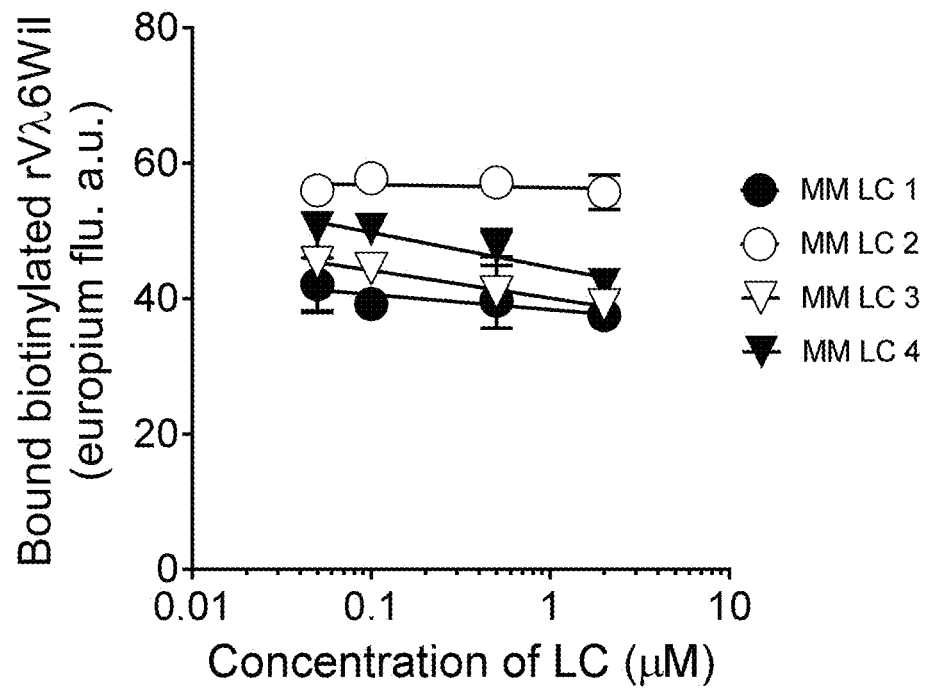
FIGS. 20A-20B are graphs showing the concentration-dependent effect of LC-mediated inhibition of biotinyl-rVλ6Wil monomer recruitment by synthetic rVλ6Wil fibrils on the microplate well, in accordance with certain example embodiments.
Figure 20B:
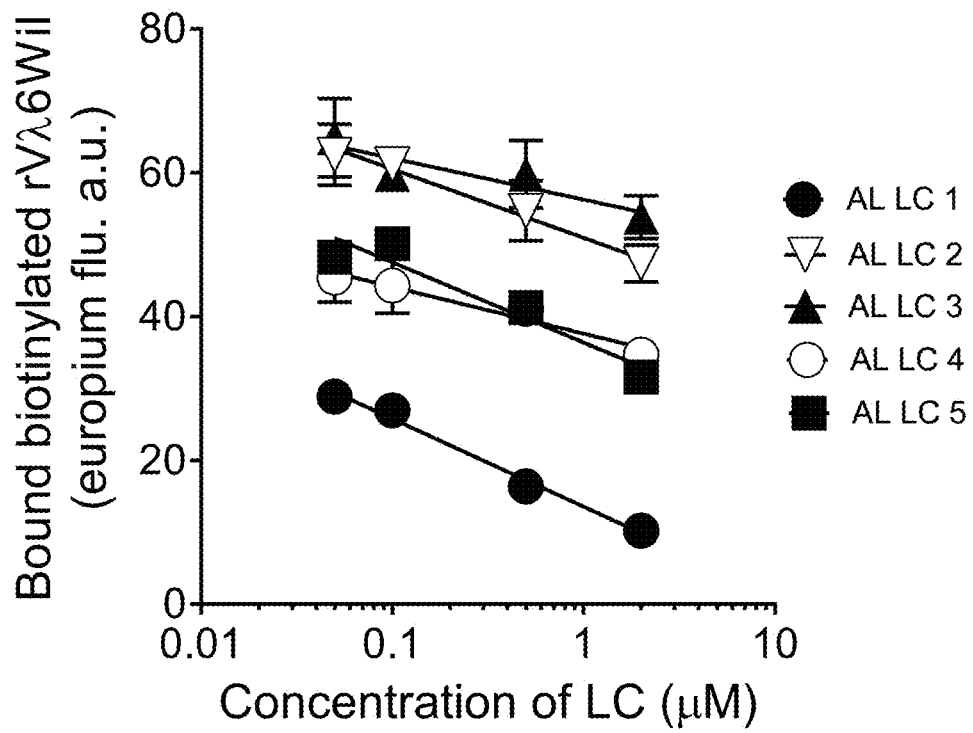
Figure 21A:
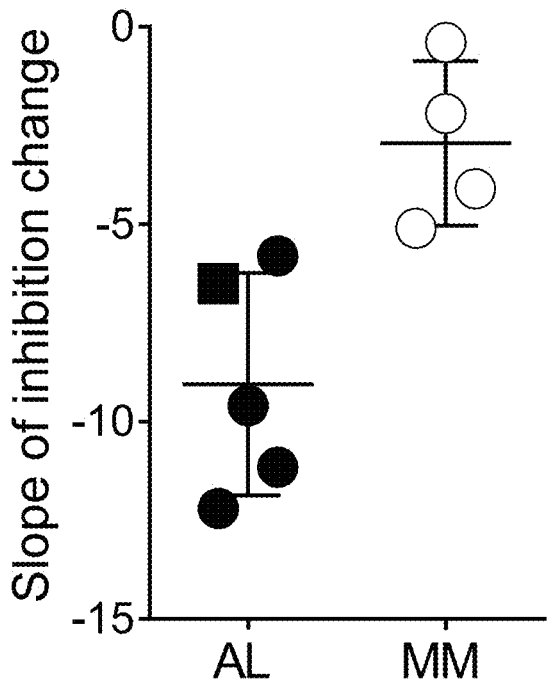
FIGS. 21A-21B are graphs summarizing the concentration-dependent inhibition gradient of LC shown in FIG. 20A and FIG. 20B, in accordance with certain example embodiments.
Figure 21B:
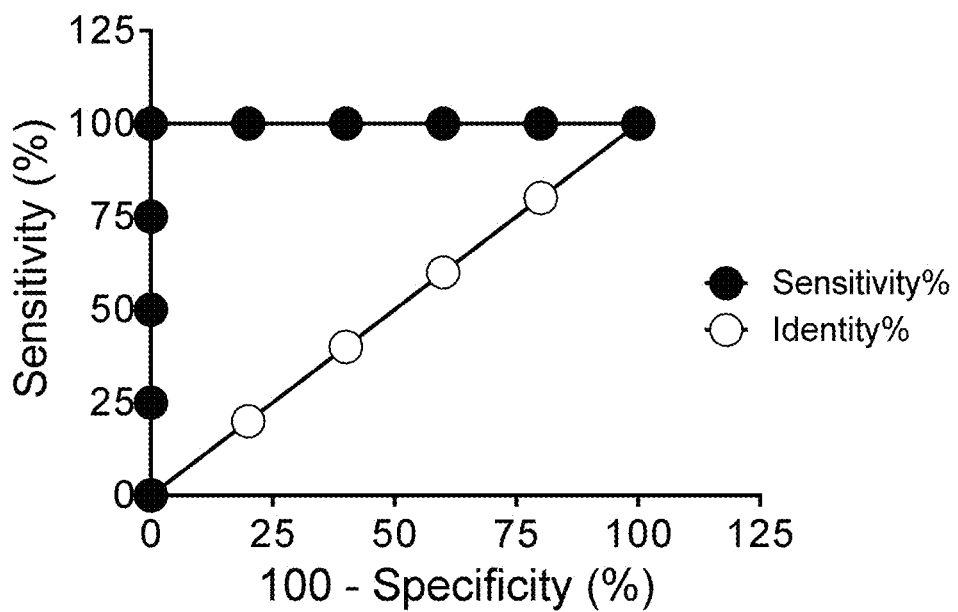

This experiment and analysis was performed using a panel of four MM LC (FIG. 20A) and five AL LC proteins (FIG. 20B) and, for these proteins, the gradients of the AL LC proteins were found to be similarly more negative than the MM LC. When the gradients of the semilog line fit to the data were calculated and plotted, we found a significant difference between the means of the AL (black) and MM (white) LC (FIG. 21A). Additionally, a threshold of −5 for the gradient was shown to accurately discriminate between the two populations, such that lines with a gradient less than (more negative than) −5 were amyloidogenic and lines with a gradient greater than (more positive than) −5 were non amyloidogenic (derived from MM patients). This was further demonstrated by plotting the data with a receiver operator curve (FIG. 21B).

Figure 22:
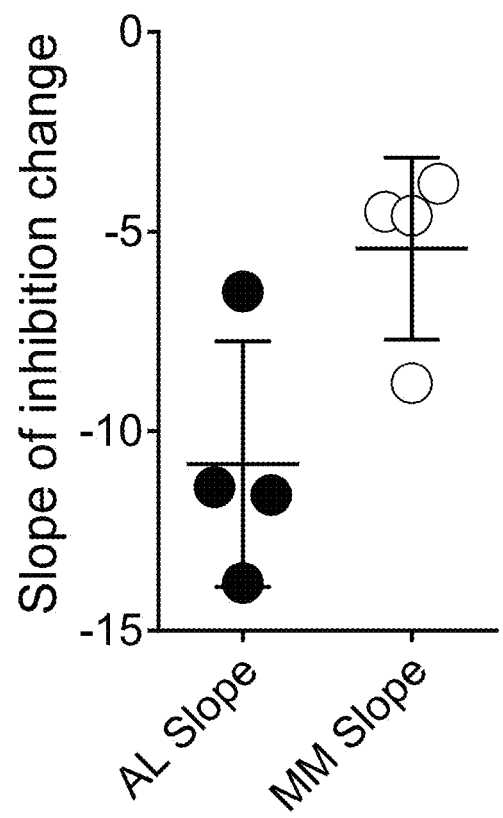
FIG. 22 is a graph showing the concentration-dependent effect of LC-mediated inhibition of biotinyl-AL1κ monomer recruitment by synthetic rVλ6Wil fibrils on the microplate well, in accordance with certain example embodiments. The mean gradient of inhibition (m is the "slope of inhibition change") for AL (black) and MM (white) LC proteins was found to be significantly different. This graph shows that the recruitment of a LC monomer protein (and not rVλ6Wil) by synthetic rVλ6Wil fibrils is inhibited more effectively by AL LC as compared to MM LC.

In another iteration of this assay, we tested the ability of four AL LC and four MM LC used at six concentrations (as described above) to inhibit the binding of a biotinylated AL LC protein (designated Cro) to synthetic rVλ6Wil fibrils dried onto the wells of a microplate (FIG. 22). Similar to the experiment described in FIG. 21, there was as significant difference in the gradient of the semilog curve. However, in this assay, the cutoff value of −5 did not provide complete separation of the LC populations, indicating that the threshold for discerning amyloidogenic from non-amyloidogenic may vary depending on the components of the binding assay.

Discussion

The growth of LC amyloid fibrils is a complex processes that is poorly understood in vivo, partly due to the lack of experimental animal models that effectively recapitulate the disease. Therefore, much of our understanding comes from in vitro studies, particularly fibrillogenesis of recombinant LC VL domain proteins. Recombinant κ4, λ6 and κ1 VL domains readily form amyloid fibrils when suspended in low pH, denaturing conditions or, in certain cases, physiological saline at pH 7.5. Fibrillogenesis from monomeric soluble VL domains can be rapid, and it is characterized by a lag time during which misfolding of the VL occurs, allowing structured self-association into thermodynamically stable oligomers that can act as templates, or seeds, for the recruitment of additional VL domains. The elongation, or growth, of fibrils following the formation of the initial seed proceeds with exponential kinetics in an essentially irreversible fashion. Mutational studies of VL domains are extensive and have elucidated numerous fibril-formation enhancing mutations at specific sites within the domain of AL-associated proteins that have not been observed in VLs derived from MM LC proteins. Most pro-fibrillogenic amino acid substitutions result in a decrease in the thermodynamic folding stability of the VL, which has led to the paradigm that unstable VL proteins that can access a more extensive unfolding landscape have a greater propensity for fibril formation and are more likely associated with amyloidosis. In contrast, VL domains from MM-associated LC proteins are generally more thermodynamically stable and, therefore, resistant to fibrillogenesis. Given this distinction, the processes underlying the clinical transition whereby MM patients develop LC amyloid is conceptually complex, involving host factors as well as a dependence on the physical properties of the LC.

The constant domain of the LC confers increased folding stability to the entire protein (variable and constant domains) and, consequently, with notable exceptions, hinders the de novo formation of amyloid fibrils by purified LC proteins in vitro. Thus, the role of the full length LC in the initial development of the amyloid seed and subsequent growth of the fibrils remain enigmatic.

Our data show that, in the presence of synthetic fibrils composed of VL fragments—similar to that found in the amyloid deposits of patients—full length LC proteins can be recruited by the fibril almost as effectively as the variable domain that comprises the seed (FIG. 4). Competition binding studies have demonstrated that an excess of AL or MM LC partially inhibited the recruitment of $^{125}$I-labeled rVλ6Wil protein by the seed, indicating that, in each case, the LC occupied similar recruitment sites used by homologous rVλ6Wil monomer (FIG. 10).

Figure 3:
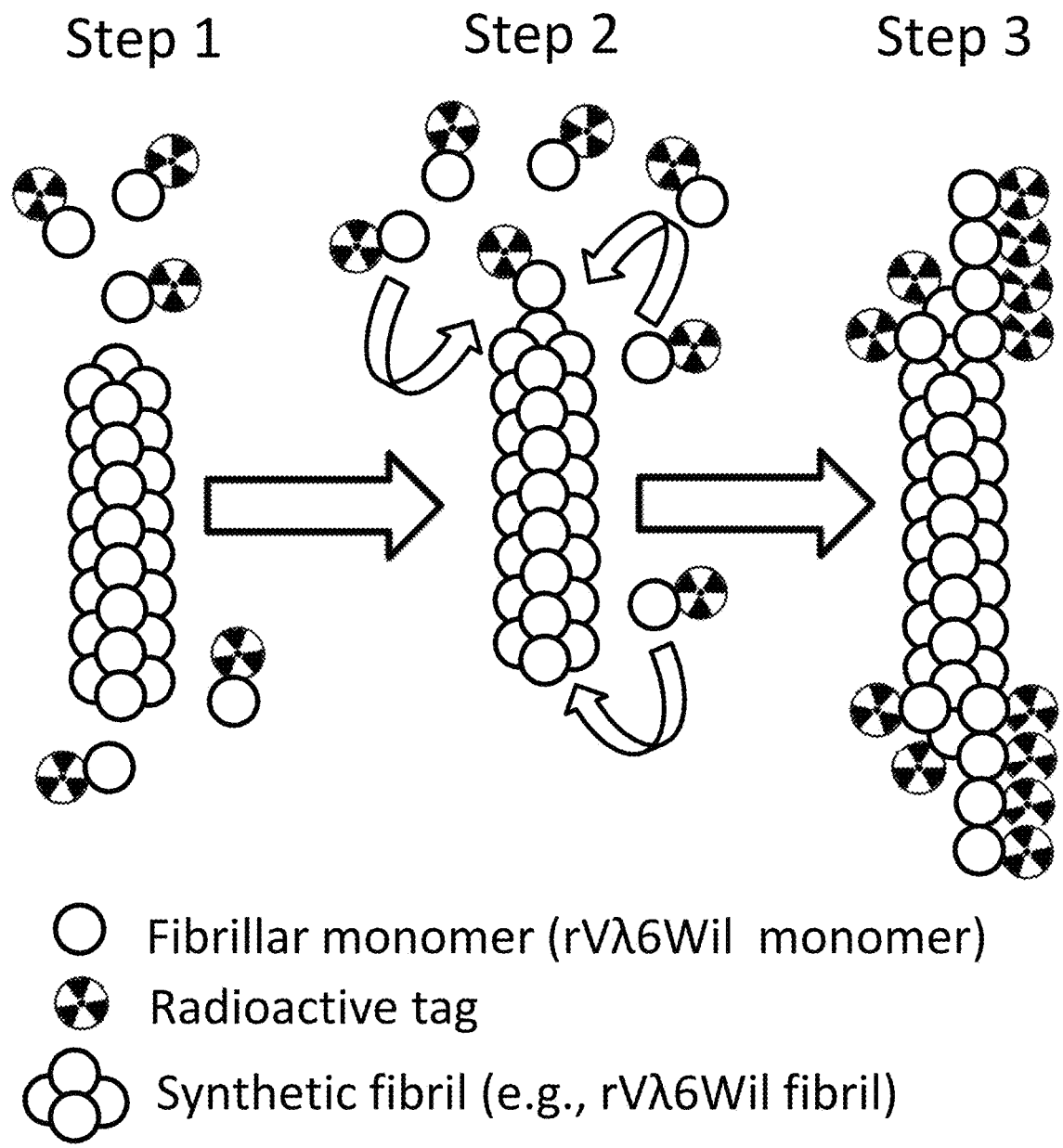
FIG. 3 is a schematic illustration representation of the recruitment of $^{125}$I-labeled rVλ6Wil by Wil fibrils in the pulldown assay, in accordance with certain example embodiments.

The recruitment assay (FIG. 3) further demonstrated that heterologous nucleation (that is, the binding of LC of one type by fibrils composed of LC of another type) was an efficient process for both AL and MM-associated LCs; however, binding of AL LC was more efficient than binding of MM LC. Moreover, mass spectrometric analysis of human AL amyloid extracts has shown the presence of more than one constant domain in some samples, which could indicate the presence of polyclonal LC proteins.

Our studies with LC derived from AL and MM patients indicate that MM LC are not inert but can be effectively recruited by synthetic fibrils; however, the amount recruited per 24 h is ~50% less than that for AL-associated LC (FIG. 4). Using the sensitive fibril recruitment assay, we were able to distinguish AL and MM-associated LC, based on the extent of binding to rVλ6Wil fibril seeds following 1 h, 3 h and 24 h of incubation, with a high degree of significance (p<0.05; FIG. 4). We considered that such an assay, or modification thereof, could be used to identify patients with plasma cell dyscrasias such as monoclonal gammopathy of unknown significance (MGUS), smoldering myeloma, and multiple myeloma (amyloid precursor disorders associated with circulating free LC) that are at greater risk for developing LC amyloidosis during the course of their disease.

Figure 15:
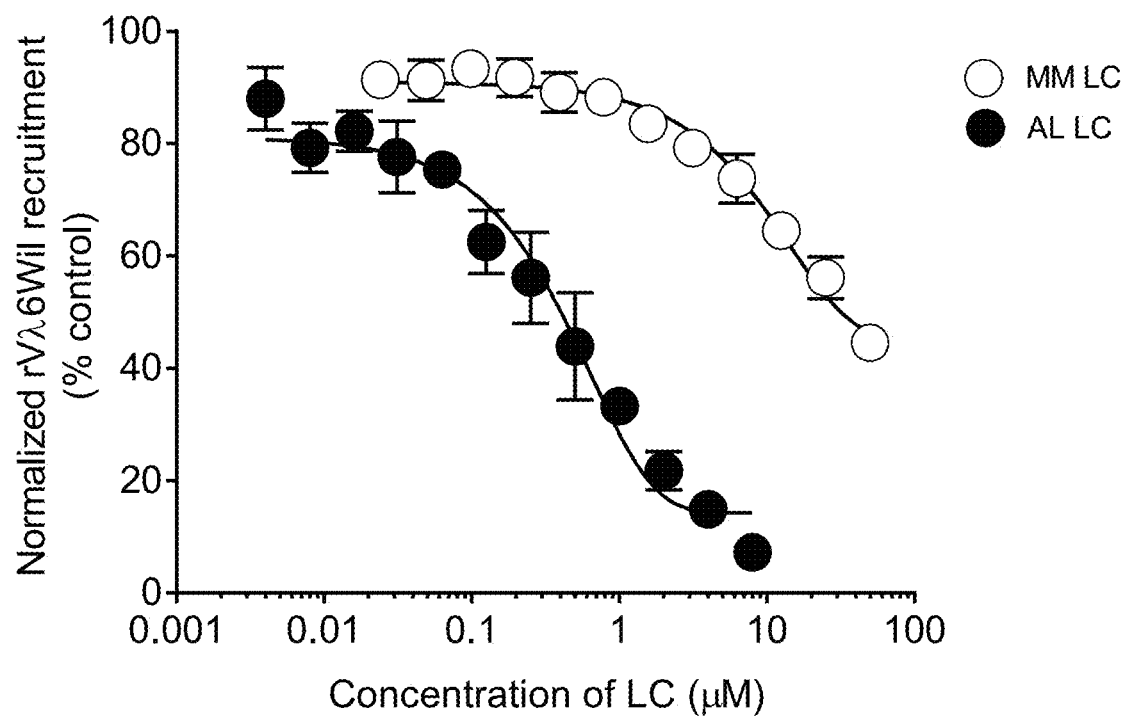
FIG. 15 is a graph showing the concentration dose-dependent effect on inhibition of biotinyl-rVλ6Wil recruitment by synthetic rVλ6Wil fibrils dried onto the wells of a 96-well microplate, in accordance with certain example embodiments. AL (black) and MM LC (white) were incubated with the biotinylated rVλ6Wil monomer at increasing concentrations and the inhibition of rVλ6Wil monomer recruitment by the LC proteins measured and normalized to the recruitment of biotinyl-rVλ6Wil in the absence of LC. There was a dramatic inhibition of recruitment by AL LC even at 1 µM LC where there was little or no inhibition by the non-amyloidogenic MM LC.
Figure 16:
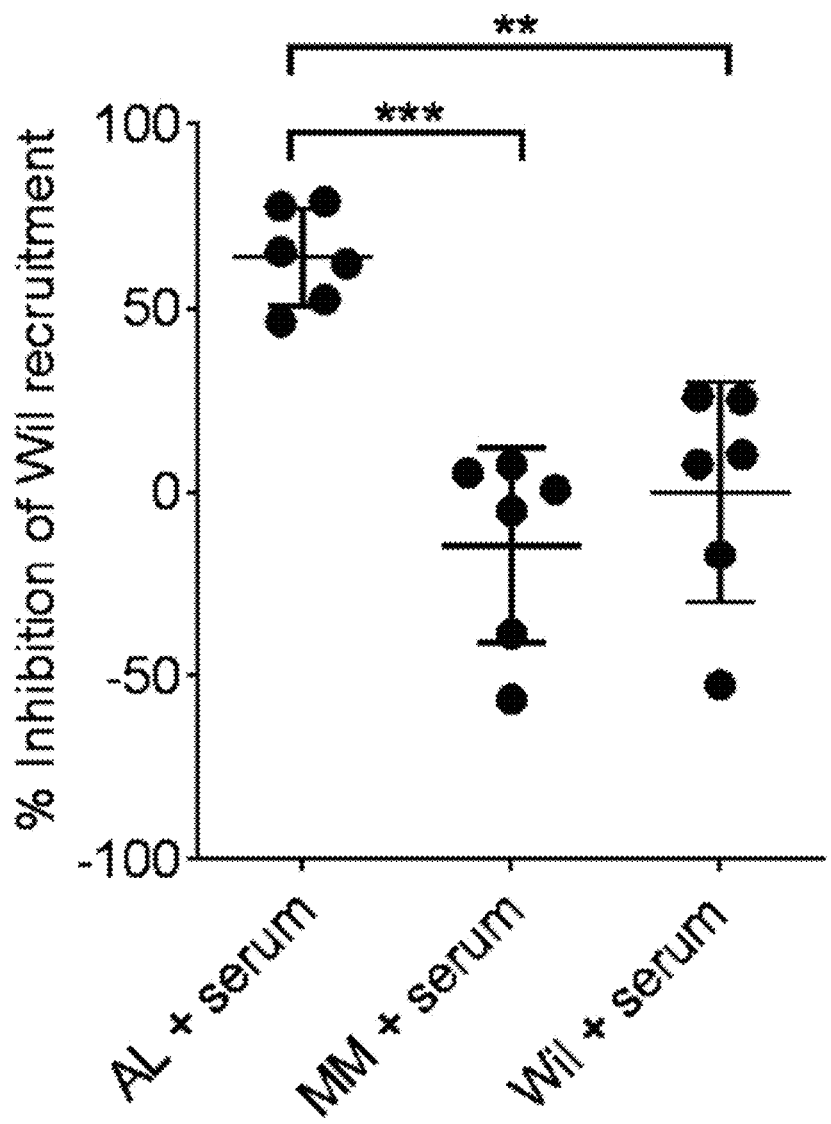
FIG. 16 is a graph showing a screen of patient-derived AL and MM LC proteins in 10% human serum using the microplate based recruitment competition assay using biotinyl-rVλ6Wil monomer and synthetic rVλ6Wil fibrils on the microplate well, in accordance with certain example embodiments. In this assay, we simulated the assay using normal human serum doped with AL and MM LC at concentrations that were consistent with that found in patients, to show that this assay could feasibly be used to screen patient serum and identify LC in the serum that are non-amyloidogenic (MM) or have a propensity for amyloid formation (AL). In this assay, there was a significant difference between the recruitment inhibition by AL and MM.

Based on our finding that AL LC more effectively inhibited the binding of rVλ6Wil to the fibrils as compared to MM LC proteins (FIG. 10), we developed a competition assay amenable to a 96 well microplate format that does not require radiolabeling of the LC protein or rVλ6Wil and may be adapted for use with biological samples (FIG. 12). Using this technique, we have demonstrated that AL LC inhibit the binding of biotnyl-rVλ6Wil to synthetic rVλ6Wil fibrils more efficiently than MM LC (FIG. 13). Inhibition of biotinyl-rVλ6Wil binding was shown to be dose dependent over the range of 0.1 µM to 10 µM for AL LC but from 2 µM to 50 µM for MM LC (FIG. 15).

The concentration-dependent decrease in binding of biotinyl-rVλ6Wil was used to develop a second method of analysis wherein we calculated the slope (or gradient) of the decrease in a semilog plot. Using this approach, we discerned AL LC exhibited a greater negative slope as compared to MM LC (FIG. 20A and FIG. 20B). This approach was able to accurately discern the two LC populations (FIG. 21A and FIG. 21B).

During our studies, using the direct LC recruitment assay (FIG. 3), we noted that the AL2κ LC was derived from a patient originally diagnosed with MM in 1992, but who ~36 months later developed clinical hepatic, splenic and renal LC amyloidosis. This LC protein was recruited more efficiently by rVλ6Wil fibril seed, as compared to the other MM patient-derived LCs, and behaved more like an AL-associated LC in the heterogeneous fibril recruitment assay (60% bound at 24 h). This observation may have clinical import given the fact that the prognosis for patients with LC amyloidosis is remarkably poor, and the ability to identify MM patients with a propensity to develop amyloid would be invaluable. Other clinical variables such as the serum free LC concentration, metrics of renal function, or the LC subtype might be used in conjunction with the LC recruitment assay to increase the predictive power for identifying patients with e.g., MGUS or MM who are at greater risk for developing amyloidosis. Such patient discrimination would initiate closer clinical surveillance, leading to earlier detection of amyloid and timely therapeutic intervention utilizing one of the novel anti-amyloid mAbs.

Materials & Methods

Fibril synthesis: Recombinant λ6 variable domain from patient Wil (rVλ6Wil) can be synthetized in *E coli* bacteria (see e.g., Wall, J. S., Schell, M., Murphy, C., Hrncic, R., Stevens, F. and Solomon, A. (1999) Thermodynamic Instability of Human λ6 Light Chains: Correlation with Fibrillogenicity. *Biochemistry*, 38, (42), 14101-14108). This protein can be used as the basis of many of the assays described herein. Fibrils can be readily made from rVλ6Wil and this process has been described previously (E.g., Wall, J. S., Murphy, C. L. and Solomon, A. (1999) In vitro immunoglobulin light chain fibrillogenesis. *Meths. in Enzymol*, 309, 204-217; Dealwis, C. and Wall, J. S. (2004) Towards understanding the structure-function relationship of human amyloid disease. *Current Drug Targets*, 5, (2), 159-171; Wall, J. S., Gupta, V., Wilkerson, M., Schell, M., Loris, R., Adams, P., Solomon, A., Stevens, F. and Dealwis, C. (2004) Structural basis of light chain amyloidogenicity: comparison of the thermodynamic properties, fibrillogenic potential and tertiary structural features of four Vλ6 proteins. *Journal of Molecular Recognition*, 17, 1-9.

Surface plasmon resonance: Recombinant Vλ6Wil fibrils were immobilized to a CM-5 chip using the amino-coupling method and reagents supplied with the BIAcore X instrument (GE Healthcare, Pittsburgh, Pa.). Briefly, chips were activated by injection (35 µL) of a mixture of N-ethyl-N'-(dimethylaminopropyl)carbodiimide (EDC) and N-hydroxysuccinimide (NHS) at a flow rate of 5 µL/min. A suspension of rVλ6Wil fibrils, diluted to 100 µg/mL in pH 4.0 NaOAc buffer (35 µL), was probe sonicated (Tekmar Sonic Disrupter with microprobe) for 10 sec immediately before injection. After fibril coupling to the Fc-1 channel, the remaining active groups on the chip were blocked by injection of 35 µL of 1 M ethanolamine-HCl, pH 8.5. Non-fibrillar Vλ6Wil, which served as a control, was similarly coupled to a chip in the Fc-2 channel. An initial regeneration step consisting of a 20 µL injection of pH 1.5 glycine buffer with 1 M NaCl was performed and the baseline allowed to equilibrate for 30 min. Light chain preparations were diluted to a stock of 5 µg/mL in HBS-EP buffer. The LC was injected (50 µL) and the binding sensorgram collected for 450 sec. A 600 sec delayed wash cycle and an additional 600 sec lag was included in the sensorgram to facilitate binding profile analysis. The chip was subjected to a regeneration step and 30 min equilibration before the next test injection. Data were extracted from the sensorgrams and analyzed using BIAevaluation (v. 3) software.

Light chain radiolabeling: Light chain proteins (50 µg) were added to 10 µL NaPO$_4$ (pH 7.6) and radioiodinated with ~0.5 mCi of iodine-125 ($^{125}$I; PerkinElmer, Waltham, Mass.) using g chloramine T, followed by addition of 40 µg sodium metabisulfite to quench the reaction. The radiolabeled product was diluted into 0.1% gelatin in sterile PBS and purified by gel filtration using a 5 mL-volume Sephadex G-25 column (PD10, GE Healthcare, Piscataway, N.J.) equilibrated with 0.1% gelatin/PBS. Peak fractions of radioactivity were pooled, and the product's radiochemical purity was measured by SDS-PAGE analyzed by phosphor imaging (Cyclone™ Storage Phosphor System; PerkinElmer™ Waltham, Mass.).

Solution phase, pulldown binding assays: Binding assays were conducted as previously described (Emily B. Martin, Angela Williams, Tina Richey, Alan Stuckey, Stephen J. Kennel and Jonathan S. Wall (2015) Comparative evaluation of p5+14, with SAP and peptide p5, by dual-energy SPECT imaging of mice with AA amyloidosis. Scientific Reports. 2016 Mar. 3; 6:22695. doi: 10.1038/srep22695) with minor modifications. Briefly, twenty-five µg of synthetic rVλ6Wil fibrils were suspended in 200 µL of PBST. Ten microliters (5-10 ng) of radioiodinated protein was added and the suspension rotated at RT for 1 h, 3 h, or 24 h. The samples were then centrifuged at 15,000×g for 10 min, supernatants collected and the pellets resuspended in 200 µL PBST before a second centrifugation at 15,000×g for 10 min. Supernatants were again removed and pooled, and the pellets resuspended in 400 µL of PBST. The radioactivity in each supernatant and pellet was measured using a Cobra II gamma counter (PerkinElmer) with a 1 min acquisition. The percentage of $^{125}$I-LC in the pellet was determined as follows:

$$\% \text{ Bound} = [\text{Pellet CPM}/(\text{Pellet CPM} + \text{Supernatant CPM})] \times 100$$

For competition assays, 100- or 1000-fold molar excess of competitor protein was added to the mixture containing fibrils and $^{125}$I-labeled rVλ6Wil prior to the 24 h incubation.

Immunogold-labeling of AL1κ bound to rVλ6Wil fibrils: Twenty-five µg of rVλ6Wil fibrils were mixed with 1 µg AL1κ LC in 200 µL of tris-buffered saline (TBS) with 0.05% Tween™ 20 (TBST) in a 1.5 mL-volume microcentrifuge tube. The sample was rotated at RT for 24 h before being centrifuged at 20,000×g for 8 min, and the supernatant was discarded. The pellet was washed in 400 µL TBST twice by centrifugation, before the sample was split into two 200 µL-volume samples in TBST. To one sample, 10 µg each of two biotinylated anti-κ mAbs (αLKC8 and 14-6E4) were added; no antibodies were added to the other sample. Both samples were rotated 2 h at RT prior to two washes by centrifugation, as before. The pellets were resuspended in 200 µL TBST with addition of a 1:4 dilution of streptavidin/gold stock solution (10 nM-diameter; Electron Microscopy Sciences, Hatfield, Pa.). After an additional 2 h rotation at RT, four washes were performed to remove unbound streptavidin-gold. Both samples were resuspended in 50 µL TBST and stored at 4° C. until being imaged.

Wil fibril extension with biotinylated Wil in the presence of human patient-derived LC: Biotinylated rVλ6Wil was prepared using the EZ-link™ Sulfo-NHS-Biotin system (ThermoFisher Scientific™, Waltham, Mass.) according to the manufacturer's protocol. Briefly, dissolve and filter rVλ6Wil protein then add the biotin and incubate at RT for 1 h before dialyzing into PBS with 3500 MWCO dialysis tubing to remove unbound biotin. The concentration of the biotinylated protein was measured by using the A280. The conjugated rVλ6Wil was stored at −80° C. in aliquots of 50 µM concentration.

For the recruitment assay, a high binding 96-well microplate was coated with 50 μL (10 μg/mL [0.83 μM]) of sonicated rVλ6Wil fibrils and the plate dried overnight at 37° C. The plate was then washed 2× with phosphate buffered saline (PBS) containing 0.05% Tween™ 20 (wash buffer) after which it was blocked by addition of 200 μL of 1% (w/v) bovine serum albumin (BSA) in PBS for 1 h at 37° C. The plate was again washed 2× with wash buffer.

As a positive control, 100 μl of 5 nM biotinylated rVλ6Wil suspended in PBS with 1% BSA and 0.05% Tween™ 20 (BSAT) was added to the microplate well. The test wells consisted of a 100 μl volume containing 5 nM biotinylated rVλ6Wil with either 5 μM LC in BSAT or a range of LC concentrations (0.05 μM, 0.1 μM, 0.5 μM, 2 μM, 4 μM and 6 μM). Background control wells contained only 100 μl of BSAT with the dried fibrils. The microplate was incubated for 1 h or 3 h or 24 h at 37° C. after which time the plate was washed 2× with wash buffer.

To develop the plate, 100 μl of a 1:1000 dilution of europium-labeled streptavidin (Perkin Elmer) in BSAT was added to each well and incubated for 1 h at 37° C. The plate was then washed 3× with wash buffer before addition of 100 μl of europium enhancement solution (Perkin Elmer) to each well. Time resolved fluorescence emission was measured using a Wallac microplate reader.

In certain experiments, we substituted 5 nM biotinylated LC Cro monomer for the biotinyl-rVλ6Wil and performed the assay, as described above. In another iteration of the microplate assay, we used biotinylated rVλ6Jto monomer and synthetic rVλ6Jto fibrils dried on the microplate well, with all other conditions as described above.

Method for Wil fibril extension with biotinylated Wil and LC with 10% serum present: To assess the effect of LC on biotinylated rVλ6Wil recruitment by fibrils in the presence of serum, the assay was performed as described above but the 1 h incubation of LC and biotinylated rVλ6Wil was performed in BSAT containing 10% normal human serum (male human AB plasma; Sigma™, St. Louis Mo.), or 10% normal human serum that had been depleted of serum albumin according to manufacturer's instructions (Pierce by ThermoScientific™, Rockford, Ill.).

Data analysis and Statistical Methods: For pulldown assays, the percent of bound radiolabeled LC was calculated according to: % bound=bound/(bound+free). This output was rather used as raw data or expressed as a percent maximal binding according to: % maximum bound=(LC bound/rVλ6Wil bound)*100. When the dose-dependent LC assay was performed, the data for all concentrations (or a subset of at least 4) were plotted on a semilog graph (log 10 x-axis) and fit using the following equation: y=m*log x+c. This yielded a linear fit with a slope of m (m was a negative value). The values of m were noted and plotted as a measure of the LC inhibition potency. Frequency and descriptive statistics were performed to check for coding errors and meet to statistical assumptions. Skewness and kurtosis statistics were used to test for normality. Any skewness or kurtosis statistic above an absolute value of 2.0 was assumed to be non-normal. Levene's test of equality of variances was used to test the assumption of homogeneity of variance. In the event of a violation of a statistical assumption, non-parametric Mann-Whitney U tests were employed. Between-subjects comparisons were conducted using independent samples t-tests. Means and standard deviations are reported for parametric statistics and medians and interquartile ranges are reported for non-parametric tests. Bivariate correlations were used to assess the relationship between continuous and ordinal variables. Statistical significance was assumed at an alpha value of 0.05. All statistical analyses were conducted using SPSS (v. 22; IBM™ Corporations, Armonk, N.Y.). Curve fitting and the ROC curve analysis were performed using Prism (v. 6.07, Graphpad™ Software Inc., La Jolla, Calif.).

| SEQUENCE LISTING FREE TEXT |
| --- |
| SEQ ID NO: 1—Human Lambda-6 Light Chain Dimer Wil: nflltqphsv sespgktvti sctrssgsia nnyvhwyqqr |
| pgsspttvif eddhrpsgvp drfsgsvdts snsasltisg |
| lktedeadyy cqsydhnnqv fgggtkltvl g |
| SEQ ID NO: 2—Human Lamda-6 Light Chain Dimer Jto nfmlnqphsv sespgktvti sctrssgnid snyvqwyqqr |
| pgsapitviy ednqrpsgvp drfagsidrs snsasltisg |
| lktedeadyy cqsydarnvv fgggtrltvl g |

In view of the many possible embodiments to which the principles of the disclosed invention may be applied, it should be recognized that the illustrated example embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of assessing amyloidogenic risk of a subject, the method comprising:
   (a) diluting a biological sample from the subject to form two or more different sample dilutions, the sample dilutions comprising different concentrations of the biological sample;
   (b) contacting each of the sample dilutions of (a) with a plurality of first synthetic fibril precursor monomers to form a plurality of reaction mixtures, wherein the first synthetic fibril precursor monomers used to form the plurality of reaction mixtures are detectably labeled;
   (c) contacting each of the plurality of reaction mixtures with a plurality of synthetic amyloid fibrils to form a set of second reaction mixtures, wherein (i) the synthetic amyloid fibrils comprise polymers of second synthetic fibril precursor monomers, the second synthetic fibril precursor monomers comprising the same monomer type or different monomer type as the first synthetic fibril precursor monomers and wherein (ii) the synthetic amyloid fibrils comprise binding affinity to the detectably-labeled first precursor monomers;
   (d) determining, from the set of second reaction mixtures of (c), a gradient value for the biological sample, wherein the gradient value is determined from signal intensities associated with each of the two or more different sample dilutions; and,
   (e) comparing the gradient value to a threshold gradient value associated with a non-amyloidogenic sample, wherein the comparison of the gradient value to the threshold gradient value provides an indication of amyloidogenic risk for the subject.

2. The method of claim 1, wherein determining the gradient value for the biological sample comprises:
   detecting, by the detectable labels, a signal from each of the second reaction mixtures;
   determining, from the detected signals, a signal intensity of each of the detected signals; and,
   comparing the signal intensity of each of the detected signals to a dilution value associated with each signal intensity, wherein the gradient value is determined from the comparison.

3. The method of claim 1, further comprising determining the threshold gradient value, wherein determining the threshold gradient value comprises:
   diluting a non-amyloidogenic sample to form a plurality of non-amyloidogenic sample dilutions, the non-amyloidogenic sample dilutions comprising different concentrations of non-amyloidogenic immunoglobulin light chain proteins;
   contacting each of the plurality of non-amyloidogenic sample dilutions with a plurality of the detectably-labeled first synthetic fibril precursor monomers to form a plurality of non-amyloidogenic reaction mixtures;
   contacting each of the plurality of non-amyloidogenic reaction mixtures with a plurality of the synthetic amyloid fibrils to form a set of threshold reaction mixtures, the synthetic amyloid fibrils comprising the same fibril precursor monomer type used in step (c) of claim 1; and, determining, from the set of threshold reaction mixtures, a non-amyloidogenic sample gradient, wherein the non-amyloidogenic sample gradient corresponds to the threshold gradient value.

4. The method of claim 3, wherein determining the threshold gradient value further comprises:

detecting, by the detectable labels of the non-amyloidogenic reaction mixtures, a signal from each of the non-amyloidogenic reaction mixtures;

determining, from the detected signals of each of the non-amyloidogenic reaction mixtures, a threshold signal intensity for each of the detected signals; and, comparing the threshold signal intensity of each of the detected signals to a non-amyloidogenic dilution value associated with each threshold signal intensity, wherein the non-amyloidogenic sample gradient is determined from the comparison.

5. The method of claim 1, wherein the subject is placed in a high-risk group for developing amyloid when the gradient value is less than the threshold gradient value or wherein the subject is placed in a low-risk group for developing amyloid when the gradient value is greater than the threshold gradient value.

6. The method of claim 1, wherein the detectably-labeled first synthetic fibril precursor monomers are detectably labeled with a fluorescent tag, a chemiluminescent tag, or a radioactive isotope.

7. The method of claim 1, wherein the plurality of synthetic amyloid fibrils consists essentially of either kappa (κ) light chain proteins or lambda (λ) light chain proteins, wherein kappa light chain proteins comprise κ1, κ2, κ3, κ4, or κ5 light chains or combinations thereof or fragments thereof and wherein the lambda light chain proteins comprise λ1, λ2, λ3, λ4, λ5, λ6, λ7, λ8, λ9, or λ10 light chains or combinations thereof or fragments thereof.

8. The method of claim 1, wherein the plurality of synthetic amyloid fibrils consists essentially of monomers having at least 95% sequence identity to the amino acid set forth as SEQ ID NO: 1 or SEQ ID NO: 2.

9. The method of claim 1, wherein providing the plurality of sample dilutions from the biological sample comprises serially diluting the biological sample.

10. A method of assessing amyloidogenic risk of a subject, the method comprising:

(a) contacting a biological sample from the subject with a plurality of first synthetic fibril precursor monomers to form a reaction mixture, wherein the synthetic fibril precursor monomers used to form the reaction mixture are detectably labeled;

(b) contacting the reaction mixture of (a) with a plurality of synthetic amyloid fibrils to form a second reaction mixture, the synthetic amyloid fibrils comprising polymers of second synthetic fibril precursor monomers, wherein (i) the second synthetic fibril precursor monomers comprise the same or different monomer type as the first synthetic fibril precursor monomers and wherein (ii) the synthetic amyloid fibrils comprise binding affinity to the detectably-labeled first precursor monomers;

(c) determining, from the second reaction mixture of (b), a signal intensity value for the biological sample; and, (d) comparing the signal intensity value to a threshold value associated with a non-amyloidogenic sample, wherein the comparison of the signal intensity value to the threshold value provides an indication of amyloidogenic risk for the subject.

11. The method of claim 10, wherein determining the signal intensity value comprises:

determining, from the detectable labels, a signal intensity associated with the second reaction mixture;

contacting a second plurality of the synthetic amyloid fibrils with a second plurality of detectably-labeled first synthetic fibril precursor monomers to form a control reaction mixture;

determining, from the control reaction mixture, a maximum signal intensity; and, comparing the signal intensity associated with the second reaction mixture to the determined maximum signal intensity to determine the signal intensity value.

12. The method of claim 11, further comprising determining the threshold value, wherein determining the threshold value comprises:

contacting a third plurality of the detectably-labeled first synthetic fibril precursor monomers with a plurality of non-amyloidogenic immunoglobulin light chain proteins to form a non-amyloidogenic reaction mixture;

contacting the non-amyloidogenic reaction mixture with a third plurality of the synthetic amyloid fibrils to form a threshold reaction mixture; and, comparing a signal intensity from the threshold reaction mixture to the maximum signal intensity to determine the threshold value.

13. The method of claim 10, wherein the subject is placed in a high-risk group for developing amyloid when the signal intensity value is less than the threshold value or wherein the subject is placed in a low-risk group for developing amyloid when the signal intensity value exceeds the threshold value.

14. The method of claim 10, wherein the plurality of synthetic amyloid fibrils consists essentially of either kappa (κ) light chain proteins or lambda (λ) light chain proteins, wherein kappa light chain proteins comprise κ1, κ2, κ3, κ4, or κ5 light chains or combinations thereof or fragments thereof and wherein the lambda light chain proteins comprise λ1, λ2, λ3, λ4, λ5, λ6, λ7, λ8, λ9, or λ10 light chains or combinations thereof or fragments thereof.

15. The method of claim 10, wherein the plurality of synthetic amyloid fibrils consists essentially of monomers having at least 95% sequence identity to the amino acid set forth as SEQ ID NO: 1 or SEQ ID NO: 2.

16. A method of assessing amyloidogenic risk of a subject, the method comprising:

providing a plurality of substantially isolated, detectably-labeled immunoglobulin light chain proteins from a biological sample from the subject;

contacting the plurality of detectably-labeled immunoglobulin light chain proteins with a plurality of synthetic amyloid fibrils to form a reaction mixture, wherein the synthetic amyloid fibrils comprise a polymer of synthetic fibril precursor monomers;

determining, from the reaction mixture, a signal intensity value for the biological sample; and, comparing the signal intensity value to a threshold value associated with a non-amyloidogenic sample, wherein the comparison of the signal intensity value to the threshold value provides an indication of amyloidogenic risk for the subject.

17. The method of claim 16, wherein determining the signal intensity value comprises:

determining, from the reaction mixture, a signal intensity associated with the reaction mixture;

contacting a second plurality of the synthetic amyloid fibrils with a plurality of detectably-labeled synthetic fibril precursor monomers to form a control reaction mixture, wherein the detectably-labeled synthetic fibril precursor monomers comprise the same or different monomer type as the synthetic fibril precursor monomers;

determining, from the control reaction mixture, a maximum signal intensity; and, comparing the signal intensity associated with the reaction mixture to the determined maximum signal intensity to determine the signal intensity value.

18. The method of claim 17, further comprising determining the threshold value, wherein determining the threshold value comprises:

providing a plurality of detectably-labeled, non-amyloidogenic immunoglobulin light chain proteins;

contacting the plurality of detectably-labeled, non-amyloidogenic immunoglobulin light chain proteins with a third plurality of the synthetic amyloid fibrils to form a threshold reaction mixture; and, comparing a signal intensity from the threshold reaction mixture to the maximum signal intensity to determine the threshold value.

19. The method of claim 16, wherein the subject is placed in a high-risk group for developing amyloid when the signal intensity value exceeds the threshold value or wherein the subject is placed in a low-risk group for developing amyloid when the signal intensity value is less than the threshold value.

20. The method of claim 16, wherein the plurality of synthetic amyloid fibrils consists essentially of either kappa (κ) light chain proteins or lambda (λ) light chain proteins, wherein kappa light chain proteins comprise κ1, κ2, κ3, κ4, or κ5 light chains or combinations thereof or fragments thereof and wherein the lambda light chain proteins comprise λ1, λ2, λ3, λ4, λ5, λ6, λ7, λ8, λ9, or λ10 light chains or combinations thereof or fragments thereof.

21. The method of claim 16, wherein the plurality of synthetic amyloid fibrils consists essentially of monomers having at least 95% sequence identity to the amino acid set forth as SEQ ID NO: 1 or SEQ ID NO: 2.

22. The method of claim 1, wherein the second synthetic fibril precursor monomers comprise the same monomer type as the first synthetic fibril precursor monomers.

23. The method of claim 10, wherein the second synthetic fibril precursor monomers comprise the same monomer type as the first synthetic fibril precursor monomers.

24. The method of claim 17, wherein the detectably-labeled synthetic fibril precursor monomers comprise the same monomer type as the synthetic fibril precursor monomers.

* * * * *

SEQUENCE LISTING

```
<160> NUMBER OF SEQ ID NOS: 2

<210> SEQ ID NO 1
<211> LENGTH: 111
<212> TYPE: PRT
<213> ORGANISM: Homo sapiens

<400> SEQUENCE: 1

Asn Phe Leu Leu Thr Gln Pro His Ser Val Ser Glu Ser Pro Gly Lys
1               5                   10                  15

Thr Val Thr Ile Ser Cys Thr Arg Ser Ser Gly Ser Ile Ala Asn Asn
            20                  25                  30

Tyr Val His Trp Tyr Gln Gln Arg Pro Gly Ser Ser Pro Thr Thr Val
        35                  40                  45
```

```
Ile Phe Glu Asp Asp His Arg Pro Ser Gly Val Pro Asp Arg Phe Ser
 50                  55                  60

Gly Ser Val Asp Thr Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp His
                 85                  90                  95

Asn Asn Gln Val Phe Gly Gly Gly Thr Lys Leu Thr Val Leu Gly
                100                 105                 110

<210> SEQ ID NO 2
<211> LENGTH: 111
<212> TYPE: PRT
<213> ORGANISM: Homo sapiens

<400> SEQUENCE: 2

Asn Phe Met Leu Asn Gln Pro His Ser Val Ser Glu Ser Pro Gly Lys
 1               5                  10                  15

Thr Val Thr Ile Ser Cys Thr Arg Ser Ser Gly Asn Ile Asp Ser Asn
                 20                  25                  30

Tyr Val Gln Trp Tyr Gln Gln Arg Pro Gly Ser Ala Pro Ile Thr Val
                 35                  40                  45

Ile Tyr Glu Asp Asn Gln Arg Pro Ser Gly Val Pro Asp Arg Phe Ala
 50                  55                  60

Gly Ser Ile Asp Arg Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ala
                 85                  90                  95

Arg Asn Val Val Phe Gly Gly Gly Thr Arg Leu Thr Val Leu Gly
                100                 105                 110
```